US009956383B2

(12) United States Patent
Schaeffer et al.

(10) Patent No.: US 9,956,383 B2
(45) Date of Patent: May 1, 2018

(54) MEDICAL DEVICES AND METHODS FOR PROVIDING ACCESS TO A BODILY PASSAGE DURING DILATION

(71) Applicants: Darin Schaeffer, Bloomington, IN (US); Paul Krakovitz, Cleveland, OH (US); Dan Dalenberg, Portage, MI (US)

(72) Inventors: Darin Schaeffer, Bloomington, IN (US); Paul Krakovitz, Cleveland, OH (US); Dan Dalenberg, Portage, MI (US)

(73) Assignees: COOK MEDICAL TECHNOLOGIES LLC, Bloomington, IN (US); THE CLEVELAND CLINIC FOUNDATION, Cleveland, OH (US)

(*) Notice: Subject to any disclaimer, the term of this patent is extended or adjusted under 35 U.S.C. 154(b) by 340 days.

(21) Appl. No.: 14/211,374

(22) Filed: Mar. 14, 2014

(65) Prior Publication Data
US 2014/0277066 A1 Sep. 18, 2014

Related U.S. Application Data

(60) Provisional application No. 61/792,415, filed on Mar. 15, 2013.

(51) Int. Cl.
*A61M 25/10* (2013.01)
*A61M 16/04* (2006.01)
(Continued)

(52) U.S. Cl.
CPC .... *A61M 25/1006* (2013.01); *A61M 16/0427* (2014.02); *A61M 16/0429* (2014.02);
(Continued)

(58) Field of Classification Search
CPC .............. A61M 16/0427; A61M 16/04; A61M 16/0402; A61M 16/0463; A61M 25/0023;
(Continued)

(56) References Cited

U.S. PATENT DOCUMENTS

| 3,173,418 A | 3/1965 | Baran |
| 3,995,643 A | 12/1976 | Merave |

(Continued)

FOREIGN PATENT DOCUMENTS

| DE | 202005017959 | 11/2005 |
| EP | 1230944 | 8/2002 |

(Continued)

OTHER PUBLICATIONS

Geisthoff, Urban W., Basic Sialendoscopy Techniques, Otolaryngol Clin N Am, 2009, p. 1029-1052, vol. 42, Elsevier Inc.

(Continued)

*Primary Examiner* — Katrina Stransky
(74) *Attorney, Agent, or Firm* — Buchanan Van Tuinen LLC

(57) ABSTRACT

Medical devices and methods of treatment are described herein. More particularly, medical devices and methods for providing access to a bodily passage during dilation are described herein. An exemplary medical device comprises an elongate member and a balloon. The elongate member is moveable between a first, non-expanded configuration and a second, expanded configuration.

20 Claims, 16 Drawing Sheets

(51) Int. Cl.
*A61M 25/00* (2006.01)
*A61M 25/06* (2006.01)
*A61M 25/04* (2006.01)
*A61M 29/02* (2006.01)

(52) U.S. Cl.
CPC .... *A61M 16/0434* (2013.01); *A61M 16/0456* (2014.02); *A61M 16/0459* (2014.02); *A61M 16/0481* (2014.02); *A61M 16/0486* (2014.02); *A61M 16/0488* (2013.01); *A61M 25/0023* (2013.01); *A61M 25/0662* (2013.01); *A61M 25/04* (2013.01); *A61M 29/02* (2013.01); *A61M 2025/0024* (2013.01); *A61M 2025/0681* (2013.01); *A61M 2025/105* (2013.01); *A61M 2025/1052* (2013.01); *A61M 2205/32* (2013.01)

(58) Field of Classification Search
CPC .. A61M 25/0662; A61M 25/04; A61M 29/02; A61M 2025/0024; A61M 2025/0681; A61M 2025/105; A61M 2025/1052; A61M 2205/32; A61M 25/1006; A61M 16/0429; A61M 16/0456; A61M 16/0459; A61M 16/0481; A61M 16/0486; A61M 16/0434; A61M 16/0418; A61M 16/0488
USPC .......... 606/192; 128/200.26, 207.14–207.17
See application file for complete search history.

(56) References Cited

U.S. PATENT DOCUMENTS

| | | |
|---|---|---|
| 4,141,364 A | 2/1979 | Schultze |
| 4,538,606 A | 9/1985 | Whited |
| 4,568,329 A | 2/1986 | Mahurkar |
| 4,693,243 A | 9/1987 | Buras |
| 4,791,923 A | 12/1988 | Shapiro |
| 4,968,306 A | 11/1990 | Huss et al. |
| 4,968,307 A | 11/1990 | Dake et al. |
| 5,009,636 A | 4/1991 | Wortley et al. |
| 5,183,464 A | 2/1993 | Dubrul et al. |
| 5,207,648 A | 5/1993 | Gross |
| 5,250,029 A | 10/1993 | Lin et al. |
| 5,251,619 A | 10/1993 | Lee |
| 5,257,979 A | 11/1993 | Jagpal |
| 5,336,178 A | 8/1994 | Kaplan et al. |
| 5,447,503 A | 9/1995 | Miller |
| 5,634,901 A | 6/1997 | Alba et al. |
| 5,653,230 A | 8/1997 | Ciaglia et al. |
| 5,782,797 A | 7/1998 | Schweich, Jr. et al. |
| 5,882,332 A | 3/1999 | Wijay |
| 5,937,861 A | 8/1999 | Augustine |
| 5,944,691 A | 8/1999 | Querns et al. |
| 6,168,586 B1 | 1/2001 | Hahnen |
| 6,179,813 B1 | 1/2001 | Ballow et al. |
| 6,183,443 B1 | 2/2001 | Kratoska et al. |
| 6,206,870 B1 | 3/2001 | Kanner |
| 6,506,179 B1 | 1/2003 | Tiefenthal et al. |
| 6,662,804 B2 | 12/2003 | Ortiz |
| 6,679,871 B2 | 1/2004 | Hahnen |
| 6,745,773 B1 | 6/2004 | Gobel |
| 6,951,555 B1 | 10/2005 | Suresh et al. |
| 6,989,009 B2 | 1/2006 | Lafontaine |
| 7,144,386 B2 | 12/2006 | Korkor et al. |
| 7,341,061 B2 | 3/2008 | Wood |
| 7,361,168 B2 | 4/2008 | Makower et al. |
| 7,410,480 B2 | 8/2008 | Muni et al. |
| 7,419,497 B2 | 9/2008 | Muni et al. |
| 7,462,175 B2 | 12/2008 | Chang et al. |
| 7,500,971 B2 | 3/2009 | Chang et al. |
| 7,520,876 B2 | 4/2009 | Ressemann et al. |
| 7,534,250 B2 | 5/2009 | Schaeffer et al. |
| 7,559,925 B2 | 7/2009 | Goldfarb et al. |
| 7,591,830 B2 | 9/2009 | Rutter |
| 7,645,272 B2 | 1/2010 | Chang et al. |
| 7,654,997 B2 | 2/2010 | Makower et al. |
| 7,678,099 B2 | 3/2010 | Ressemann et al. |
| 7,717,933 B2 | 5/2010 | Becker |
| 7,720,521 B2 | 5/2010 | Chang et al. |
| 7,727,186 B2 | 6/2010 | Makower et al. |
| 7,727,226 B2 | 6/2010 | Chang et al. |
| 7,740,642 B2 | 6/2010 | Becker |
| 7,753,929 B2 | 7/2010 | Becker |
| 7,753,930 B2 | 7/2010 | Becker |
| 7,771,409 B2 | 8/2010 | Chang et al. |
| 7,771,446 B2 | 8/2010 | Rutter |
| 7,803,150 B2 | 9/2010 | Chang et al. |
| 7,849,857 B2 | 12/2010 | Gobel |
| 7,854,744 B2 | 12/2010 | Becker |
| 7,879,061 B2 | 2/2011 | Keith et al. |
| 7,918,871 B2 | 4/2011 | Truitt et al. |
| 8,038,598 B2 | 10/2011 | Khachi |
| 8,088,101 B2 | 1/2012 | Chang et al. |
| 8,090,433 B2 | 1/2012 | Makower et al. |
| 8,100,933 B2 | 1/2012 | Becker |
| 8,114,062 B2 | 2/2012 | Muni et al. |
| 8,123,722 B2 | 2/2012 | Chang et al. |
| 8,142,412 B2 | 3/2012 | Hehrlein et al. |
| 8,142,422 B2 | 3/2012 | Makower et al. |
| 8,151,798 B2 | 4/2012 | Thomas et al. |
| 8,152,832 B2 | 4/2012 | Beulke et al. |
| 8,231,600 B2 | 7/2012 | von Hoffmann |
| 8,241,266 B2 | 8/2012 | Keith et al. |
| 8,277,478 B2 | 10/2012 | Drontle et al. |
| 8,282,667 B2 | 10/2012 | Drontle et al. |
| 8,307,830 B2 | 11/2012 | Clayton |
| 8,317,816 B2 | 11/2012 | Becker |
| 8,388,642 B2 | 3/2013 | Muni et al. |
| 8,414,473 B2 | 4/2013 | Jenkins et al. |
| 8,424,534 B2 | 4/2013 | Lyons et al. |
| 8,425,457 B2 | 4/2013 | John et al. |
| 8,435,290 B2 | 5/2013 | Clifford et al. |
| 8,740,843 B2 | 6/2014 | Eaton et al. |
| 8,771,257 B2 | 7/2014 | Hoffman |
| 8,899,225 B2 | 12/2014 | Bosel |
| 8,911,399 B2 | 12/2014 | Boatman |
| 9,132,260 B2 | 9/2015 | Schaeffer et al. |
| 9,192,747 B2 | 11/2015 | Hardert |
| 2005/0119613 A1 | 6/2005 | Moenning et al. |
| 2005/0224079 A1 | 10/2005 | Green |
| 2006/0135981 A1 | 6/2006 | Lenker et al. |
| 2006/0259061 A1 | 11/2006 | Kick et al. |
| 2007/0129751 A1 | 6/2007 | Muni et al. |
| 2007/0167682 A1 | 7/2007 | Goldfarb et al. |
| 2007/0208252 A1 | 9/2007 | Makower |
| 2007/0293727 A1 | 12/2007 | Goldfarb et al. |
| 2008/0015721 A1 | 1/2008 | Ressemann et al. |
| 2008/0015544 A1 | 1/2008 | Keith et al. |
| 2008/0078405 A1* | 4/2008 | Crumback ............ A61M 16/04 128/207.15 |
| 2008/0103521 A1 | 5/2008 | Makower et al. |
| 2008/0119693 A1 | 5/2008 | Makower et al. |
| 2008/0132938 A1 | 6/2008 | Chang et al. |
| 2008/0172033 A1 | 7/2008 | Keith et al. |
| 2008/0195041 A1 | 8/2008 | Goldfarb et al. |
| 2008/0228085 A1 | 9/2008 | Jenkins et al. |
| 2008/0275483 A1 | 11/2008 | Makower et al. |
| 2008/0287908 A1 | 11/2008 | Muni et al. |
| 2008/0319424 A1 | 12/2008 | Muni et al. |
| 2009/0030274 A1 | 1/2009 | Goldfarb et al. |
| 2009/0187098 A1 | 7/2009 | Makower et al. |
| 2009/0198216 A1 | 8/2009 | Muni et al. |
| 2009/0216196 A1 | 8/2009 | Drontle et al. |
| 2009/0240112 A1 | 9/2009 | Goldfarb et al. |
| 2009/0240199 A1 | 9/2009 | Rahimsobhani |
| 2009/0240237 A1 | 9/2009 | Goldfarb et al. |
| 2009/0312745 A1 | 12/2009 | Goldfarb et al. |
| 2010/0030113 A1 | 2/2010 | Morriss et al. |
| 2010/0042046 A1 | 2/2010 | Chang et al. |
| 2010/0076269 A1 | 3/2010 | Makower et al. |
| 2010/0114066 A1 | 5/2010 | Makower et al. |
| 2010/0168511 A1 | 7/2010 | Muni et al. |
| 2010/0174138 A1 | 7/2010 | Chang et al. |

(56) References Cited

U.S. PATENT DOCUMENTS

| | | |
|---|---|---|
| 2010/0174308 A1 | 7/2010 | Chang et al. |
| 2010/0198191 A1 | 8/2010 | Clifford et al. |
| 2010/0198247 A1 | 8/2010 | Chang et al. |
| 2010/0211007 A1 | 8/2010 | Lesch, Jr. et al. |
| 2010/0268245 A1 | 10/2010 | Chang et al. |
| 2010/0274188 A1 | 10/2010 | Chang et al. |
| 2010/0298862 A1 | 11/2010 | Chang et al. |
| 2011/0004057 A1 | 1/2011 | Goldfarb et al. |
| 2011/0060214 A1 | 3/2011 | Makower |
| 2011/0071349 A1 | 3/2011 | Drontle et al. |
| 2011/0112512 A1 | 5/2011 | Muni et al. |
| 2011/0144690 A1 * | 6/2011 | Bishop ............... A61F 2/2433 606/195 |
| 2011/0160740 A1 | 6/2011 | Makower et al. |
| 2011/0224652 A1 | 9/2011 | Drontle et al. |
| 2011/0288477 A1 | 11/2011 | Ressemann et al. |
| 2012/0010646 A1 | 1/2012 | Keith et al. |
| 2012/0071824 A1 | 3/2012 | Chang et al. |
| 2012/0116254 A1 | 5/2012 | Morriss |
| 2012/0118286 A1 | 5/2012 | Barodka |
| 2012/0136207 A1 | 5/2012 | Goldfarb et al. |
| 2012/0172912 A1 | 7/2012 | Ressemann et al. |
| 2012/0184983 A1 | 7/2012 | Chang et al. |
| 2012/0190973 A1 | 7/2012 | Ressemann et al. |
| 2012/0245419 A1 | 9/2012 | Makower et al. |
| 2012/0265094 A1 | 10/2012 | Goldfarb et al. |
| 2012/0283625 A1 | 11/2012 | Keith et al. |
| 2012/0303011 A1 | 11/2012 | Schaeffer |
| 2013/0096605 A1 | 4/2013 | Becker |
| 2013/0178790 A1 | 7/2013 | Tekulve |
| 2013/0226146 A1 | 8/2013 | Tekulve |
| 2013/0245662 A1 | 9/2013 | Schaeffer et al. |
| 2014/0031792 A1 | 1/2014 | Darin et al. |
| 2014/0039494 A1 | 2/2014 | Kick et al. |
| 2014/0088624 A1 | 3/2014 | Burton et al. |
| 2014/0100592 A1 | 4/2014 | Burton et al. |
| 2014/0121670 A1 | 5/2014 | Bishop et al. |
| 2014/0276714 A1 | 9/2014 | Edmunds et al. |
| 2014/0277066 A1 | 9/2014 | Schaeffer et al. |
| 2015/0073467 A1 | 3/2015 | Eaton |
| 2016/0030694 A1 | 2/2016 | Gingles et al. |

FOREIGN PATENT DOCUMENTS

| | | |
|---|---|---|
| EP | 2522386 | 11/2012 |
| WO | 9220399 | 11/1992 |
| WO | WO2006020180 | 2/2006 |
| WO | 2006029370 | 3/2006 |
| WO | WO2006/136964 | 12/2006 |
| WO | 2007057127 | 5/2007 |
| WO | WO2008045242 | 4/2008 |
| WO | WO2009/114425 | 9/2009 |
| WO | WO2010/024871 | 3/2010 |
| WO | WO2010/065030 | 6/2010 |
| WO | WO2011082074 | 7/2011 |
| WO | WO2011084655 | 7/2011 |
| WO | 2011096975 | 8/2011 |

OTHER PUBLICATIONS

European Patent Office, "Extended European Search Report," for Application No. 14160329.0, dated Aug. 22, 2014, pp. 1-7.

European Patent Office, Examination Report for European Application No. 14160329, dated Oct. 31, 2017, pp. 1-5.

* cited by examiner

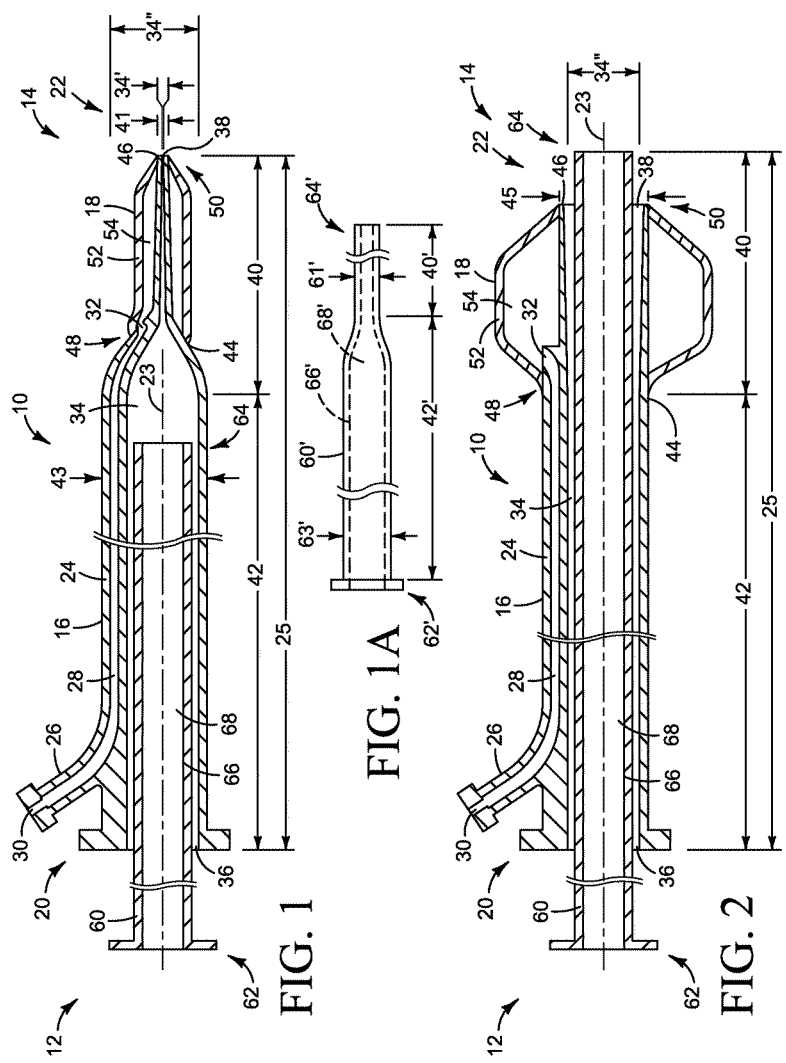

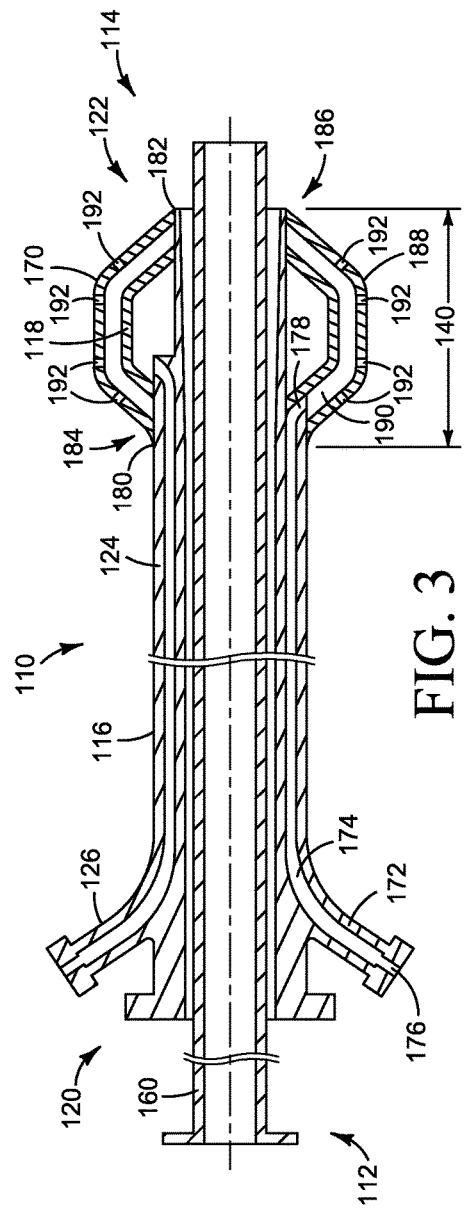
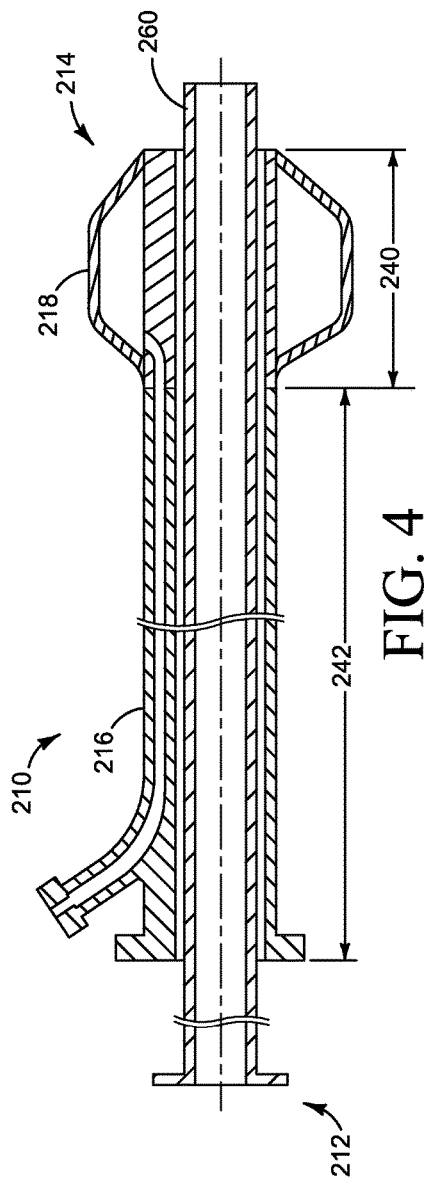

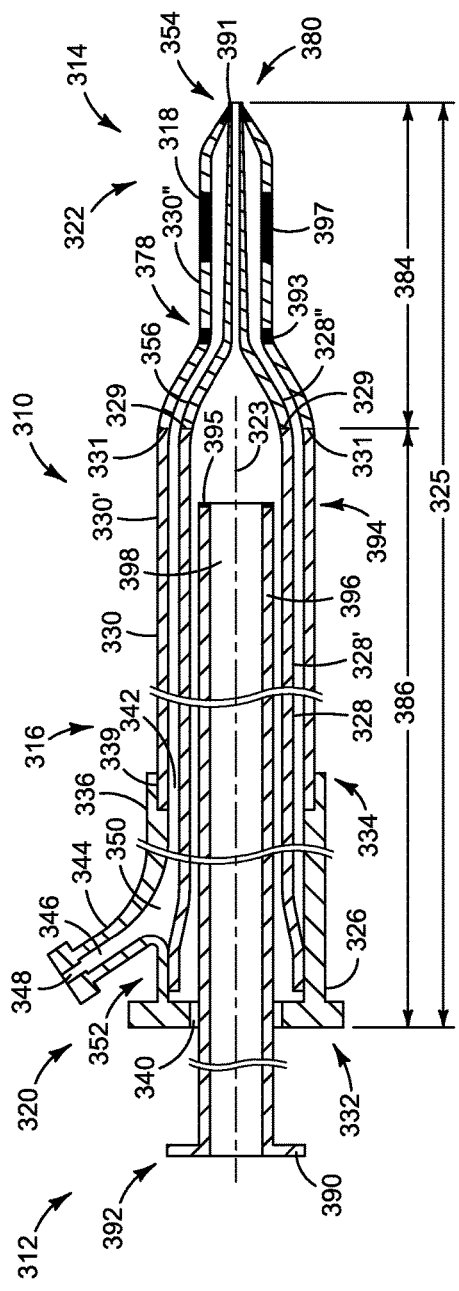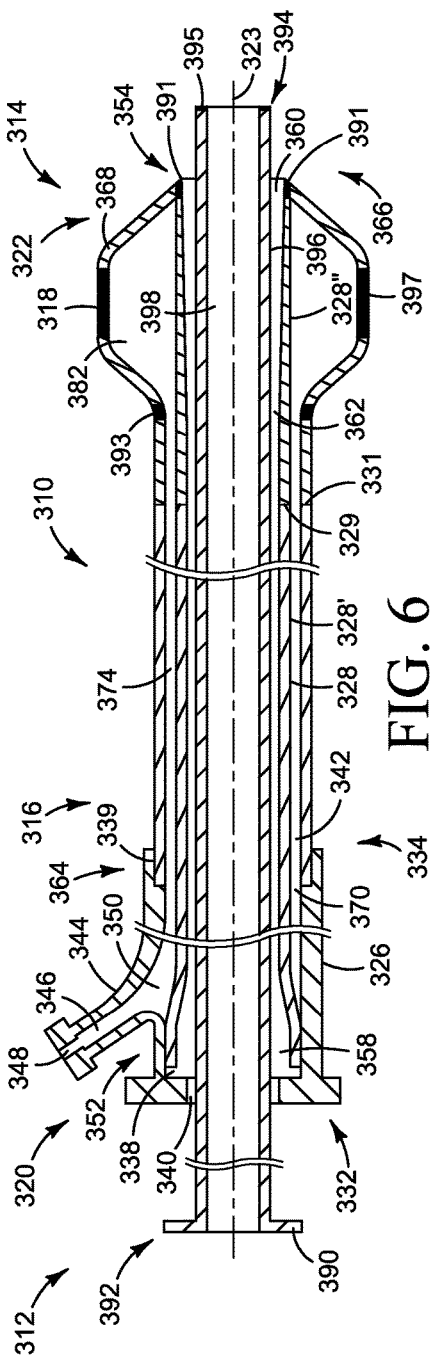
FIG. 5
FIG. 6

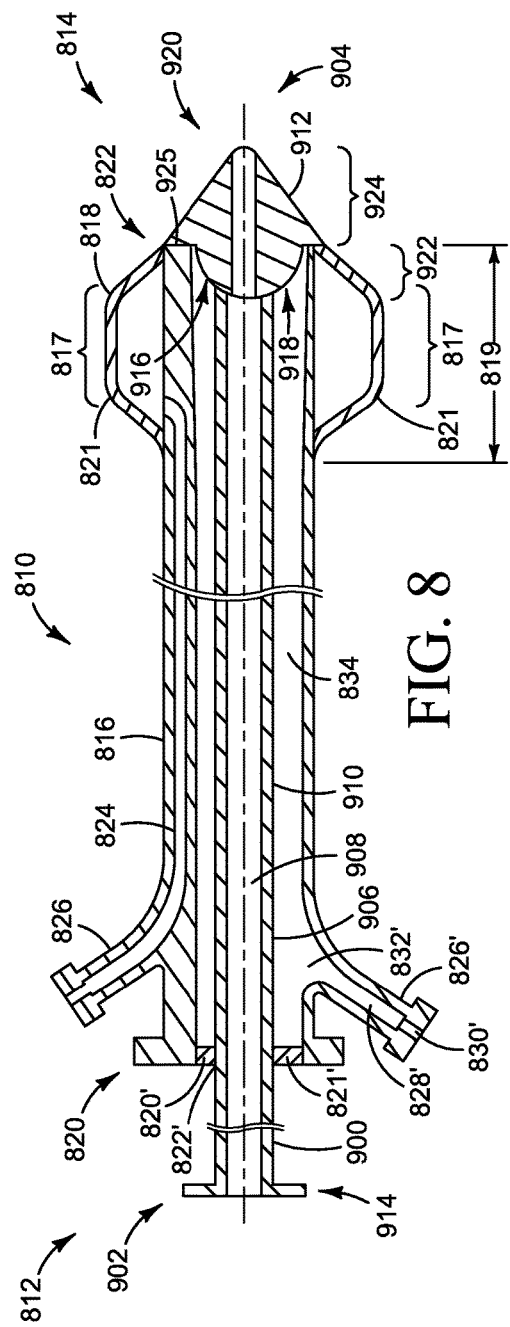
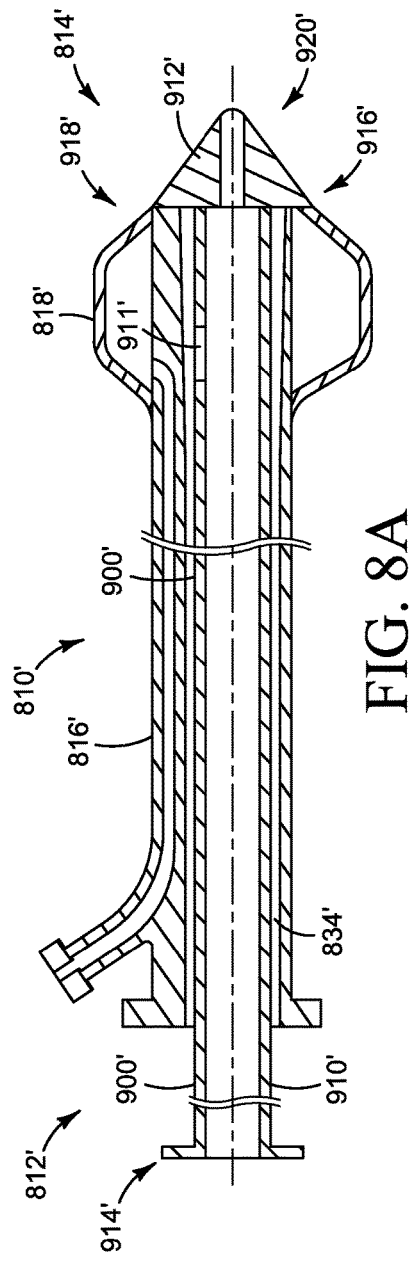
FIG. 8
FIG. 8A

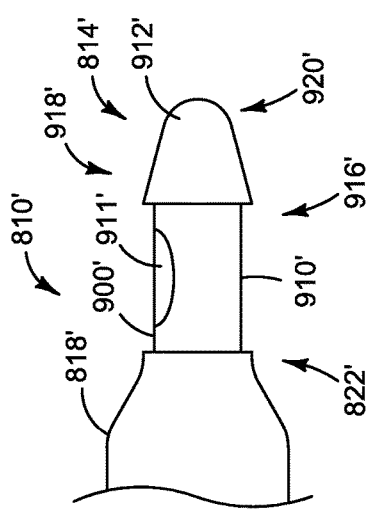
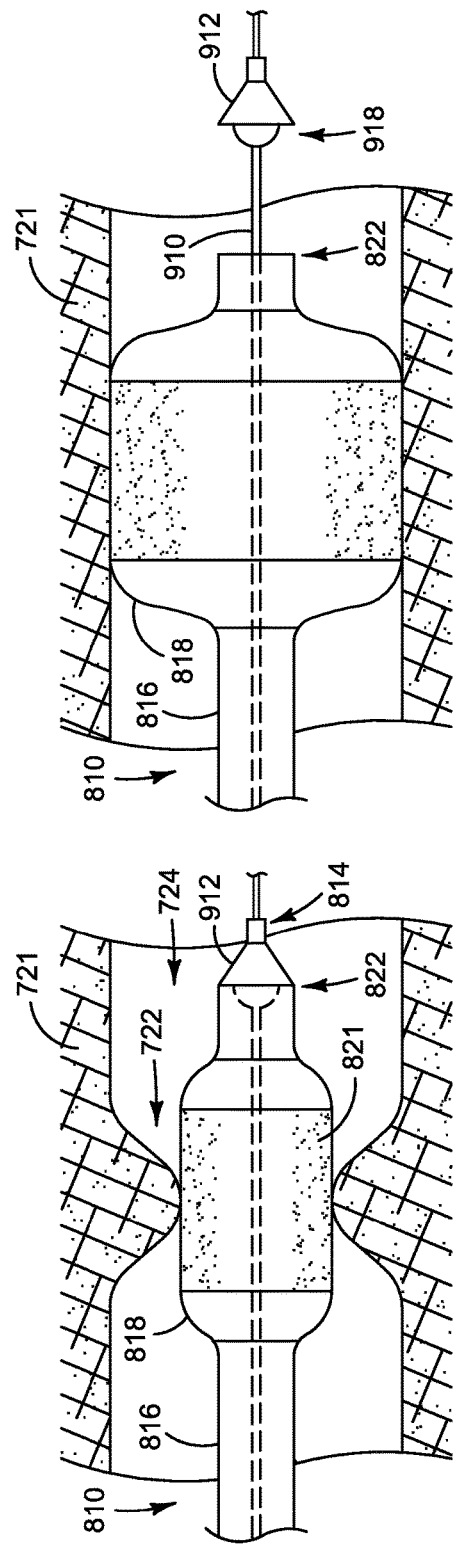
FIG. 8B
FIG. 9B
FIG. 9A

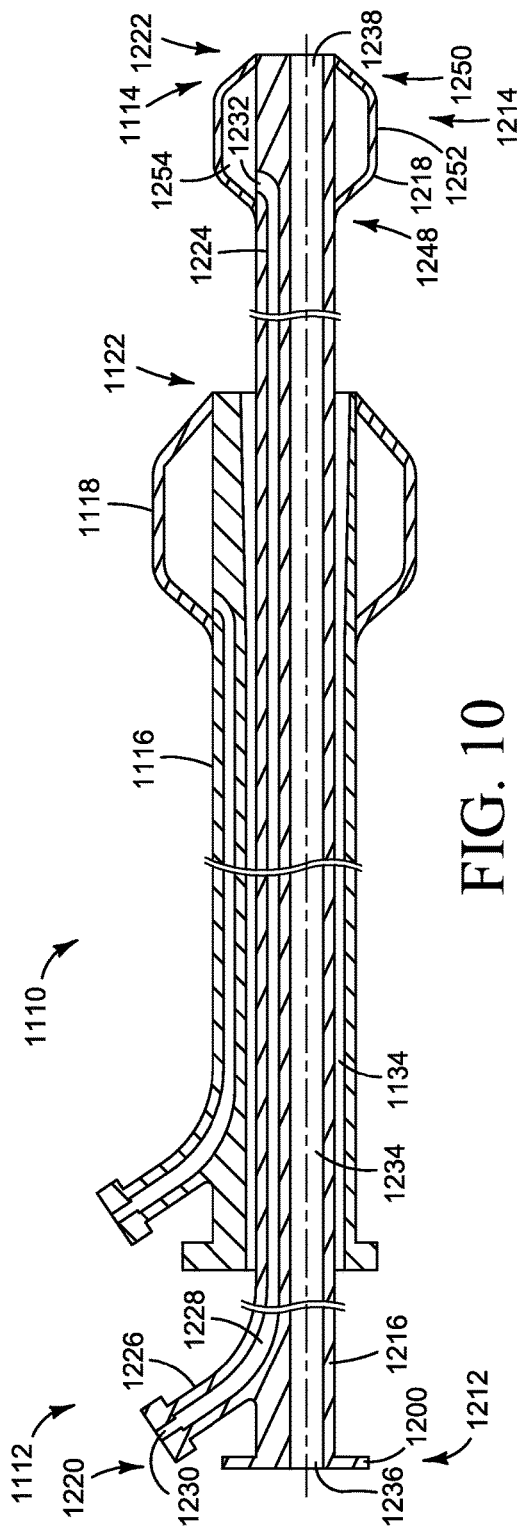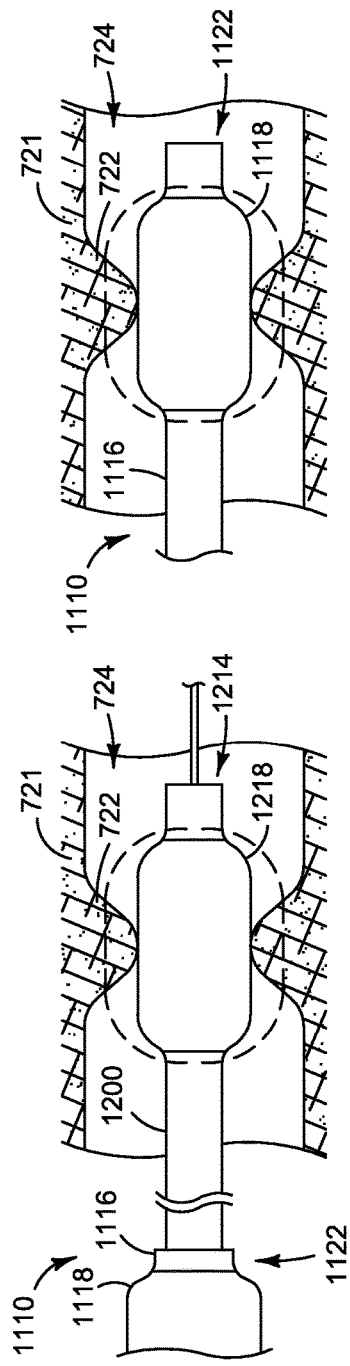
FIG. 10
FIG. 11A
FIG. 11B

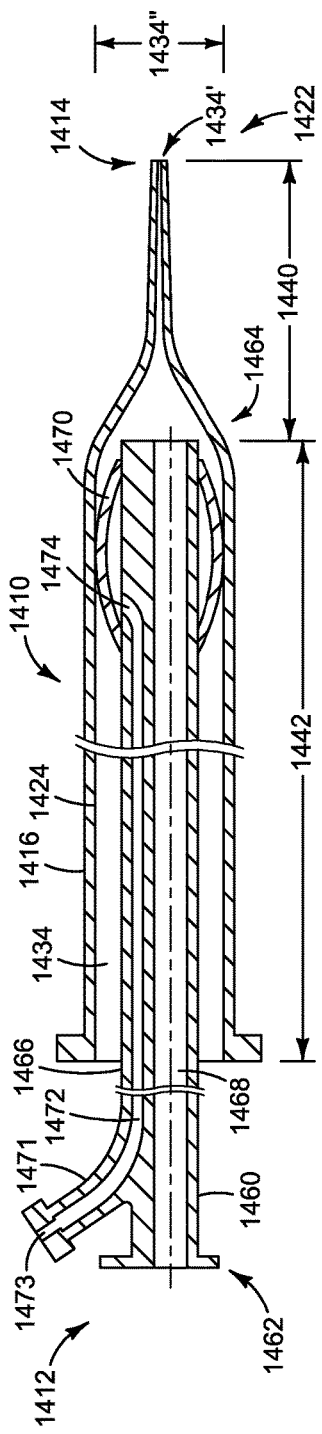
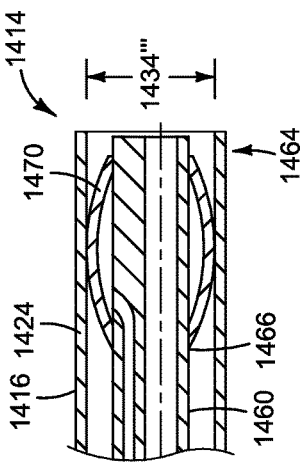
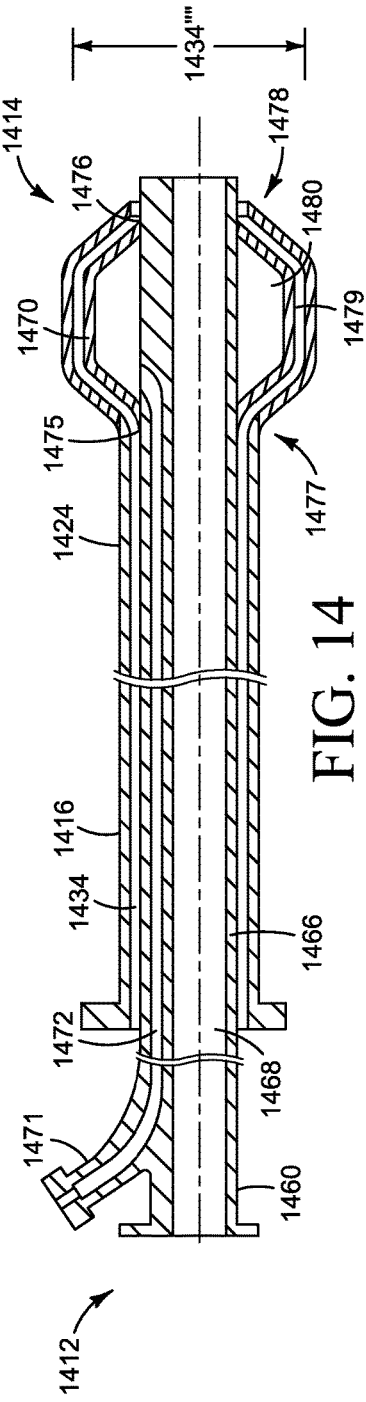
FIG. 12
FIG. 13
FIG. 14

MEDICAL DEVICES AND METHODS FOR PROVIDING ACCESS TO A BODILY PASSAGE DURING DILATION

RELATED APPLICATIONS

This application claims the benefit of U.S. Provisional Application No. 61/792,415, filed Mar. 15, 2013. The disclosure of this related application is hereby incorporated into this disclosure in its entirety.

FIELD

The invention relates generally to medical devices and methods of treatment. More particularly, the invention relates to medical devices and methods for providing access to a bodily passage, such as an airway, during dilation.

BACKGROUND

To treat stenosis—the narrowing of a bodily passage—physicians frequently dilate the bodily passage using a balloon catheter. For example, when functioning normally, the trachea allows air to pass from the pharynx and larynx to the lungs. However, when the trachea becomes obstructed, for example when a stricture forms within the trachea wall, the volume of air that can pass to and from the lungs is reduced. This results in respiratory complications, such as difficulty breathing, breathlessness, coughing, and wheezing.

To treat these conditions, physicians sometimes perform balloon dilation—the dilation of a bodily passage using a balloon catheter—to unblock the passage. Conventional dilation procedures advance a balloon catheter to a point of treatment and move the balloon to an inflated configuration to effectuate dilation and unblock the obstructed passage. However, these procedures are complicated due to the application of axial forces on the tissue forming the obstruction as the balloon catheter is advanced toward the point of treatment. This can result in damage to the tissue of the passage wall, which increases the trauma experienced by the patient during treatment. These procedures are also complicated due to the passage becoming blocked during dilation of the obstruction. For example, when treating a stricture formed in the wall of the trachea, the balloon catheter obstructs the airway when it is in the inflated configuration and prevents oxygen from passing to the lungs. Therefore, conventional procedures require the balloon to be inflated for short periods of time and then deflated multiple times so that oxygen saturation levels can be maintained, or restored, during treatment.

Therefore, a need exists for improved medical devices and methods for providing access to a bodily passage during dilation.

SUMMARY

Several exemplary medical devices and methods for providing access to a bodily passage during dilation are described herein.

An exemplary medical device comprises an elongate member and a balloon. The elongate member has an elongate member proximal end, an elongate member distal end, an elongate member axial length that extends from the elongate member proximal end to the elongate member distal end, a device lumen that extends through the elongate member, an inflation lumen, and an elongate member body that has a first wall thickness and a second wall thickness. A first portion of the elongate member axial length extends from the elongate member distal end toward the elongate member proximal end. A second portion of the elongate member axial length extends from the elongate member proximal end to the first portion of the elongate member axial length. The first wall thickness is disposed on the first portion of the elongate member axial length and the second wall thickness is disposed on the second portion of the elongate member axial length. The first wall thickness is less than the second wall thickness. The first portion of the elongate member axial length is adapted to move between a first, non-expanded configuration and a second, expanded configuration. The elongate member distal end has a first outside diameter when in the first, non-expanded configuration and a second outside diameter when in the second, expanded configuration. The second outside diameter is greater than the first outside diameter. The balloon is disposed on at least a portion of the first portion of the elongate member axial length. The balloon has a balloon chamber in communication with the inflation lumen and is adapted to move between a first, deflated configuration and a second, inflated configuration as fluid moves into and out of the balloon chamber.

Another exemplary medical device comprises an elongate member, a balloon, and a ventilation tube. The elongate member has an elongate member proximal end, an elongate member distal end, an elongate member axial length that extends from the elongate member proximal end to the elongate member distal end, a device lumen that extends through the elongate member, an inflation lumen, and an elongate member body that has a first wall thickness and a second wall thickness. A first portion of the elongate member axial length extends from the elongate member distal end toward the elongate member proximal end. A second portion of the elongate member axial length extends from the elongate member proximal end to the first portion of the elongate member axial length. The first wall thickness is disposed on the first portion of the elongate member axial length and the second wall thickness is disposed on the second portion of the elongate member axial length. The first wall thickness is less than the second wall thickness. The first portion of the elongate member axial length is adapted to move between a first, non-expanded configuration and a second, expanded configuration. The elongate member distal end has a first outside diameter when in the first, non-expanded configuration and a second outside diameter when in the second, expanded configuration. The second outside diameter is greater than the first outside diameter. The balloon is disposed entirely on the first portion of the elongate member axial length. The balloon has a balloon chamber in communication with the inflation lumen and is adapted to move between a first, deflated configuration and a second, inflated configuration as fluid moves into and out of the balloon chamber. The ventilation tube is partially disposed within the device lumen and comprises a ventilation tube proximal end, a ventilation tube distal end, and a ventilation tube body that defines a ventilation tube lumen.

An exemplary method of providing access to a bodily passage during dilation of a point of treatment within the bodily passage comprises the steps of: introducing a wire guide that has a wire guide proximal end and a wire guide distal into the bodily passage such that the wire guide distal end is disposed within the bodily passage; advancing the wire guide distal end distal to the point of treatment; introducing a medical device that has a medical device proximal end and a medical device distal end over the wire guide and into the bodily passage such that the medical device distal end is disposed within the bodily passage, the medical device comprising an elongate member, a balloon, and a ventilation tube; advancing the medical device distally over the wire guide and into the bodily passage such that the medical device distal end is disposed distal to the point of treatment; advancing the ventilation tube over the wire guide and through the device lumen such that the ventilation tube distal end is disposed distal to the elongate member distal end; passing fluid into the balloon chamber; removing a portion of the fluid from the balloon chamber; withdrawing the wire guide from the bodily passage; and withdrawing the medical device from the bodily passage.

Additional understanding of the exemplary medical devices and methods can be obtained by review of the detailed description, presented below, and the referenced drawings.

BRIEF DESCRIPTION OF THE DRAWINGS

FIG. 1 is a sectional view of an exemplary medical device in a first, non-expanded configuration with an associated balloon in a first, deflated configuration.

FIG. 1A is a side view of an alternative ventilation tube free of a medical device.

FIG. 2 is a sectional view of the medical device illustrated in FIG. 1 in a second, expanded configuration with the associated balloon in a second, inflated configuration.

FIG. 3 is a sectional view of a second exemplary medical device in a second, expanded configuration with an associated balloon in a second, inflated configuration.

FIG. 4 is a sectional view of a third exemplary medical device in a second, expanded configuration with an associated balloon in a second, inflated configuration.

FIG. 5 is a sectional view of a fourth exemplary medical device in a first, non-expanded configuration with an associated balloon in a first, deflated configuration.

FIG. 6 is a sectional view of the fourth exemplary medical device illustrated in FIG. 5 in a second, expanded configuration and the associated balloon in a second, inflated configuration.

FIG. 8 is a sectional view of a fifth exemplary medical device with an associated balloon in a second, inflated configuration.

FIG. 8A is a sectional view of a sixth exemplary medical device with an associated balloon in a second, inflated configuration.

FIG. 8B is a partial side view of the distal end of the medical device illustrated in FIG. 8A with an associated balloon in a second, inflated configuration. The dilator has been advanced distally through the device lumen.

FIG. 9A is a partial sectional view of a patient with a wire guide and the distal end of the medical device illustrated in FIG. 8 disposed in an airway. The balloon is in a first, deflated configuration.

FIG. 9B is a partial sectional view of a patient with a wire guide and the distal end of the medical device illustrated in FIG. 8 disposed in an airway. The dilator has been advanced distally within the airway and the balloon is in a second, inflated configuration.

FIG. 10 is a sectional view of a seventh exemplary medical device in a second, expanded configuration with an associated first balloon and second balloon. Each of the first balloon and the second balloon is in a second, inflated configuration.

FIG. 11A is a partial sectional view of a patient with a wire guide and the distal end of the medical device illustrated in FIG. 10 disposed in an airway. Each of first balloon and second balloon is in a first, deflated configuration.

FIG. 11B is a partial sectional view of a patient with the distal end of the medical device illustrated in FIG. 10 disposed in an airway. The dilator and the wire guide have been withdrawn from the device lumen and the first balloon is in a first, deflated configuration.

FIG. 12 is a sectional view of an eighth exemplary medical device in a first, non-expanded configuration with an associated balloon in a first, deflated configuration.

FIG. 13 is a partial sectional view of the medical device illustrated in FIG. 12 in a second, expanded configuration and the associated balloon in a first, deflated configuration.

FIG. 14 is a sectional view of the medical device illustrated in FIG. 12 in a second, expanded configuration with the associated balloon in a second, inflated configuration.

DETAILED DESCRIPTION

Figure 7:
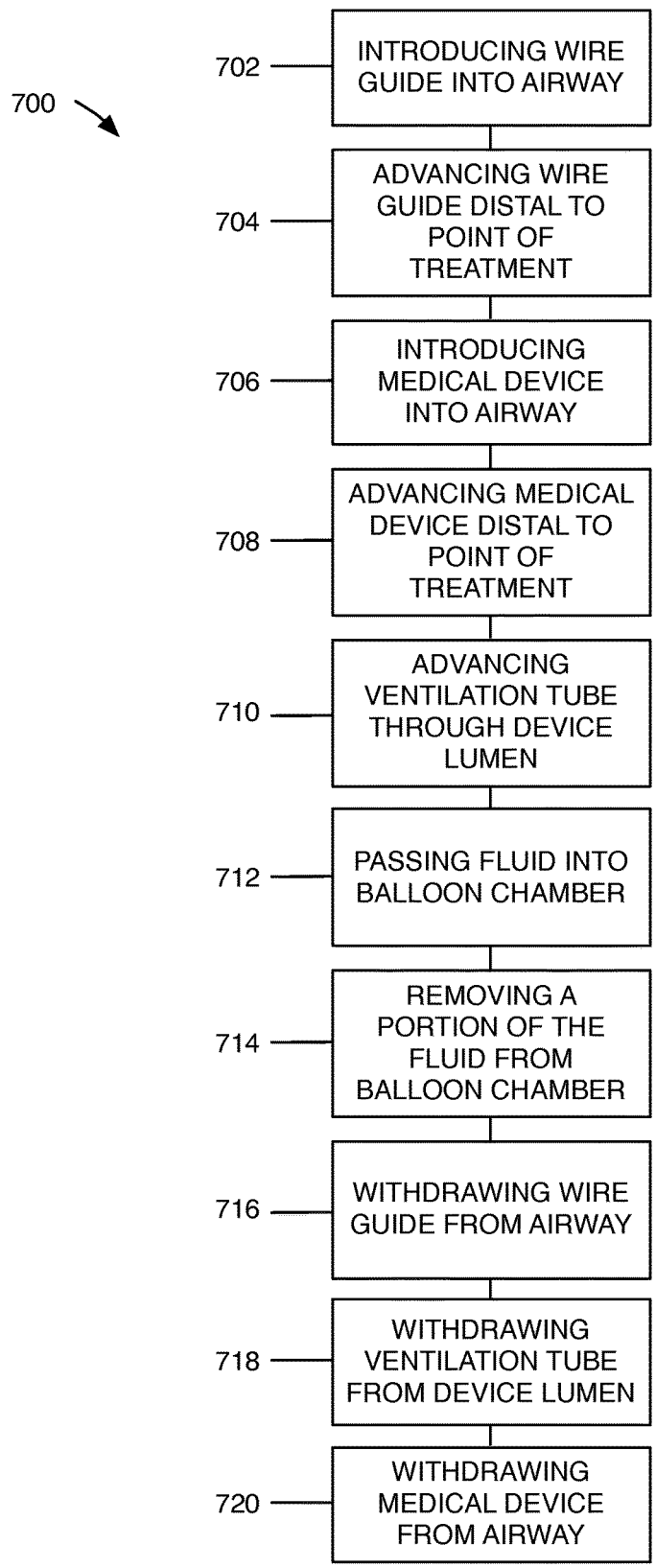
FIG. 7 is a flowchart representation of an exemplary method of providing access to a bodily passage during dilation.
Figure 7B:
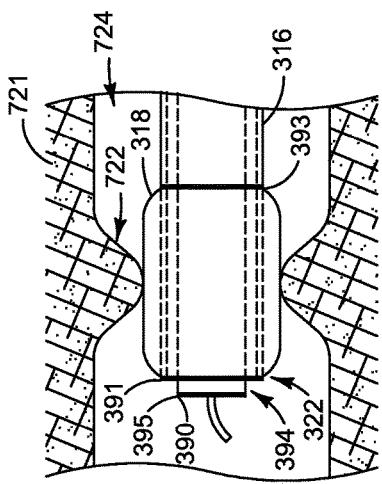
FIG. 7B is a partial sectional view of an airway with a wire guide, the distal end of the medical device illustrated in FIG. 5, and the distal end of a ventilation tube disposed in the airway. The medical device is in a second, expanded configuration and the associated balloon is in a first, deflated configuration.

The following detailed description and the appended drawings describe and illustrate various exemplary medical devices and methods. The description and drawings are exemplary in nature and are provided to enable one skilled in the art to make and use one or more exemplary medical devices and/or practice one or more exemplary methods. They are not intended to limit the scope of the claims in any manner.

The use of "e.g.," "etc.," "for instance," "in example," and "or" and grammatically related terms indicate non-exclusive alternatives without limitation, unless otherwise noted. The use of "optionally" and grammatically related terms means that the subsequently described element, event, feature, or circumstance may or may not be present or occur, and that the description includes instances where said element, event, feature, or circumstance occurs and instances where it does not. The use of "exemplary" refers to "an example of" and is not intended to convey a meaning of an ideal or preferred embodiment. The use of "attached" refers to the fixed, releasable, or integrated association of two or more elements and/or devices. Thus, the term "attached" includes releasably attaching or fixedly attaching two or more elements and/or devices. The term "medication" refers to any fluid, drug, agent, therapeutic agent, and/or any other material used to treat a patient. As used herein, the terms "proximal" and "distal" are used to describe opposing axial ends of the particular element or feature being described. The term "bodily passage" or "body passage" refers to any passage within the body of an animal, including, but not limited to, humans, and includes elongate passages. The term "airway" refers to any airway including, but not limited to, the nasopharynx, oropharynx, pharynx, larynx, trachea, bronchial tubes, esophagus, and/or lungs.

FIGS. 1 and 2 illustrate an exemplary medical device 10 having a medical device proximal end 12 and medical device distal end 14 and comprising an elongate member 16, balloon 18, and ventilation tube 60. Medical device 10 is adapted to move between a first, non-expanded configuration and a second, expanded configuration, as described in more detail herein.

Elongate member 16 can have any suitable outside diameter and length, and skilled artisans will be able to select a suitable outside diameter and length for an elongate member according to a particular embodiment based on various considerations, including the desired bodily passage within which the medical device is intended to be used.

Elongate member 16 can be formed of any suitable material, and skilled artisans will be able to select a suitable material for an elongate member according to a particular embodiment based on various considerations, including the desired flexibility of the elongate member. Example materials considered suitable to form an elongate member include, but are not limited to, biocompatible materials, materials that can be made biocompatible, metals such as stainless steel, titanium, nickel-titanium alloys (e.g., Nitinol), polymers, Pebax (Pebax is a registered trademark of Ato Chimie Corporation of Allee des Vosges, Courbevoie, France), nylon, polyethylene, polyurethane, polytetrafluoroethylene (PTFE), ePTFE, silicone, coiled materials, braided materials, and any other material considered suitable for a particular application.

In the illustrated embodiment, elongate member 16 is adapted to move between a first, non-expanded configuration and a second, expanded configuration and comprises an elongate member proximal end 20, elongate member distal end 22, elongate member lengthwise axis 23, elongate member body 24, and an elongate member axial length 25. Elongate member body 24 defines an inflation port 26, inflation lumen 28, first inflation lumen opening 30, second inflation lumen opening 32, device lumen 34, first device lumen opening 36, and a second device lumen opening 38.

Inflation port 26 is disposed on a proximal portion of elongate member 16 and inflation lumen 28 extends from first inflation lumen opening 30 defined on inflation port 26 to second inflation lumen opening 32 defined between elongate member proximal end 20 and elongate member distal end 22. Device lumen 34 extends from first device lumen opening 36 defined on elongate member proximal end 20 to second device lumen opening 38 defined on elongate member distal end 22.

Device lumen 34 can have any suitable inside diameter, and skilled artisans will be able to select a suitable diameter for a device lumen according to a particular embodiment based on various considerations, including the treatment intended to be performed. The inventors have determined that device lumens having an inside diameter between about 1 millimeter to about 8 millimeters are considered suitable. The inventors have also determined that device lumens having an inside diameter between about 3 millimeters to about 6 millimeters are considered suitable. The inventors have also determined that device lumens having an inside diameter between about 2.5 millimeters to about 4 millimeters are considered suitable. The inside diameter of a device lumen can be based on the anatomy of a patient. For example, in instances in which the patient is a newborn, a device lumen can have an inside diameter that is about 2.5 millimeters. Alternatively, in instances in which the patient is a toddler, a device lumen can have an inside diameter that is between about 2.5 millimeters and about 4 millimeters. Alternatively, in instances in which the patient is an adult, a device lumen can have an inside diameter that is between about 4 millimeters and about 8 millimeters.

In the illustrated embodiment, elongate member 16 has a first portion of elongate member axial length 40 that extends from elongate member distal end 22 toward elongate member proximal end 20 and a second portion of elongate member axial length 42 that extends from elongate member proximal end 20 to the first portion of elongate member axial length 40. Thus, elongate member first portion 40 extends from elongate member distal end 22 toward elongate member proximal end 20 a distance that is less than elongate member axial length 25.

First portion of elongate member axial length 40 is adapted to move between a first, non-expanded configuration and a second, expanded configuration. FIG. 1 illustrates first portion of elongate member axial length 40 in the first, non-expanded configuration and FIG. 2 illustrates first portion of elongate member axial length 40 in the second, expanded configuration. In the first, non-expanded configuration, a portion, or the entirety, of elongate member 16 that extends along first portion of elongate member axial length 40 (e.g., elongate member distal end 22) has a first outside diameter 41 and a portion, or the entirety, of elongate member 16 that extends along second portion of elongate member axial length 42 (e.g., elongate member proximal end 20) has a second outside diameter 43. The first diameter 41 of first portion of elongate member axial length 40 is less than the second diameter 43 of second portion of elongate member axial length 42. Thus, in the first, non-expanded configuration, device lumen 34 has a first inside diameter 34' along a portion, or the entirety, of first portion of elongate member axial length 40 that is less than a second inside diameter 34" of device lumen 34 along a portion, or the entirety, of second portion elongate member axial length 42. Each of the first diameter 41 of first portion of elongate member axial length 40 and the second diameter 43 of second portion of elongate member axial length 42 can be measured along a plane that extends orthogonal, or substantially orthogonal, to elongate member lengthwise axis 23. Optionally, the first inside diameter 34' of a device lumen can equal 0, such that the elongate member distal end 22 is closed.

In the second, expanded configuration, a portion, or the entirety, of elongate member 16 that extends along first portion of elongate member axial length 40 (e.g., elongate member distal end 22) has a third outside diameter 45 and a portion, or the entirety, of elongate member 16 that extends along second portion of elongate member axial length 42 has the second outside diameter 43. The third diameter 45 of first portion of elongate member axial length 40 is greater than the first diameter 41 of first portion of elongate member axial length 40 and is equal to, or substantially equal to, the second diameter 43 of second portion of elongate member axial length 42. Thus, in the second, expanded configuration, device lumen 34 has a third inside diameter 34''' along a portion, or the entirety, of first portion of elongate member axial length 40 that is greater than the first inside diameter 34' of device lumen 34 and is equal to, or substantially equal to, the second inside diameter 34" of device lumen 34. Alternatively, the third diameter 45 can be greater than, or less than, the second diameter 43 of the second portion of the elongate member axial length 42 and/or the third inside diameter 34''' can be greater than, or less than, the second inside diameter 34" of device lumen 34. Each of the third diameter 45 of first portion of elongate member axial length 40 and the second diameter 43 of second portion of elongate member axial length 42 can be measured along a plane that extends orthogonal, or substantially orthogonal, to elongate member lengthwise axis 23.

Elongate member 16 can have any suitable structure to accomplish movement between a first, non-expanded configuration and a second, expanded configuration. In the illustrated embodiment, elongate member body 24 has a first wall thickness along the first portion of elongate member axial length 40 and a second wall thickness along the second portion of elongate member axial length 42. In the embodiment illustrated, the first wall thickness is less than the second wall thickness. Thus, the first portion of elongate member axial length 40 is flexible, or substantially flexible, relative to the second portion of elongate member axial length 42 (e.g., the first portion of elongate member axial length 40 is more flexible than the second portion of elongate member axial length 42, the first portion of elongate member axial length 40 is relatively more flexible than the second portion of elongate member axial length 42).

While a particular structural arrangement has been illustrated and described to accomplish an elongate member 16 that is moveable between a first, non-expanded configuration and a second, expanded configuration, any suitable structural arrangement capable of accomplishing movement between a non-expanded configuration and an expanded configuration is considered suitable. Skilled artisans will be able to select a suitable structural arrangement for an elongate member according to a particular embodiment based on various considerations, including the materials that form the elongate member. Example structural arrangements considered suitable for an elongate member include, but are not limited to, a first portion of an elongate member axial length comprising a first durometer hardness and a second portion of an elongate member axial length comprising a second durometer hardness that is greater than the first durometer hardness, a first portion of an elongate member axial length comprising a first material (e.g., radially expandable material, ePTFE) and a second portion of an elongate member axial length comprising a second material that is different from the first material (e.g., rigid relative to the first material, not expandable relative to the first material), a first portion of an elongate member axial length comprising a first material and a second portion of an elongate member axial length comprising a second material that is rigid, or substantially rigid, relative to the first material (e.g., first material is flexible, or substantially flexible, relative to the second material, first material is more flexible than the second material, first material is relatively more flexible than the second material), a first portion of an elongate member axial length comprising a material having a first thickness and a second portion of an elongate member axial length comprising a second material having a second thickness that is greater than the first thickness, an inner member formed of a first material and an outer lumen formed of a second material, the second material the same as, or different from, the first material, folding a first portion (e.g., first portion of elongate member axial length), or the entirety, of an elongate member axial length, folding only a first portion (e.g., first portion of elongate member axial length) of an elongate member axial length, incorporating pleats into a portion (e.g., first portion of elongate member axial length), or the entirety of, an elongate member axial length, wrapping a first portion (e.g., first portion of elongate member axial length), or the entirety, of an elongate member axial length, and any other structural arrangements considered suitable for a particular application, including combinations of those described above.

In addition, first portion of elongate member axial length 40 can comprise any suitable length of elongate member axial length 25 and second portion of elongate member axial length 42 can comprise any suitable length of elongate member axial length 25. For example, a first portion of an elongate member axial length and/or a second portion of an elongate member axial length can comprise 5%, 10%, 20%, 25%, 30%, 40%, 50%, 60%, 70%, or 75% of an elongate member axial length. It is considered advantageous for a first portion of an elongate member axial length to have a length along the elongate member axial length that is less than the length of a second portion of an elongate member axial length along the elongate member axial length.

Movement of elongate member 16 between the first, non-expanded configuration and the second, expanded configuration can be accomplished by displacing the elongate member 16 in any suitable direction using another device, such as ventilation tube 60 and/or dilator (e.g., dilator 1870). Skilled artisans will be able to select a suitable direction to displace an elongate member via movement of another device according to a particular embodiment based on various considerations, including the treatment intended to be performed. Example directions considered suitable to displace an elongate member (e.g., first portion of an elongate member axial length) via movement of another device include, but are not limited to, radially, along a plane, along a portion of a surface, and any other direction considered suitable for a particular application.

While first portion of elongate member axial length 40 has been illustrated as extending from elongate member distal end 22 toward elongate member proximal end 20 a distance that is less than elongate member axial length 25, a first portion of an elongate member axial length can extend any suitable distance along an elongate member axial length. Skilled artisans will be able to select a suitable distance according to a particular embodiment based on various considerations, including the material that forms an elongate member. Example distances considered suitable for a first portion of an elongate member axial length to extend along an elongate member axial length include, but are not limited to, from an elongate member distal end to an elongate member proximal end, from an elongate member distal end toward an elongate member proximal end a distance that is less than the elongate member axial length, and any other distance considered suitable for a particular application.

First portion of an elongate member axial length 40 and second portion of an elongate member axial length 42 can be formed using any suitable material and/or technique. Skilled artisans will be able to select a suitable material and/or technique to form an elongate member according to a particular embodiment based on various considerations, including the bodily passage intended to be treated. Example materials and techniques considered suitable to form an elongate member include, but are not limited to, forming a first portion of an elongate member axial length of a material having a first durometer hardness and a second portion of an elongate member axial length of a material having a second durometer hardness that is greater than the first durometer hardness, forming a first portion of an elongate member axial length of a first material and a second portion of an elongate member axial length of a second material that is different from the first material, forming a first portion of an elongate member axial length of a first material that is flexible relative to a second material forming a second portion of an elongate member axial length, forming a first portion of an elongate member axial length of a material having a first thickness and forming a second portion of an elongate member axial length of a second material, which can be different or the same as the first material, having a second thickness that is greater than the first thickness, and any other method and/or technique considered suitable for a particular application, including combinations of those described above.

Elongate member 16 can optionally include one or more stiffening elements disposed within the body, or on a surface, of elongate member 16 to advantageously increase the rigidity of elongate member 16 and to facilitate efficient advancement of elongate member 16 towards a point of treatment (e.g., through a stricture). Any suitable stiffening member can be disposed within, on the exterior surface of, or on the interior surface of, the body of an elongate member and along the entire length, or a portion of the length (e.g., first portion of elongate member axial length 40), of the elongate member. Skilled artisans will be able to select a suitable stiffening member to include on an elongate member according to a particular embodiment based on various considerations, including the desired rigidity and/or malleability of the elongate member. An example stiffening member considered suitable to include on an elongate member includes, but is not limited to, an elongate rod formed of a flexible and/or malleable material, such as nickel titanium (e.g., nitinol) or stainless steel.

Inflation port 26 and/or elongate member proximal end 20 can optionally include any suitable connector and/or adapter capable of attaching one or more devices to elongate member 16. Skilled artisans will be able to select a suitable connector and/or adapter to include on an inflation port and/or elongate member proximal end according to a particular embodiment based on various considerations, including the materials that form the elongate member. Example connectors and/or adapters considered suitable to include on an inflation port and/or elongate member proximal end include, but are not limited to, threaded connectors, Tuohy Borst adapters, luer lock connectors, and any other connector and/or adapter considered suitable for a particular application.

While elongate member 16 has been illustrated as having a bifurcated structural configuration defining an inflation port, inflation lumen, and device lumen, an elongate member can have any suitable structural configuration defining any suitable number of ports and/or lumens. Skilled artisans will be able to select a suitable structural configuration and number of ports and/or lumens to include on an elongate member according to a particular embodiment based on various considerations, including the desired treatment intended to be performed. For example, alternative to having a bifurcated proximal portion defining an infusion port, as illustrated in FIGS. 1 and 2, an elongate member can comprise a straight, or substantially straight, elongate shaft that has a proximal end defining a first inflation lumen opening providing access to an inflation lumen and/or a first device lumen opening providing access to a device lumen. Example number of lumens and/or ports considered suitable to include on an elongate member include, but are not limited to, one, at least one, two, a plurality, three, four, five, and any other number considered suitable for a particular application.

Balloon 18 can be formed of any suitable material, and skilled artisans will be able to select a suitable material to form a balloon according to a particular embodiment based on various considerations, including the material(s) that form an elongate member. Example materials considered suitable to form a balloon include, but are not limited to, biocompatible materials, materials that can be made biocompatible, flexible materials, substantially flexible materials, polymers, Pebax (Pebax is a registered trademark of Ato Chimie Corporation of Allee des Vosges, Courbevoie, France), nylon, polyethylene, polyurethane, and any other material considered suitable for a particular application. Balloon 18 can comprise any suitable type of balloon, such as a compliant or non-compliant balloon.

In the illustrated embodiment, balloon 18 is attached to elongate member 16 between elongate member proximal end 20 and elongate member distal end 22 at balloon proximal junction 44 and balloon distal junction 46. Balloon 18 comprises a balloon proximal end 48, balloon distal end 50, and balloon body 52. Balloon body 52 and the portion of the exterior surface of elongate member 16 disposed within balloon 18 define balloon chamber 54 that is adapted to receive a fluid such that balloon 18 can be moved between a first, deflated configuration and second, inflated configuration. Balloon 18 is attached to elongate member 16 such that second inflation lumen opening 32 is in communication with balloon chamber 54. With this structural arrangement, balloon 18 is adapted to move between the first, deflated configuration and the second, inflated configuration as fluid is moved into and out of balloon chamber 54 via the inflation lumen 28 and second inflation lumen opening 32. FIG. 1 illustrates balloon 18 in the first, deflated configuration and FIG. 2 illustrates balloon 18 in the second, inflated configuration. Optionally, a balloon can be omitted from an elongate member.

Balloon 18 is attached to elongate member 16 such that each of balloon proximal end 48 and balloon distal end 50 is disposed on first portion of elongate member axial length 40. Thus, the entire axial length of balloon 18 is disposed on first portion of elongate member axial length 40. This structural arrangement is considered advantageous at least because it allows balloon 18 to be folded, or arranged, with elongate member 16 when it is in the first, non-expanded configuration, as described in more detail herein.

Balloon proximal junction 44 and balloon distal junction 46 can comprise any suitable method of attachment between elongate member 16 and balloon 18, and skilled artisans will be able to select a suitable method of attachment between a balloon and an elongate member according to a particular embodiment based on various considerations, including the materials that form the elongate member and balloon. Example methods of attachment considered suitable between an elongate member and a balloon include, but are not limited to, attachments formed by heat fusing, using adhesives, mechanical connections, and any other method considered suitable for a particular application.

A user inflates balloon 18 by introducing a fluid, such as saline, into inflation lumen 28 until the fluid passes through second inflation lumen opening 32 and into balloon chamber 54. The resulting pressure placed on the inner surface of balloon body 52 by the fluid causes balloon 18 to inflate and adopt the second, inflated configuration. To move balloon 18 to the first, deflated configuration, vacuum pressure can be applied to inflation lumen 28 to remove fluid located within balloon chamber 54 via second inflation lumen opening 32, resulting in balloon 18 collapsing and adopting the first, deflated configuration.

Additional structure can be attached to elongate member 16 (e.g., inflation port 26) to facilitate the inflation and deflation of balloon 18, as described above. For example, an inflation device, such as a syringe, can be operatively connected, or attached, to elongate member 16 (e.g., to elongate member inflation port 26) and adapted to move balloon 18 between the first, deflated configuration and second, inflated configuration. Any inflation device capable of facilitating inflation and deflation of a balloon is considered suitable, and skilled artisans will be able to select a suitable inflation device according to a particular embodiment based on various considerations, including the procedure intended to be performed. Example inflation devices considered suitable include, but are not limited to, manually operated inflation devices, syringes, electromechanical inflation devices, pumps, and any other device considered suitable for a particular application.

While balloon 18 has been illustrated as disposed on elongate member 16 such that each of balloon proximal end 48 and balloon distal end 50 is disposed on first portion of elongate member axial length 40, any suitable structural arrangement between a balloon and an elongate member can be utilized. Skilled artisans will be able to select a suitable structural arrangement between a balloon and an elongate member according to a particular embodiment based on various considerations, including the material(s) that form a balloon and/or elongate member. Example locations considered suitable to position a balloon on an elongate member include, but are not limited to, positioning a balloon on an elongate member such that the balloon distal end is attached to the elongate member distal end and the balloon proximal end is disposed between the elongate member proximal end and elongate member distal end (e.g., on first portion of elongate member axial length, on second portion of elongate member axial length), the balloon distal end is disposed on first portion of elongate member axial length and the balloon proximal end is disposed on second portion of elongate member axial length, the balloon distal end and the balloon proximal end are disposed on second portion of elongate member axial length, at least a portion of the balloon (e.g., a portion of the balloon axial length, balloon distal end) is disposed on first portion of elongate member axial length, and any other location considered suitable for a particular application.

When elongate member 16 is in the non-expanded configuration and balloon 18 is in the first, deflated configuration, balloon 18 can be structurally arranged with elongate member 16 in any suitable manner, and skilled artisans will be able to select a suitable structural arrangement between a balloon and an elongate member according to a particular embodiment based on various considerations, including the material(s) that forms a balloon and/or an elongate member. Example structural arrangements considered suitable between a balloon and an elongate member include, but are not limited to, folding a portion, or the entirety, of a balloon with the first portion of the elongate member axial length, folding only a portion of a balloon with a portion of the first portion of the elongate member axial length, wrapping a portion, or the entirety, of a balloon with the first portion of the elongate member axial length, and any other structural arrangement considered suitable for a particular application, including combinations of those described above.

In the illustrated embodiment, balloon 18 and first portion of elongate member axial length 40 have been folded, such as a conventional uninflated balloon. In the first, non-expanded configuration, medical device 10 has a first outside diameter at medical device distal end 14 and a second outside diameter at medical device proximal end 12. The first outside diameter is less than second outside diameter. In the second, expanded configuration, medical device 10 has a third outside diameter at medical device distal end 14 that is equal, or substantially equal, to the second outside diameter. Each of the first diameter, second diameter, and third diameter can be measured along a plane that is orthogonal, or substantially orthogonal, to elongate member lengthwise axis 23.

Movement of elongate member 16 from the first, non-expanded configuration to the second, expanded configuration can be accomplished by passing a suitable device through device lumen 34. In the embodiments described herein, any suitable device can be used and skilled artisans will be able to select a suitable device to advance through a device lumen according to a particular embodiment based on various considerations, including the treatment intended to be performed. Example devices considered suitable to pass through a device lumen include, but are not limited to, elongate members, ventilation tubes, suction catheters, balloon catheters, irrigation catheters, a camera and/or light source disposed on an elongate member, and any other device considered suitable for a particular application.

In the illustrated embodiment, a ventilation tube 60 has been passed through device lumen 34 to move elongate member 16 from the first, non-expanded configuration to the second, expanded configuration. Ventilation tube 60 comprises a ventilation tube proximal end 62, ventilation tube distal end 64, and a ventilation tube body 66 that defines a ventilation tube lumen 68 that extends through the length of ventilation tube 60. It is considered advantageous to pass a ventilation tube 60 through device lumen 34 such that ventilation can be provided during dilation of a bodily passage, as described in more detail herein.

FIG. 1 illustrates ventilation tube distal end 64 disposed proximal to first portion of elongate member axial length 40 and elongate member 16 in the first, non-expanded configuration. Thus, ventilation tube 60 is partially disposed within device lumen 34. FIG. 2 illustrates ventilation tube distal end 64 disposed distal to elongate member distal end 22 and elongate member 16 in the second, expanded configuration.

As ventilation tube 60 is axially advanced through device lumen 34, ventilation tube body 66 contacts elongate member body 24 and moves elongate member 16 from the first, non-expanded configuration to the second, expanded configuration. In the illustrated embodiment, as ventilation tube 60 is axially advanced through device lumen 34, ventilation tube body 66 contacts first portion of elongate member axial length 40 and moves elongate member 16 from the first, non-expanded configuration to the second, expanded configuration. It is considered advantageous for ventilation tube 60 to have an axial length that is greater than the axial length of elongate member 16 at least because when the ventilation tube proximal end 62 contacts the elongate member proximal end 20 the ventilation tube distal end 64 is disposed distal to elongate member distal end 22 or disposed distal to the balloon distal end 50. Thus, ventilation tube proximal end 62 creates a mechanical stop to the advancement of ventilation tube distal end 64 once the ventilation distal end is positioned distal to elongate member distal end 22 or disposed distal to the balloon distal end 50.

Ventilation tube 60 can be formed of any suitable material, and skilled artisans will be able to select a suitable material for a ventilation tube according to a particular embodiment based on various considerations, including the structural arrangement and/or material(s) that form first portion of elongate member axial length. Example materials considered suitable to form a ventilation tube include, but are not limited to, biocompatible materials, materials that can be made biocompatible, metals such as stainless steel, titanium, polymers, Pebax (Pebax is a registered trademark of Ato Chimie Corporation of Allee des Vosges, Courbevoie, France), nylon, polyethylene, polyurethane, silicone, coiled materials, braided materials, and any other material considered suitable for a particular application.

Ventilation tube 60 can have any suitable outside diameter and length, and skilled artisans will be able to select a suitable outside diameter and length for a ventilation tube according to a particular embodiment based on various considerations, including the desired bodily passage within which the medical device is intended to be used. It is considered advantageous for ventilation tube 60 to have an outside diameter that is equal to, substantially equal to, or less than the inner diameter of the second inside diameter 34" of device lumen 34 along a portion a portion, or the entirety, of second portion of elongate member axial length 42 when elongate member 16 is in the first, non-expanded configuration. It is also considered advantageous for ventilation tube 60 to have an axial length that is equal to, substantially equal to, or greater than elongate member axial length 25 such that ventilation tube distal end 64 can be advanced beyond, or distal to, elongate member distal end 22. The inventors have determined that ventilation tubes having ventilation tube lumens with an inside diameter between about 1 millimeters to about 8 millimeters are considered suitable. The inventors have also determined that ventilation tubes having ventilation tube lumens with an inside diameter between about 3 millimeters to about 6 millimeters are considered suitable. The inventors have also determined that ventilation tubes having ventilation tube lumens with an inside diameter between about 3 millimeters, or 2.5 millimeters, to about 4 millimeters are considered suitable. The inside diameter of a ventilation tube lumen can be based on the anatomy of a patient. For example, in instances in which the patient is a newborn, a ventilation tube lumen can have an inside diameter that is about 3 millimeters. Alternatively, in instances in which the patient is a toddler, a ventilation tube lumen can have an inside diameter that is between about 3 millimeters and about 4 millimeters. Alternatively, in instances in which the patient is an adult, a ventilation tube lumen can have an inside diameter that is between about 4 millimeters and about 8 millimeters.

For example, as illustrated in FIG. 1A illustrates an alternative ventilation tube 60' free of a medical device. Ventilation tube 60' is similar to ventilation tube 60 illustrated in FIGS. 1 and 2 and described above, except as detailed below. Reference numbers in FIG. 1A refer to the same structural element or feature referenced by the same number in FIGS. 1 and 2, offset by '. Thus, ventilation tube 60' has a ventilation tube proximal end 62', a ventilation tube distal end 64', and a ventilation tube body 66' that defines a ventilation tube lumen 68'.

In the illustrated embodiment, ventilation tube 60' has a first outside diameter 61' along a first portion of ventilation tube axial length 40' and a second outside diameter 63' along a second portion of ventilation tube axial length 42'. Thus, the ventilation tube 60' has a stepped configuration. The first portion of ventilation tube axial length 40' extends from the ventilation tube distal end 64' and towards the ventilation tube proximal end 62' and the second portion of ventilation tube axial length 42' extends from the first portion of ventilation tube axial length 40' to ventilation tube proximal end 62'. This structural arrangement is considered advantageous at least because the second portion of ventilation tube axial length 42' reduces the resistance to airflow during ventilation.

The first outside diameter 61' and second outside diameter 63' can comprise any suitable diameter, and skilled artisans will be able to select a suitable first outside diameter and second outside diameter for a ventilation tube according to a particular embodiment based on various considerations, including the desired airflow intended to be administered to a patient. Example first and second outside diameters considered suitable for a ventilation tube include, but are not limited to, a first outside diameter being less than a second outside diameter, a first outside diameter being greater than a second outside diameter, and any other diameters considered suitable for a particular application. The inventors have determined that ventilation tubes having a first outside diameter 61' between about 4 millimeters to about 8 millimeters and a second outside diameter 63' between about 4 millimeters and about 10 millimeters are considered suitable. In addition, the inventors have determined that ventilation tubes having a first outside diameter 61' between about 3 millimeters and about 6 millimeters and a second outside diameter 63' between about 4 millimeters and about 9 millimeters are considered suitable. Furthermore, the inventors have determined that ventilation tubes having a first outside diameter 61' between 3 millimeters and 5 millimeters and a second outside diameter 63' between 5 millimeters and 8 millimeters are considered suitable.

While ventilation tube 60 has been illustrated as having a particular structural configuration, a ventilation tube can have any suitable structural configuration, and skilled artisans will be able to select a suitable structural configuration for a ventilation tube according to a particular embodiment based on various considerations, including the bodily passage within which treatment is desired to be performed. Example structural arrangements considered suitable for a ventilation tube include, but are not limited to, round, a first portion and/or second portion being round, oval, a first portion and/or second portion being oval, oblong, a first portion and/or second portion being oblong, and any other structural configuration and/or geometric shape considered suitable for a particular application.

Ventilation tube proximal end 62 can include any suitable connector and/or adapter capable of attaching one or more devices to ventilation tube 60 (e.g., ventilator). Skilled artisans will be able to select a suitable connector and/or adapter to include on a ventilation tube proximal end according to a particular embodiment based on various considerations, including the material(s) that form the elongate member. Example connectors and/or adapters considered suitable to include on a ventilation tube proximal end include, but are not limited to, threaded connectors, Tuohy Borst adapters, luer lock connectors, airway connectors, conical connectors (e.g., cones, sockets), such as those described in document BS (British Standards) EN ISO 5356-1:2004, and any other connector and/or adapter considered suitable for a particular application.

It is considered advantageous to use medical device 10 when dilating a bodily passage, such an airway, at least because it provides a mechanism for advancing a device distal to, or beyond, an obstruction formed in the wall of the bodily passage while reducing, or eliminating, the shearing forces applied to the tissue forming the obstruction. It is also considered advantageous to use medical device 10 when dilating a bodily passage, such as an airway, at least because it provides a mechanism for providing access to the bodily passage while the bodily passage is being dilated.

While ventilation tube 60 has been illustrated and described as a component of medical device 10, a ventilation tube can optionally be omitted from a medical device and provided separately.

FIG. 3 illustrates a second exemplary medical device 110. Medical device 110 is similar to medical device 10 illustrated in FIGS. 1 and 2 and described above, except as detailed below. Reference numbers in FIG. 3 refer to the same structural element or feature referenced by the same number in FIGS. 1 and 2, offset by 100. Thus, medical device 110 has a medical device proximal end 112 and medical device distal end 114. In the illustrated embodiment, medical device 110 comprises an elongate member 116, first balloon 118, ventilation tube 160, and second balloon 170 and is adapted to move between a first, non-expanded configuration and a second, expanded configuration.

In the illustrated embodiment, elongate member body 124 defines an infusion port 172, infusion lumen 174, first infusion lumen opening 176, and second infusion lumen opening 178. Infusion lumen 174 extends from first infusion lumen opening 176 defined on infusion port 172 to second infusion lumen opening 178 defined between elongate member proximal end 120 and elongate member distal end 122.

In the illustrated embodiment, first balloon 118 is disposed within the second balloon 170 and second balloon 170 is attached to elongate member 116 between elongate member proximal end 120 and elongate member distal end 122 at second balloon proximal junction 180 and balloon distal junction 182. Second balloon 170 comprises a second balloon proximal end 184, second balloon distal end 186, and second balloon body 188. Second balloon 170 is attached to elongate member 116 such that each of second balloon proximal end 184 and second balloon distal end 186 is disposed on first portion of elongate member axial length 140. Second balloon body 188, the portion of the surface of elongate member 116 disposed within second balloon 188, and the portion of the exterior surface of first balloon 118 disposed within second balloon 170 define second balloon chamber 190 that is adapted to receive a fluid (e.g., medication).

In the illustrated embodiment, second balloon body 188 defines a plurality of pores 192. Each pore of the plurality pores 192 extends through second balloon body 188 and allows fluid (e.g., medication) to pass through second balloon body 188 with the application of pressure within the second balloon chamber 190. A plurality of pores defined by the body of a balloon can be arranged in any suitable configuration. For example, a plurality of pores defined by the body of a balloon can be arranged around the circumference of a balloon such that each pore of the plurality of pores, or a portion of the plurality of pores, is disposed on a plane that is disposed orthogonal to, or at an angle to, the lengthwise axis of the elongate member. A marker, such as those described herein with respect to marker 391, can be disposed adjacent to the plurality of pores, or a portion of the plurality of pores, such that placement of the plurality of pores can be determined during the performance of a procedure.

Second balloon 170 is attached to elongate member 116 such that second infusion lumen opening 178 is in communication with second balloon chamber 190. With this structural arrangement, second balloon 170 is adapted to receive fluid within second balloon chamber 190 and, with the application of pressure within balloon chamber 190, pass the fluid through one or more of the plurality of pores 192. Second balloon 170 is adapted to move between a first, deflated configuration and second, inflated configuration by way of movement of first balloon 118 between its first inflated configuration and second deflated configuration. FIG. 3 illustrates second balloon 170 in the second, inflated configuration. Thus, the user expands second balloon 170 by inflating first balloon 118. To move second balloon 170 to the first, deflated configuration, vacuum pressure can be applied to inflation port 126 and/or infusion port 172 to remove fluid within balloon chamber 154 and/or balloon chamber 190 resulting in first balloon 118 and second balloon 170 returning to their respective deflated configurations.

Depending on the size and number of pores defined by second balloon body 188, second balloon 170 can be adapted to move between the first, deflated configuration and second, inflated configuration as a fluid (e.g., medication) is moved into and out of second balloon chamber 190 via infusion port 172, infusion lumen 174, and second infusion lumen opening 178. Configurations that allow for second balloon 170 to move between deflated and inflated configurations advantageously provide two different inflated configurations for the medical device 110. For example, a first configuration where the first balloon 118 is inflated and a second configuration where the first balloon 118 is inflated in combination with the second balloon 170.

In the first, deflated configuration, first balloon 118 and second balloon 170 can be structurally arranged with elongate member 116 in any suitable manner, and skilled artisans will be able to select a suitable structural arrangement between an elongate member, a first balloon, and a second balloon according to a particular embodiment based on various considerations, including the material(s) forming a balloon and/or an elongate member. Example structural arrangements considered suitable between a first balloon, second balloon, and an elongate member include, but are not limited to, folding a portion, or the entirety, of a first balloon and/or second balloon with the first portion of the elongate member axial length, folding only a portion of a first balloon and/or second balloon with a portion of the first portion of the elongate member axial length, wrapping a portion, or the entirety, of a first balloon and/or second balloon with the first portion of the elongate member axial length, and any other structural arrangement considered suitable for a particular application, including combinations of those described above.

In the illustrated embodiment, first balloon 118, second balloon 170, and first portion of elongate member axial length 140 have been folded, such as a conventional uninflated balloon. Optionally, any of the balloons described herein, such as first balloon 118 and/or second balloon 170, can be folded and then heat set using any suitable temperature (e.g., 170 degrees Fahrenheit, about 170 degrees Fahrenheit) for any suitable interval of time (e.g., 5 minutes, about 5 minutes). In the first, non-expanded configuration, medical device 110 has a first outside diameter at medical device distal end 114 and a second outside diameter at medical device proximal end 112. The first outside diameter is less than the second outside diameter. In the second, expanded configuration, medical device 110 has a third outside diameter at medical device distal end 114 that is equal, or substantially equal, to the second outside diameter. Each of the first diameter, second diameter, and third diameter can be measured along a plane that is orthogonal, or substantially orthogonal, to the elongate member lengthwise axis.

While second balloon body 188 has been illustrated as defining a plurality of pores 192, a balloon body can define any suitable number of pores, and skilled artisans will be able to select a suitable number of pores for a balloon body to define according to a particular embodiment based on various considerations, including the treatment desired to be performed. Example number of pores considered suitable to include on a balloon include, but are not limited to, one, at least one, two, a plurality, three, four, five, six, seven, and any other number considered suitable for a particular application.

Second balloon 170 can be formed of any suitable material, and skilled artisans will be able to select a suitable material to form a balloon according to a particular embodiment based on various considerations, including the materials that form an elongate member. Example materials considered suitable to form a balloon include, but are not limited to, those described above with respect to balloon 18. For example, a first balloon can be formed of a first material and a second balloon can be formed of a second material. The first material and the second material can be the same material or different.

Second balloon proximal junction 180 and second balloon distal junction 182 can comprise any suitable method of attachment between elongate member 116 and second balloon 170, and skilled artisans will be able to select a suitable method of attachment between a balloon and an elongate member according to a particular embodiment based on various considerations, including the material(s) that forms the elongate member and balloon. Example methods of attachment considered suitable between an elongate member and a balloon include, but are not limited to, those described above with respect to medical device 10.

Additional structure can be attached to elongate member 116 (e.g., infusion port 172) to facilitate infusion of a medication into a bodily passage and/or the wall of a bodily passage, as described herein. For example, an infusion device, such as a syringe, can be operatively connected, or attached, to elongate member 116 (e.g., to elongate member infusion port 172) and adapted to introduce medication into second balloon chamber 190. Any infusion device capable of facilitating introduction of medication into a balloon chamber is considered suitable, and skilled artisans will be able to select a suitable infusion device according to a particular embodiment based on various considerations, including the procedure intended to be performed. Example infusion devices considered suitable include, but are not limited to, manually operated infusion devices, syringes, electromechanical infusion devices, pumps, and any other device considered suitable for a particular application.

While second balloon 170 has been illustrated as disposed on elongate member 116 such that each of second balloon proximal end 184 and second balloon distal end 186 is disposed on first portion of elongate member axial length 140, any suitable structural arrangement between a balloon and an elongate member can be used. Skilled artisans will be able to select a suitable structural arrangement between a balloon and an elongate member according to a particular embodiment based on various considerations, including the material(s) that form a balloon and/or elongate member. Example locations considered suitable to position a balloon on an elongate member include, but are not limited to, those described herein (e.g., with respect to first balloon, such that one or both of the balloon proximal end 184 or balloon distal end 186 is disposed on first portion of elongate member axial length 140 or second portion of elongate member axial length 142).

While medical device 110 has been described as including a first balloon 118 and a second balloon 170, a medical device can include any suitable number of balloons, and skilled artisans will be able to select a suitable number of balloons to include on a medical device according to a particular embodiment based on various considerations, including the procedure intended to be performed. Example number of balloons considered suitable to include in a medical device include, but are not limited to, one, at least one, two, a plurality, three, and any other number considered suitable for a particular application. For example, a medical device can comprise a single balloon defining one or more pores as described above. When a single balloon is disposed on the distal end of the elongate tubular member, the elongate tubular member can comprise an infusion port and define an infusion lumen in communication with the single balloon.

Any of the herein described medical devices can include an elongate member and balloon having a structural arrangement similar to elongate member 116, first balloon 118, and second balloon 170. Thus, any of the herein described medical devices can include an elongate member that defines a device lumen, inflation lumen, and an infusion lumen. In addition, any of the herein described medical devices can include a first balloon disposed within a second balloon that has a body defining one or more pores.

FIG. 4 illustrates a third exemplary medical device 210. Medical device 210 is similar to medical device 10 illustrated in FIGS. 1 and 2 and described above, except as detailed below. Reference numbers in FIG. 4 refer to the same structural element or feature referenced by the same number in FIGS. 1 and 2, offset by 200. Thus, medical device 210 has a medical device proximal end 212, medical device distal end 214, and comprises an elongate member 216, balloon 218, and ventilation tube 260. Medical device 210 is adapted to move between a first, non-expanded configuration and a second, expanded configuration.

In the illustrated embodiment, first portion of elongate member axial length 240 is formed of a first material and second portion of elongate member axial length 242 is formed of a second material that is different than the first material. The first material is flexible relative to the second material (e.g., first material is more flexible than the second material, first material is relatively more flexible than the second material). Thus, the second material is rigid relative to the first material (e.g., second material is more rigid than the first material, second material is relatively more rigid than the first material).

First portion of elongate member axial length 240 can be attached to the second portion of elongate member axial length 242 at a junction using any suitable method of attachment. Skilled artisans will be able to select a suitable method of attachment between a first portion of an elongate member axial length and a second portion of an elongate member axial length according to a particular embodiment based on various considerations, including the material that forms each portion of the elongate member axial length. Example methods of attachment considered suitable between the first portion of an elongate member axial length and a second portion of an elongate member axial length include, but are not limited to, using an adhesive, welding, fusing (e.g., heat fusing), and any other method of attachment considered suitable for a particular application.

In the illustrated embodiment, balloon 218 is attached to first portion of elongate member axial length 240 such that each of balloon 218 and the first portion of the elongate member axial length 240 can be folded, or structurally arranged as otherwise described herein, to achieve a first, non-expanded configuration.

FIGS. 5 and 6 illustrate a fourth exemplary medical device 310. Medical device 310 is similar to medical device 10 illustrated in FIGS. 1 and 2 and described above, except as detailed below. Medical device 310 has a medical device proximal end 312 and medical device distal end 314 and comprises an elongate member 316, balloon 318, and ventilation tube 390. Medical device 310 is adapted to move between a first, non-expanded configuration and a second, expanded configuration, as described in more detail below.

In the illustrated embodiment, elongate member 316 is adapted to move between a first, non-expanded configuration and a second, expanded configuration and comprises an elongate member proximal end 320, elongate member distal end 322, elongate member lengthwise axis 323, elongate member axial length 325, proximal fitting 326, inner member 328, and outer member 330.

Proximal fitting 326 has a fitting proximal end 332, fitting distal end 334, and a fitting body 336 that defines a first lumen 338, recess 339, first lumen first opening 340, first lumen second opening 342, inflation port 344, second lumen 346, second lumen first opening 348, and second lumen second opening 350. Fitting body 336 defines recess 339 in first lumen 338. Recess 339 extends from fitting distal end 334 toward fitting proximal end 332. First lumen 338 extends from first lumen first opening 340 to first lumen second opening 342. Second lumen 346 extends from second lumen first opening 348 defined on inflation port 344 to second lumen second opening 350. Optionally, recess 339 can be omitted.

Proximal fitting 326 can be formed of any suitable material, and skilled artisans will be able to select a suitable material to form a proximal fitting according to a particular embodiment based on various considerations, including the desired flexibility of the proximal fitting. Example materials considered suitable to form a proximal fitting include, but are not limited to, those described above with respect to elongate member 16. In the illustrated embodiment, proximal fitting 320 is formed of a material that is rigid, or substantially rigid, relative to the material that forms inner member 328 and outer member 330 (e.g., proximal fitting 320 is relatively more rigid than the inner member 328 and outer member 330).

Inflation port 344 and/or fitting proximal end 332 can optionally include any suitable connector and/or adapter capable of attaching one or more devices to elongate member 316. Example connectors and/or adapters considered suitable to include on an inflation port and/or fitting proximal end include, but are not limited to, threaded connectors, Tuohy Borst adapters, luer lock connectors, and any other connector and/or adapter considered suitable for a particular application.

While proximal fitting 326 has been illustrated as having a bifurcated structural configuration, a proximal fitting can have any suitable structural configuration defining any suitable number of ports and/or lumens. Skilled artisans will be able to select a suitable structural configuration and number of ports and/or lumens for a proximal fitting according to a particular embodiment based on various considerations, including the desired treatment intended to be performed. Example structural arrangements and number of lumens and/or ports considered suitable to define on a proximal fitting include, but are not limited to, those described above with respect to elongate member 16.

Inner member 328 has a inner member proximal end 352, inner member distal end 354, and an inner member body 356 that defines an inner member first opening 358, inner member second opening 360, and a device lumen 362. Device lumen 362 extends from the inner member first opening 358 to the inner member second opening 360. Inner member proximal end 352 is attached to proximal fitting 326 within first lumen 338 and proximal to second lumen second opening 350 such that device lumen 362 is in communication with first lumen first opening 340.

Inner member 328 comprises an inner member proximal portion 328' and an inner member distal portion 328". Inner member proximal portion 328' extends from the inner member proximal end 352 toward the inner member distal end 354 along second portion of elongate member axial length 386. Inner member distal portion 328" extends from the inner member distal end 354 to the inner member proximal portion 328' along the first portion of elongate member axial length 384. Inner member proximal portion 328' and inner member distal portion 328" are attached to one another at inner member junction 329 disposed between the inner member proximal end 352 and the inner member distal end 354.

In the illustrated embodiment, the inner member body 356 has a first wall thickness along a portion, or the entirety, of inner member proximal portion 328' and a second wall thickness along a portion, or the entirety, of inner member distal portion 328". The first wall thickness is greater than the second wall thickness. The material forming the inner member proximal portion 328' can be the same as, or different from, the material forming the inner member distal portion 328". This structural arrangement is considered advantageous at least because it provides a mechanism for moving elongate member 316 between a first, non-expanded configuration and a second, expanded configuration. Alternatively, the wall thickness of an inner member proximal portion and an inner member distal portion can be the same and the inner member proximal portion can comprise a first material and the inner member distal portion can comprise a second material that is different from the first material and/or flexible relative to the first material.

Outer member 330 is disposed over inner member 328 and has an outer member proximal end 364, outer member distal end 366, and an outer member body 368 that defines an outer member first opening 370, inflation lumen 374, and balloon 318. Thus, outer member 330 forms balloon 318. Outer member proximal end 364 is attached to proximal fitting 326 within recess 339 such that each of outer member first opening 370 and inflation lumen 374 is in communication with second lumen 346. Outer member distal end 366 is attached to inner member distal end 354. Balloon 318 comprises a balloon proximal end 378 and a balloon distal end 380 and is disposed between outer member proximal end 364 and outer member distal end 366. Thus, balloon 318 is disposed between elongate member proximal end 320 and elongate member distal end 322. Balloon 318 is adapted to move between a first, deflated configuration and a second, inflated configuration.

Outer member 330 comprises an outer member proximal portion 330' and an outer member distal portion 330". Outer member proximal portion 330' extends from the outer member proximal end 364 toward the outer member distal end 366 along second portion of elongate member axial length 386. Outer member distal portion 330" extends from the outer member distal end 366 to the outer member proximal portion 330' along the first portion of elongate member axial length 384. Outer member proximal portion 330' and outer member distal portion 330" are attached to one another at outer member junction 331 disposed between the outer member proximal end 364 and the outer member distal end 366.

In the illustrated embodiment, the outer member body 368 has a first wall thickness along a portion, or the entirety, of outer member proximal portion 330' and a second wall thickness along a portion, or the entirety, of outer member distal portion 330". The first wall thickness is greater than the second wall thickness. The material forming the outer member proximal portion 330' can be the same as, or different from, the material forming the outer member distal portion 330". This structural arrangement is considered advantageous at least because it provides a mechanism for moving elongate member 316 between a first, non-expanded configuration and a second, expanded configuration. Alternatively, the wall thickness of an outer member proximal portion and an outer member distal portion can be the same and the outer member proximal portion can comprise a first material and the outer member distal portion can comprise a second material that is different from the first material and/or flexible relative to the first material.

Inner member junction 329 and outer member junction 331 can comprise any suitable method of attachment between a proximal portion and a distal portion of an outer member and/or inner member, and skilled artisans will be able to select a suitable method of attachment between a proximal portion and a distal portion of an outer member and/or inner member according to a particular embodiment based on various considerations, including the material(s) that forms the proximal portion and the distal portion. Example methods of attachment considered suitable between a proximal portion and a distal portion of an inner member and/or outer member include, but are not limited to, attachments formed by heat fusing, using adhesives, mechanical connections, and any other method considered suitable for a particular application.

Outer member body 368 and the portion of the exterior surface of inner member 328 disposed within outer member 330 define inflation lumen 374 and a balloon chamber 382 that is adapted to receive a fluid. With this structural arrangement, balloon 318 is adapted to move between the first, deflated configuration and second, inflated configuration as fluid is moved into and out of balloon chamber 382 via the inflation lumen 374 and second lumen second opening 350. FIG. 5 illustrates balloon 318 in the first, deflated configuration and FIG. 6 illustrates balloon 318 in the second, inflated configuration.

A user inflates balloon 318 by introducing a fluid, such as saline, into second lumen 346 and inflation lumen 374 until the fluid passes through inflation lumen 374 and into balloon chamber 382. To move balloon 318 to the first, deflated configuration, vacuum pressure can be applied to inflation lumen 374 to remove fluid located within balloon chamber 382 via second lumen 346, resulting in balloon 318 collapsing and adopting the first, deflated configuration.

Inner member 328 and outer member 330 can be attached to proximal fitting 326 using any suitable method of attachment, and skilled artisans will be able to select a suitable method of attachment between an inner member, outer member, and/or proximal fitting according to a particular embodiment based on various considerations, including the material(s) that forms an inner member, outer member, and/or proximal fitting. Example methods of attachment considered suitable between an inner member, outer member, and/or a proximal fitting include, but are not limited to, attachments formed by heat fusing, using adhesives, mechanical connections, and any other method considered suitable for a particular application.

Additional structure can be attached to elongate member 316 (e.g., inflation port 344) to facilitate the inflation and deflation of balloon 318, as described above. Example inflation devices considered suitable include, but are not limited to, those described above with respect to medical device 10.

Each of inner member 328 and outer member 330 can be formed of any suitable material, and skilled artisans will be able to select a suitable material for an inner member and/or outer member according to a particular embodiment based on various considerations, including the desired flexibility of the inner member and/or outer member. Example materials considered suitable to form an inner member and/or outer member include, but are not limited to, biocompatible materials, materials that can be made biocompatible, flexible materials, substantially flexible materials, polymers, Pebax (Pebax is a registered trademark of Ato Chimie Corporation of Allee des Vosges, Courbevoie, France), nylon, polyethylene, polyurethane, polytetrafluoroethylene (PTFE), ePTFE, and any other material considered suitable for a particular application. For example, an inner member and outer member can be formed of the same material, which is flexible relative to the material forming a proximal fitting (e.g., inner member and outer member are formed of a material that is more flexible than the material that forms the proximal fitting, inner member and outer member are formed of a material that is relatively more flexible than the material that forms the proximal fitting). Alternatively, the outer member can be formed of a material that is the same as the material of the proximal fitting. Alternatively, an inner member can be formed of a first material and outer member can be formed of a second material that is different than the first material. The first material can have a different structural arrangement than the second material. For example, the first material can have a wall thickness that is less than the wall thickness of the second material.

In the illustrated embodiment, elongate member 316 has a first portion of elongate member axial length 384 and a second portion of elongate member axial length 386. First portion of elongate member axial length 384 extends from elongate member distal end 322 toward elongate member proximal end 320 and second portion of elongate member axial length 386 extends from elongate member proximal end 320 to first portion of elongate member axial length 384.

Balloon 318 is disposed on elongate member 316 such that each of balloon proximal end 378 and balloon distal end 380 is disposed on the first portion of elongate member axial length 384. Thus, the entire axial length of balloon 318 is disposed on the first portion of elongate member axial length 384. However, other configurations of a balloon along an elongate member axial length are considered suitable, as described herein. For example, at least a portion of a balloon (e.g., balloon distal end) can be disposed on a first portion of an elongate member axial length, or a first portion of a balloon (e.g., balloon distal end) can be disposed on a first portion of an elongate member axial length and a second portion of a balloon (e.g., balloon proximal end) can be disposed on a second portion of an elongate member axial length.

First portion of elongate member axial length 384 is adapted to move between a first, non-expanded configuration and a second, expanded configuration, as described above with respect to medical device 10. FIG. 5 illustrates first portion of elongate member axial length 384 in the first, non-expanded configuration and FIG. 6 illustrates first portion of elongate member axial length 384 in the second, expanded configuration.

In the first, deflated configuration, outer member 330 (e.g., balloon 318) can be structurally arranged with inner member 328 in any suitable manner, and skilled artisans will be able to select a suitable structural arrangement between an outer member and an inner member according to a particular embodiment based on various considerations, including the material(s) that forms an outer member and/or an inner member. Example structural arrangements considered suitable between an outer member and an inner member include, but are not limited to, folding a portion, or the entirety, of an outer member with the inner portion, folding only a portion of the outer member with a portion of the inner member, wrapping a portion, or the entirety, of the outer member with the inner member, and any other structural arrangement considered suitable for a particular application, including combinations of those described above.

In the illustrated embodiment, outer member 330 (e.g., balloon 318) and inner member 328 have been folded, such as a conventional uninflated balloon. Thus, in the first, non-expanded configuration, medical device 310 has a first outside diameter at medical device distal end 314 and a second outside diameter at medical device proximal end 312. The first outside diameter is less than the second outside diameter. In the second, expanded configuration, medical device 310 has a third outside diameter at medical device distal end 314 that is equal, or substantially equal, to the second outside diameter. Each of the first diameter, second diameter, and third diameter can be measured along a plane that is orthogonal, or substantially orthogonal, to elongate member lengthwise axis 323.

While balloon 318 has been illustrated as disposed on elongate member such that each of balloon proximal end 378 and balloon distal end 380 is disposed on the first portion of elongate member axial length 384, any suitable structural arrangement between a balloon and an elongate member can be utilized. Skilled artisans will be able to select a suitable structural arrangement between a balloon and an elongate member according to a particular embodiment based on various considerations, including the material(s) that form a balloon and/or elongate member. Example locations considered suitable to position a balloon on an elongate member include, but are not limited to, those described above with respect to medical device 10.

In the illustrated embodiment, a ventilation tube 390 has been passed through device lumen 362 to move elongate member 316 from the first, non-expanded configuration to the second, expanded configuration. Ventilation tube 390 is similar to ventilation tube 60, described above, and comprises a ventilation tube proximal end 392, ventilation tube distal end 394, and a ventilation tube body 396 that defines a ventilation tube lumen 398 that extends through the length of ventilation tube 390. It is considered advantageous to pass a ventilation tube 390 through device lumen 362 such that ventilation can be provided during dilation of a bodily passage, as described in more detail herein.

FIG. 5 illustrates ventilation tube distal end 394 disposed proximal to first portion of elongate member axial length 384 and elongate member 316 in the first, non-expanded configuration. Thus, ventilation tube 390 is partially disposed within device lumen 362. FIG. 6 illustrates ventilation tube distal end 394 disposed distal to elongate member distal end 322 and elongate member 316 in the second, expanded configuration. As ventilation tube 390 is axially advanced through device lumen 362, ventilation tube body 396 contacts elongate member 316 and moves elongate member 316 from the first, non-expanded configuration to the second, expanded configuration.

In the illustrated embodiment, a first marker 391 is disposed on outer member distal end 366, a second marker 393 is disposed on balloon proximal end 378, a third marker 395 is disposed on ventilation tube distal end 394, and a fourth marker 397 is disposed along the working length of balloon 318 (e.g., the axial length of the balloon that contains the maximum diameter of the balloon, the axial length of the balloon intended to dilate a bodily passage). Each of the first marker 391, second marker 393, third marker 395, and fourth marker 397 can comprise any suitable material or structure capable of assisting with the visualization of the location of medical device 310 (e.g., inner member distal end 354, balloon distal end 380, working length of balloon 318, ventilation tube distal end 394) during treatment. For example, each of the first marker 391, second marker 393, third marker 395, and fourth marker 397 can comprise a radiopaque marker, ink printed on a surface of the element described, a protuberance on the element described, or any other suitable material and/or structure. The structural arrangement of first marker 391, second marker 393, third marker 395, and fourth marker 397 is considered advantageous at least because it provides a mechanism for determining the location of the axial length of balloon 318 and the ventilation tube distal end 394 during the performance of a procedure.

Any suitable radiopaque material can be used to form a first marker, second marker, third marker, and/or fourth marker, and skilled artisans will be able to select a suitable radiopaque material according to a particular embodiment based on various considerations, including the bodily passage within which a medical device is intended to be used. Examples of suitable radiopaque materials considered suitable include, but are not limited to, cadmium, tungsten, gold, tantalum, bismuth, platinum, iridium, rhodium, and any other material considered suitable for a particular application.

While first marker 391 has been illustrated as disposed on outer member distal end 366, second marker 393 has been illustrated as disposed on balloon proximal end 378, third marker 395 has been illustrated as disposed on ventilation tube distal end 394, and fourth marker 397 has been illustrated as disposed along the working length of balloon 318, any suitable number of markers can be included on a medical device and positioned at any suitable location. Skilled artisans will be able to select a suitable number of markers to include on a medical device and a suitable location to position each marker according to a particular embodiment based on various considerations, including the treatment intended to be performed. Example numbers of markers considered suitable to include on a medical device include, but are not limited to, one, at least one, two, a plurality, three, four, five, six, and any other number considered suitable for a particular application. Example locations considered suitable to position a marker include, but are not limited to, on an inner member distal end, balloon distal end, balloon proximal end, proximal end of the working length of the balloon, distal end of the working length of the balloon, ventilation tube distal end, and any other location considered suitable for a particular application, or combinations of those described herein. For example, alternative to include a fourth marker 397 that is disposed along the working length of balloon 318, a first marker can be disposed on the proximal end of the working length of the balloon and a second marker can be disposed on the distal end of the working length of the balloon 318.

Optionally, medical device 310 can include a third member disposed over outer member 330 that defines a second balloon. The second balloon having a structural configuration similar to balloon 170 described above with respect to FIG. 3. The proximal fitting defining an infusion port in communication with an infusion lumen defined between the material forming the third member and the portion of the elongate member (e.g., outer member) disposed within the third member such that material introduced into the infusion lumen passes into the second balloon chamber and through the one or more pores.

Various methods of treatment are provided herein. These methods include methods of providing access to a bodily passage during dilation. While some methods are exemplified by methods of providing access to an airway, such as the trachea, the methods can also be used to provide access to any other suitable bodily passage, and skilled artisans will be able to select a suitable bodily passage according to a particular embodiment based on various considerations, such as the treatment desired to be performed.

While the methods described herein are shown and described as a series of acts, it is to be understood and appreciated that the methods are not limited by the order of acts, as some acts may, in accordance with these methods, occur in different orders with other acts described herein, and/or concurrently with other acts described herein.

FIG. 7 is a flowchart representation of an exemplary method 700 of providing access to an airway during dilation.

A step 702 comprises introducing a wire guide having a wire guide proximal end and a wire guide distal into an airway such that the wire guide distal end is disposed within the airway. Another step 704 comprises advancing the wire guide distal end distal to, or beyond, a point of treatment within the airway. The point of treatment comprising a stricture within the airway. Another step 706 comprises introducing a medical device having a medical device proximal end and a medical device distal end over the wire guide and into the airway such that the medical device distal end is disposed within the airway. An exemplary medical device considered suitable to perform one or more steps described in method 700, or any other method or step described herein, is medical device 310. Another step 708 comprises advancing the medical device distally over the wire guide and into the airway such that the medical device distal end is disposed distal to, or beyond, the point of treatment. Another step 710 comprises advancing a ventilation tube having a ventilation tube proximal end and a ventilation tube distal end over the wire guide and through the device lumen such that the ventilation tube distal end is disposed distal to the elongate member distal end. Another step 712 comprises passing fluid into the balloon chamber. Another step 714 comprises removing a portion, or the entirety, of the fluid from the balloon chamber. Another step 716 comprises withdrawing the wire guide from the airway. Another step 718 comprises withdrawing the ventilation tube from the device lumen. Another step 720 comprises withdrawing the medical device from the airway.

Step 702 can be accomplished by placing a distally directed force on any suitable portion of a wire guide such that the wire guide distal end is disposed within the airway. Step 702, and any other step described herein that requires a wire guide, can be accomplished using any suitable wire guide, formed of any suitable material, and having any suitable length, and skilled artisans will be able to select a suitable wire guide, material, and length for a wire guide according to a particular embodiment based on various considerations, including the bodily passage being treated. Optionally, a wire guide can be preloaded in any of the medical devices described herein.

Step 704 can be accomplished by placing a distally directed force on any suitable portion of the wire guide such that the wire guide distal end is advanced distal to, or beyond, the point of treatment. Alternatively, a wire guide can be advanced proximal to, or to, a point of treatment. This step can be accomplished with the assistance of direct visualization of the wire guide (e.g., scope), transcutaneously, using an illuminated wire guide, a camera, or any other suitable visualization technique or through tactile feedback provided by the body of the ventilation tube. Optionally, a wire guide can include a marker, such as those described herein, disposed on the wire guide distal end to assist with determining the position of the wire guide during treatment. While one or more of the methods described herein have been described as being accomplished using a wire guide, each of the methods, steps, alternative steps, and/or optional steps described herein can omit the inclusion of a wire guide and be accomplished without a wire guide.

Step 706 can be accomplished by inserting the wire guide proximal end into and through the device lumen and ventilation tube lumen of medical device 310 and placing a distally directed force on any suitable portion of the medical device 310. Alternatively, a first step can comprise inserting the wire guide proximal end into and through a device lumen and a second step can comprise inserting the wire guide proximal end into and through the ventilation tube lumen. In embodiments that include a dilator, such as dilator 1870, this step can be accomplished by inserting the wire guide proximal end into and through the device lumen and dilator lumen and placing a distally directed force on any suitable portion of the medical device.

While medical device 310 has been illustrated and described as accomplishing one or more steps within method 700, one or more of the steps within method 700, or any other method and/or step described herein, can be accomplished using any suitable medical device having any suitable structural arrangement, and skilled artisans will be able to select a suitable medical device to complete a step and/or method according to particular embodiment based on various considerations, including the treatment intended to be performed. Example medical devices considered suitable include, but are not limited to, medical device 10, medical device 110, medical device 210, medical device 310, medical device 810, medical device 810', medical device 1110, medical device 1410, medical device 1810, medical devices that include a ventilation tube such as ventilation tube 60', or ventilation tube 1560, and any other medical device considered suitable for a particular application.

Figure 7D:
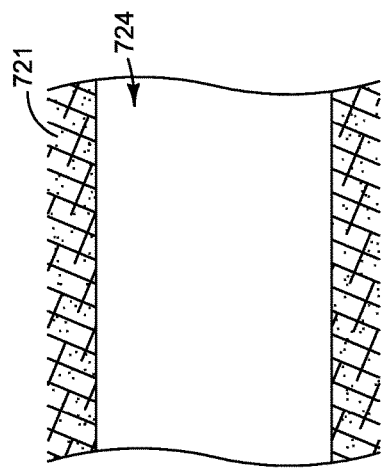
FIG. 7D is a partial sectional view of the airway of a patient following removal of the medical device and the ventilation tube.
Figure 7A:
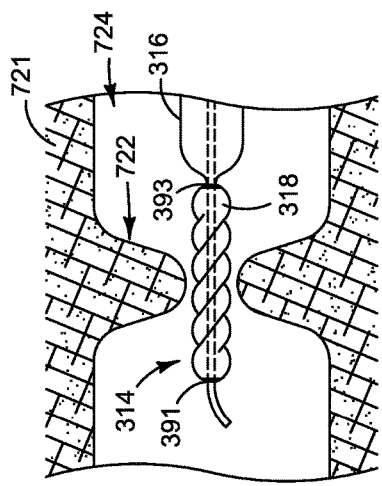
FIG. 7A is a partial sectional view of an airway with a wire guide and the distal end of the medical device illustrated in FIG. 5 disposed in the airway. The medical device is in a first, non-expanded configuration and the associated balloon is in a first, deflated configuration.

FIG. 7A illustrates an airway wall 721 that defines a stricture 722 within an airway 724. While the point of treatment has been illustrated as a stricture 722 within an airway 724, a point of treatment can comprise any suitable part, or portion, of a bodily passage and/or bodily passage wall, and skilled artisans will be able to select a suitable point of treatment to treat according to a method or step described herein based on various considerations, including the treatment intended to be performed.

Step 708 can be accomplished by placing a distally directed force on any suitable portion of medical device 310 such that the medical device distal end 314 is advanced distal to, or beyond, stricture 722. This step can be accomplished with the assistance of x-ray, direct visualization of medical device 310 (e.g., scope), transcutaneously, using an illuminated wire guide, a camera, or any other suitable visualization technique or through tactile feedback provided by the body of the ventilation tube. For example, step 708 can be accomplished by determining that first marker 391 is disposed distal to stricture 722. FIG. 7A illustrates the wire guide distal end and medical device distal end 314 disposed distal to stricture 722. The elongate member 316 is in the first, non-expanded configuration and balloon 318 is in the first, deflated configuration. It is considered advantageous to advance medical device 310 distally through airway 724 such that at least a portion, or the entirety, of the axial length of balloon 318 is disposed along the axial length of stricture 722.

An optional step comprises confirming placement of balloon 318. This step can be accomplished by determining that first marker 391 and/or second marker 393 are disposed along the length of stricture 722, or that first marker 391 is disposed distal to stricture 722 and/or that second marker 393 is disposed proximal to stricture 722.

Step 710 can be accomplished by placing a distally directed force on any suitable portion of ventilation tube 390 such that ventilation tube distal end 394 is advanced distal to, or beyond stricture 722 or elongate member distal end 322. This step can be accomplished with the assistance of x-ray, direct visualization of the cannula (e.g., scope), transcutaneously, using an illuminated wire guide, a camera, or any other suitable visualization technique or through tactile feedback provided by the body of the ventilation tube. For example, step 710 can be accomplished by determining that third marker 395 is disposed distal to stricture 722 and/or elongate member distal end 322. This is step is considered advantageous at least because it provides a mechanism for moving elongate member 316 from the first, non-expanded configuration to the second, expanded configuration and reducing, or eliminating, the shear forces applied to the tissue at a point of treatment while passing a device distal to the point of treatment. Optionally, in embodiments that include a dilator, such as dilator 1870, this step can also include advancing the dilator through the ventilation tube lumen and can be accomplished by placing a distally directed force on any suitable portion of ventilation tube 390 and/or dilator 1870 such that ventilation tube distal end 394 and/or dilator distal end 1875 is advanced distal to, or beyond stricture 722 or elongate member distal end 322.

An optional step comprises ventilating the airway and can be accomplished by attaching ventilation tube 390 to a ventilation device (e.g., ventilator) to provide ventilation (e.g., oxygen) to the portion of the airway distal to stricture 722 and medical device 310. This step is considered advantageous at least because it provides a mechanism for ventilating airway 724 while it is being dilated by balloon 318. This optional step can be accomplished at any suitable time. For example, this optional step can be accomplished prior to and/or concurrent with step 712 and/or after the optional step of withdrawing the dilator from the ventilation tube and/or the optional step of withdrawing the wire guide from the ventilation tube. Optionally, the optional step of attaching the ventilation tube 390 to a ventilation device to provide ventilation to the portion of the airway distal to stricture 722 can be continued during the completion of step 712, step 714, step 718, and/or step 720 (e.g., in embodiments in which any wire guide and/or dilator being used have been withdrawn from the medical device). Optionally, the optional step of attaching the ventilation tube 390 to a ventilation device to provide ventilation to the portion of the airway distal to stricture 722 can be continued during the completion of any other step, such as the optional steps and/or alternative steps described herein. Another optional step comprises stopping the optional step of ventilating the airway and can be completed at any suitable time (e.g., prior to step 720).

Figure 7C:
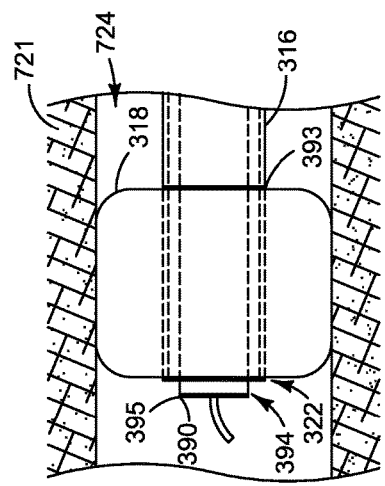
FIG. 7C is a partial sectional view of an airway with a wire guide, the distal end of the medical device illustrated in FIG. 5, and the distal end of a ventilation tube disposed in the airway. The medical device is in a second, expanded configuration and the associated balloon is in a second, inflated configuration.

Step 712 can be accomplished by passing a fluid through inflation lumen and into balloon chamber to move balloon 318 from its first, deflated configuration toward its second, inflated configuration. For example, a syringe in fluid communication with inflation lumen can be used to introduce the fluid into balloon chamber. The amount of the exterior surface of balloon 318 that contacts the tissue in the passage wall, and the amount of pressure exerted by the exterior surface of balloon 318 onto the tissue in the passage wall, will depend on the amount of fluid introduced into balloon chamber. FIG. 7C illustrates balloon 318 in the second, inflated configuration. Skilled artisans can determine a suitable amount of fluid to introduce into a balloon chamber and a suitable interval of time to maintain the balloon in the second, inflated configuration based on various considerations, such as the treatment intended to be performed. While FIG. 7C illustrates the wire guide disposed through the device lumen, a wire guide can optionally be removed prior to a balloon, such as balloon 318, being moved from its first, deflated configuration to its second, inflated configuration.

An optional step comprises continuing the step of passing a fluid through inflation lumen and into balloon chamber until a desired balloon diameter has been achieved. In embodiments that include a dilator, such as dilator 1870, another optional step that can be completed prior to step 712 includes withdrawing the dilator from the ventilation tube. This optional step can be accomplished by applying a proximally directed force on any suitable portion of the dilator until it has been removed from the ventilation tube lumen. Optionally, when ventilation is performed, the optional step of withdrawing the dilator and step 716 can be accomplished prior to step 712 (e.g., in combination with, or separate from, the optional step of withdrawing the dilator).

Example fluids considered suitable to pass through an inflation lumen and into a balloon chamber include, but are not limited to, saline, water contrast, a mixture of one or more of saline, water, and/or contrast, and any other fluid considered suitable for a particular application.

Step 714 can be accomplished by removing the fluid, or a portion of the fluid, passed into balloon chamber to move the balloon toward the first, deflated configuration. For example, a syringe in fluid communication with inflation lumen can be used to provide vacuum pressure to remove the fluid, or a portion of the fluid, from balloon chamber. The amount of fluid removed from balloon chamber can vary depending on the procedure. For example alternative to removing a portion of the fluid, all of the fluid, or substantially all of the fluid, can be removed from balloon chamber.

Step 716 can be accomplished by placing a proximally directed force on any suitable portion of the wire guide such that the wire guide is withdrawn from the airway. It is considered advantageous to complete this step prior to attaching a ventilation device to ventilation tube 390. Alternatively, the step of withdrawing the wire guide from the airway can comprise withdrawing the wire guide from the ventilation tube lumen. Optionally, the step of withdrawing the wire guide from the airway or ventilation tube lumen can be completed prior to the step 712 of passing a fluid into the balloon chamber.

Step 718 can be accomplished by placing a proximally directed force on any suitable portion of the ventilation tube such that the ventilation tube is withdrawn from the airway.

Step 720 can be accomplished by placing a proximally directed force on any suitable portion of the medical device 310 such that the medical device 310 is withdrawn from the airway.

FIG. 7D illustrates airway 724 subsequent to dilation.

While step 716, step 718, and 720 have been described as separate steps, step 716, step 718, and step 720 can be accomplished concurrently with one another.

While method 700 has been illustrated and described as being accomplished using a wire guide, any of the steps, optional steps, and/or alternative steps described herein can be accomplished without a wire guide.

In the illustrated embodiment, it is considered advantageous to complete method 700 in the order illustrated and/or described. It is noted, however, that any order is considered suitable, as described herein.

While ventilation tube 390 has been described as being advanced through device lumen, any suitable medical device can be passed through device lumen, and skilled artisans will be able to select a suitable medical device according to a particular embodiment based on various considerations, including the treatment intended to be performed. Example devices considered suitable to pass through a device lumen include, but are not limited to, elongate members, ventilation tubes, such as those described herein, dilators, such as those described herein, suction catheters, balloon catheters, irrigation catheters, a camera and/or light source disposed on an elongate member, and any other device considered suitable for a particular application.

When medical device 310 includes a second balloon, as described above with respect to FIG. 3, an optional step comprises passing a fluid into the second balloon chamber until the fluid is expelled from one or more of the pores defined by second balloon wall. Another optional step comprises stopping the step of passing fluid into the second balloon chamber.

The medical device, methods, and steps described herein are considered advantageous at least because they provide a mechanism for providing access to a bodily passage (e.g., ventilating) during dilation of the bodily passage. Providing access to a bodily passage during dilation is considered advantageous at least because it allows the bodily passage to be dilated for longer periods of time without completely obstructing the bodily passage, which increases the interval of time that the bodily passage can be treated (e.g., dilated, medication infused and/or introduced into wall of bodily passage).

While various steps, alternative steps, and optional steps have been described above with respect to providing access to an airway, these steps, alternative steps, and optional steps can be included in, accomplished concurrently with, and/or accomplished in the alternative to, the methods, steps, alternative steps, and/or optional steps described below with respect to providing access to an airway.

FIG. 8 is a sectional view of a fifth exemplary medical device 810. Medical device 810 is similar to medical device 10 illustrated in FIGS. 1 and 2 and described above, except as detailed below. Reference numbers in FIG. 8 refer to the same structural element or feature referenced by the same number in FIGS. 1 and 2, offset by 800. Thus, medical device 810 has a medical device proximal end 812, medical device distal end 814, and comprises an elongate member 816 and balloon 818. In the illustrated embodiment, medical device 810 comprises a dilator 900, as described in more detail below. Dilator 900 comprises a dilator shaft 910 and a dilator tip 912.

In the illustrated embodiment, elongate member 816 includes a valve 820', ventilation port 826' and is not moveable between a first, non-expanded configuration and a second expended configuration. In addition, in the illustrated embodiment, a portion 817 of balloon axial length 819 (e.g., working length of balloon) comprises a gripping surface 821 that has a greater coefficient of friction than the remaining portion of balloon 818. Thus, a first portion of the balloon axial length 819 has a first coefficient of friction and a second portion of the balloon axial length 819 has a second coefficient of friction that is less than the first coefficient of friction. It is noted, however, that the elongate member in this embodiment could be moveable between a first, non-expanded configuration and a second, expanded configuration as described above with respect to elongate member 16 in FIGS. 1 and 2.

Valve 820' is attached to elongate member 816 and has a valve body 821' that defines a valve opening 822'. Valve opening 822' can have any suitable diameter. It is considered advantageous for valve opening 822' to have a diameter that is equal to, substantially equal to, or less than, the outside diameter of dilator shaft 910. Valve 820' can comprise any suitable member capable of providing a sealing engagement with dilator shaft 910 during use. Valve 820' can be formed of any suitable material, such as those described herein. It is considered advantageous for valve 820' to be formed of a flexible, or substantially flexible, material relative to dilator shaft 910 (e.g., valve 820' is formed of a material that is more flexible than the material that forms the dilator shaft 910) at least because this provides a mechanism for preventing fluid (e.g., air) from escaping the device lumen 834 during use. Optionally, elongate member proximal end 820 can omit the inclusion of an opening.

Elongate member body 824 defines a ventilation port 826', ventilation lumen 828', first ventilation lumen opening 830', and a second ventilation lumen opening 832'. Ventilation port 826' is disposed on a proximal portion of elongate member 816 and ventilation lumen 828' extends from first ventilation lumen opening 830' defined on ventilation port 826' to second ventilation lumen opening 832' that is in communication with device lumen 834.

The inclusion of a gripping surface 821 on balloon 818 is considered advantageous at least because it provides a mechanism for reducing, or eliminating, axial movement of elongate member 816 and balloon 818 along the wall of a bodily passage during treatment by increasing the adherence of the balloon 818 to the wall of the bodily passage. Gripping surface 821 can comprise any suitable material disposed on the exterior surface of balloon 818, or disposed within the material forming balloon 818, that increases the adhesion, or coefficient of friction, between balloon 818 and a surface that is intended to be contacted by balloon 818 (e.g., wall of a bodily passage, wall defining an airway). Any suitable material can be used to create a gripping surface along a portion or the entirety, of the axial length of a balloon, and skilled artisans will be able to select a suitable material according to a particular embodiment based on various considerations, including the material(s) that form a balloon. Example materials considered suitable include, but are not limited to, adhesives, forming a first portion of a balloon axial length of a first material that has a first coefficient of friction and a second portion of a balloon axial length of a second material that has a second coefficient of friction that is different from, less than, or greater than, the first coefficient of friction, forming a portion, or the entirety, of the axial length of a balloon (e.g., working length of balloon) of a functionalized poly-olefin polymer, applying a functionalized poly-olefin polymer to a portion, or the entirety, of the axial length of a balloon (e.g., working length of balloon), applying a material to a first portion of a balloon axial length that has a first coefficient of friction and a second portion of a balloon axial length having has a second coefficient of friction that is different from, less than, or greater than, the first coefficient of friction, and any other material considered suitable for a particular application.

While gripping surface 821 has been illustrated as extending along a portion 817 of balloon axial length 819, a balloon can comprise an gripping surface that extends along any suitable distance of the balloon axial length, and skilled artisans will be able to select a suitable distance according to a particular embodiment based on various considerations, including the procedure intended to be performed. Example distances considered suitable for an gripping surface to extend along the axial length of a balloon include, but are not limited to, from the balloon proximal end to the balloon distal end, from the balloon proximal end to a location along the balloon axial length disposed between the balloon proximal end and the balloon distal end, from a location along the balloon axial length disposed between the balloon proximal end and the balloon distal end to the balloon distal end, along the working length of the balloon, and any other distance considered suitable for a particular application. Optionally, gripping surface 821 can be omitted.

Ventilation port 826' can optionally include any suitable connector and/or adapter capable of attaching one or more devices to elongate member 816. Skilled artisans will be able to select a suitable connector and/or adapter to include on a ventilation port according to a particular embodiment based on various considerations, including the materials that form the elongate member. Example connectors and/or adapters considered suitable to include on an ventilation port include, but are not limited to, threaded connectors, Tuohy Borst adapters, luer lock connectors, airway connectors, conical connectors (e.g., cones, sockets), such as those described in document BS (British Standards) EN ISO 5356-1:2004, and any other connector and/or adapter considered suitable for a particular application.

Dilator 900 comprises a dilator proximal end 902, tapered dilator distal end 904, and a dilator body 906 that defines a dilator lumen 908 that extends through dilator 900, dilator shaft 910, and a dilator tip 912. Dilator lumen 908 can have any suitable inside diameter, such as those described herein with respect to device lumen 34 and/or a ventilation tube lumen. Dilator 900 is disposed through valve opening 822' and device lumen 834 such that dilator distal end 904 is disposed distal to elongate member distal end 822. This structural configuration is considered advantageous at least because it provides a mechanism for advancing medical device 810 through a narrow portion of a bodily passage (e.g., stricture).

Dilator shaft 910 and dilator tip 912 can be formed of any suitable material, and skilled artisans will be able to select a suitable material to form a dilator shaft and dilator tip according to a particular embodiment based on various considerations, including the material(s) that form an elongate member. Example materials considered suitable to form a dilator shaft and/or dilator tip include, but are not limited to, those described above with respect to medical device 10. For example, dilator shaft 910 can be formed of a first material and dilator tip 912 can be formed of a second material. The first material can be the same as, or different from, the second material. It is considered advantageous for dilator shaft 910 to be rigid, or substantially rigid, relative to dilator tip 912 (e.g., dilator shaft 910 is relatively more rigid than the dilator tip). For example, the dilator shaft 910 can be formed of a rigid, or substantially rigid, first material (e.g., metal) and dilator tip 912 can be formed of a flexible, or substantially flexible, material (e.g., polymer) relative to the first material. Alternatively, dilator shaft 910 can be flexible, or substantially flexible. For example, dilator shaft 910 can be formed of a flexible, or substantially flexible material.

Dilator shaft 910 extends from a dilator shaft proximal end 914 to a dilator shaft distal end 916 and dilator tip 912 extends from a dilator tip proximal end 918 to a dilator tip distal end 920. Dilator tip 912 comprises a first portion 922 and a second portion 924. First portion 922 extends from dilator tip proximal end 918 toward dilator tip distal end 920 to a location along the dilator tip axial length disposed between dilator tip proximal end 918 and dilator distal end 920. Second portion 924 extends from dilator tip distal end 920 toward dilator tip proximal end 918 to a location along the dilator tip axial length disposed between dilator tip proximal end 918 and dilator distal end 920. In the illustrated embodiment, second portion 924 extends from dilator distal end 920 to first portion 922.

First portion 922 has an outside diameter that is equal to, substantially equal to, or less than the inside diameter of device lumen 834. Second portion 924 has an outside diameter at that is greater than the inside diameter of device lumen 834. Thus, dilator tip 912 defines a shoulder 925 between dilator tip proximal end 918 and dilator tip distal end 920. With this structural arrangement, dilator 900 is adapted to be partially disposed within device lumen 834 and is adapted to be advanced proximally, and out of, device lumen 834 during use. This structural arrangement is considered advantageous at least because it provides a mechanism for providing access to a bodily passage during dilation and for withdrawing medical device 810 by advancing dilator 900 proximally through device lumen 834.

Optionally, dilator 900 can include a tip that extends distally from dilator distal end 904. Tip can comprise any suitable structure. For example, tip can have an outside diameter that is less than the outside diameter of dilator tip proximal end 918 and can be a solid member or tubular member adapted to allow a wire guide to pass through the tip. It is considered advantageous to form tip of a flexible, or substantially flexible, material relative to dilator tip 912.

While dilator 900 has been illustrated as having a particular structural arrangement, a dilator can have any suitable structural arrangement capable of providing dilation of a bodily passage and permitting a medical device to provide access to the bodily passage during dilation. For example, a dilator can comprise an elongate member with a tapered distal end. The elongate member can comprise an outside diameter than is less than, or slightly less than, the inside diameter of the device lumen of a medical device (e.g., device lumen 834) such that the dilator can be advanced distal to the elongate member distal end and withdrawn from device lumen after the medical device has been advanced to a desired point of treatment.

FIGS. 8A and 8B illustrate a sixth exemplary medical device 810'. Medical device 810' is similar to medical device 810 illustrated in FIG. 8 and described above, except as detailed below. Reference numbers in FIGS. 8A and 8B refer to the same structural element or feature referenced by the same number in FIG. 8, offset by '. Thus, medical device 810' has a medical device proximal end 812', medical device distal end 814', and comprises an elongate member 816', balloon 818' and a dilator 900'.

In the illustrated embodiment, medical device 810' omits the inclusion of a valve (e.g., valve 820') and a ventilation port (e.g., ventilation port 826') and balloon 818' omits the inclusion of a gripping surface (e.g., gripping surface 821). In the illustrated embodiment, dilator shaft 910' extends from a dilator shaft proximal end 914' to a dilator shaft distal end 916' and dilator body 906' defines a dilator opening 911' between the dilator shaft proximal end 914' and the dilator shaft distal end 916'. Dilator tip 912' extends from a dilator tip proximal end 918' to a dilator tip distal end 920'. Dilator tip 912' tapers from the dilator tip proximal end 918' to the dilator tip distal end 920'. Thus, dilator tip 912' has a first diameter at dilator tip proximal end 918' that is greater than a second diameter at dilator tip distal end 920'.

In use, dilator shaft proximal end 914' can include any suitable connector, such as those described herein, and be attached to a ventilation device such that ventilation can be accomplished through dilator opening 911'. For example, dilator 900' can be advanced distally through device lumen 834' until a portion, or the entirety, of dilator opening 911' is disposed distal to elongate member distal end 822' and ventilation can be accomplished. Alternatively, ventilation can be accomplished without attaching a ventilation device to dilator shaft proximal end 914'.

Figure 9:
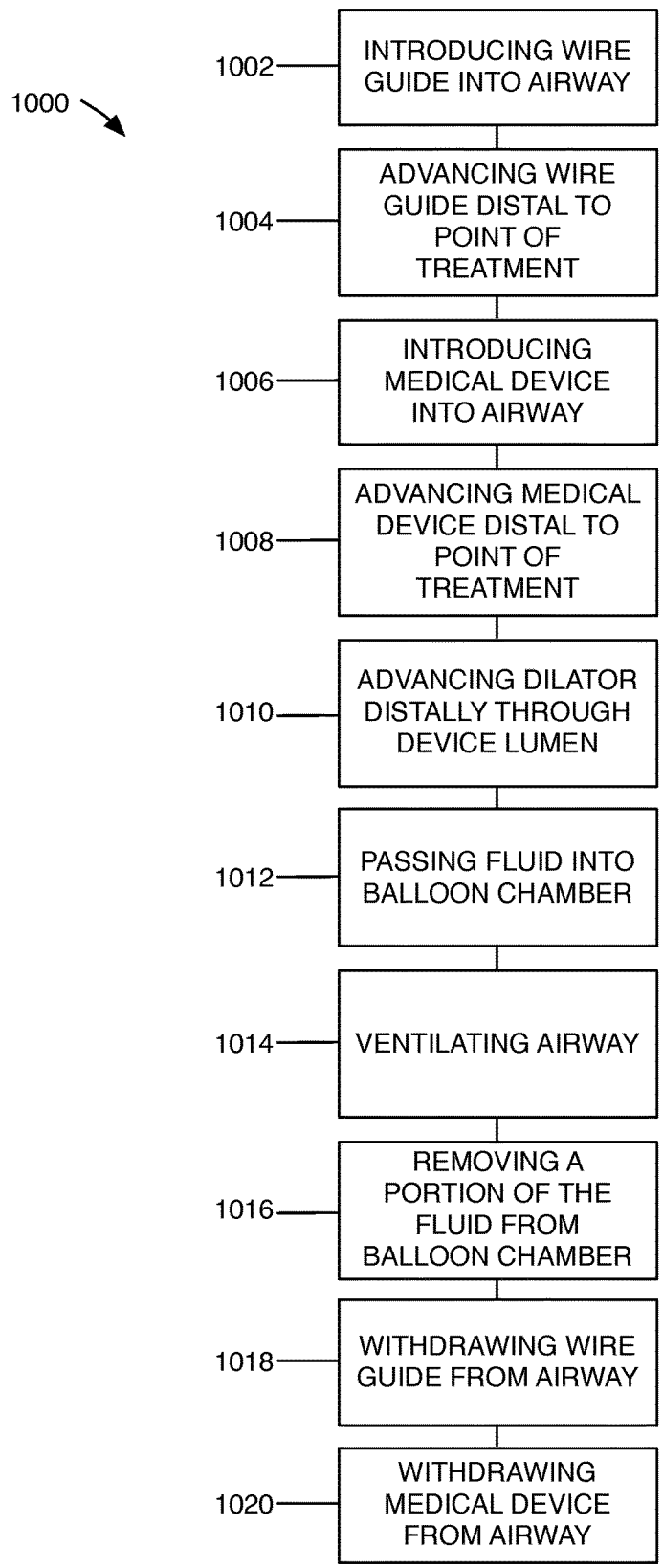
FIG. 9 is a flowchart representation of another exemplary method of providing access to a bodily passage during dilation.

FIG. 9 is a flowchart representation of another exemplary method 1000 of providing access to an airway during dilation.

A step 1002 comprises introducing a wire guide having a wire guide proximal end and a wire guide distal into an airway such that the wire guide distal end is disposed within the airway. Another step 1004 comprises advancing the wire guide distal end distal to, or beyond, a point of treatment within the airway. The point of treatment comprising a stricture within the airway. Another step 1006 comprises advancing a medical device having a medical device proximal end and a medical device distal end over the wire guide and into the airway such that the medical device distal end is disposed within the airway. An exemplary medical device considered suitable to perform one or more steps described in method 1000, or any other method or step described herein, is medical device 810. Medical device comprises an elongate member, balloon, and a dilator. Dilator comprises a dilator shaft and a dilator tip. Another step 1008 comprises advancing the medical device distally over the wire guide and into the airway such that the medical device distal end is disposed distal to, or beyond, the point of treatment. Another step 1010 comprises advancing the dilator distally through the device lumen such that a portion, or the entirety, of the dilator tip moves to a position distal to the elongate member distal end. Another step 1012 comprises passing fluid into the balloon chamber. Another step 1014 comprises ventilating the airway. Another step 1016 comprises removing a portion of the fluid from the balloon chamber. Another step 1018 comprises withdrawing the wire guide from the airway. Another step 1020 comprises withdrawing the medical device from the airway.

In the illustrated embodiment, as illustrated in FIGS. 9A and 9B, the point of treatment is a stricture 722 within an airway 724. While the point of treatment has been illustrated as a stricture within an airway, a point of treatment can comprise any suitable part, or portion, of a bodily passage and/or bodily passage wall, and skilled artisans will be able to select a suitable point of treatment according to a particular embodiment based on various considerations, including the treatment intended to be performed.

Step 1002 is accomplished as described above with respect to step 702 and step 1004 is accomplished as described above with respect to step 704. While one or more of the methods described herein have been described as being accomplished using a wire guide, each of the methods, steps, alternative steps, and/or optional steps described herein can omit the inclusion of a wire guide and be accomplished without a wire guide.

Step 1006 can be accomplished by inserting the wire guide proximal end into and through dilator lumen and placing a distally directed force on any suitable portion of medical device 810.

Step 1008 can be accomplished by placing a distally directed force on any suitable portion of medical device 810 such that the medical device distal end 814 is advanced distal to, or beyond, stricture 722. This step can be accomplished with the assistance of x-ray, direct visualization of medical device 810 (e.g., scope), transcutaneously, using an illuminated wire guide, a camera, or any other suitable visualization technique or through tactile feedback provided by the body of the ventilation tube. FIG. 9A illustrates medical device distal end 814 disposed distal to, or beyond, stricture 722 and balloon 818 in the first, deflated configuration.

Step 1010 can be accomplished by placing a distally directed force on any suitable portion of dilator 900 such that dilator 900 is advanced distally into airway 724 and a portion, or the entirety of, dilator tip 912 is disposed distal to elongate member distal end 822. It is considered advantageous to advance dilator 900 distally into airway 724 such that dilator tip proximal end 918 is disposed distal to elongate member distal end 822 to increase the flow of fluid (e.g., oxygen) during ventilation. Alternatively, if medical device 810' is being used to complete method 1000, then this step would be accomplished by placing a distally directed force on any suitable portion of the dilator 900' such that the dilator 900' is advanced distally into airway 724 and a portion, or the entirety, of dilator opening 911' is disposed distal to elongate member distal end 822'.

Step 1012 can be accomplished by passing a fluid through inflation lumen and into balloon chamber to move balloon 818 from its first, deflated configuration toward its second, inflated configuration. For example, a syringe in fluid communication with inflation lumen can be used to introduce the fluid into balloon chamber. FIG. 9B illustrates balloon 818 in the second, inflated balloon configuration.

Step 1014 is considered optional and can be accomplished by attaching a ventilation device to the ventilation port 826' and activating the ventilation device (e.g., ventilator) such that fluid (e.g., oxygen) can be provided to the portion of the airway distal to balloon 818. This step is considered advantageous at least because it provides a mechanism for ventilating airway 724 while it is being dilated by balloon 818. Alternatively, if medical device 810' is being used to complete method 1000, then this step would be accomplished by attaching a ventilation device to dilator shaft proximal end 914' and activating the ventilation device (e.g., ventilator) such that fluid (e.g., oxygen) can be provided to the portion of the airway distal to balloon 818'. Optionally, step 1014 can be accomplished prior to step 1012 such that ventilation is accomplished prior to and/or during the step of passing a fluid into the balloon chamber and moving the balloon from the first, deflated configuration to the second, inflated configuration. Optionally, step 1014 can be continued during the completion of step 1012, step 1016, and/or step 1020 (e.g., in embodiments in which any wire guide and/or dilator being used have been withdrawn from the medical device). Optionally, step 1014 can be continued during the completion of any other step, such as the optional steps and/or alternative steps described herein. Another optional step comprises stopping the step of ventilating the airway and can be completed at any suitable time (e.g., prior to step 1020).

While step 1010, step 1012, and step 1014 have been described as being accomplished in a particular order, any suitable order can be used. For example, step 1010, step 1012, and step 1014 can be accomplished concurrently, step 1010 can be accomplished then step 1014 can be accomplished then step 1012 can be accomplished, or step 1012 can be accomplished then step 1010 can be accomplished then step 1014 can be accomplished.

Step 1016 can be accomplished by removing the fluid, or a portion of the fluid, passed into balloon chamber to move the balloon toward the first, deflated configuration. For example, a syringe in fluid communication with inflation lumen can be used to provide vacuum pressure to remove the fluid, or a portion of the fluid, from balloon chamber. The amount of fluid removed from balloon chamber can vary depending on the procedure. For example alternative to removing a portion of the fluid, all of the fluid, or substantially all of the fluid, can be removed from balloon chamber.

Step 1018 can be accomplished by placing a proximally directed force on any suitable portion of the wire guide such that the wire guide is withdrawn from the airway. It is considered advantageous to complete this step prior to attaching a ventilation device to medical device 810.

Step 1020 can be accomplished by placing a proximally directed force on any suitable portion of medical device 810 such that medical device 810 is withdrawn from the airway.

While step 1018 and step 1020 have been described as separate steps, step 1018 and step 1020 can be accomplished concurrently with one another.

In the illustrated embodiment, it is considered advantageous to complete method 1000 in the order illustrated and/or described. It is noted, however, that any order is considered suitable, as described herein.

When medical device 810 includes a second balloon, as described with respect to FIG. 3, an optional step comprises passing a fluid into the second balloon chamber until the fluid is expelled from one or more of the pores defined by second balloon wall. Another optional step comprises stopping the step of passing fluid into the second balloon chamber.

Alternative to completing method 1000 using medical device 810, a medical device that comprises a dilator that has an elongate member with a tapered distal end can be used. The elongate member comprises an outside diameter that is less than, or slightly less than, the inside diameter of the device lumen of the medical device (e.g., device lumen 834) such that the dilator can be advanced distally through the device lumen and withdrawn from device lumen after the medical device has been advanced to a desired point of treatment. When a dilator having this structural arrangement is used to complete method 1000, an optional step will comprise withdrawing the dilator and the wire guide, if present, from the device lumen and another optional step will comprise withdrawing the elongate member from the airway.

While various steps, alternative steps, and optional steps have been described above with respect to providing access to an airway, these steps, alternative steps, and optional steps can be included in, accomplished concurrently with, and/or accomplished in the alternative to, the methods, steps, alternative steps, and/or optional steps described above and/or below with respect to providing access to an airway.

FIG. 10 is a sectional view of a seventh exemplary medical device 1110. Medical device 1110 is similar to medical device 810 illustrated in FIGS. 8, 9A, and 9B and described above, except as detailed below. Reference numbers in FIG. 10 refer to the same structural element or feature referenced by the same number in FIGS. 8, 9A, and 9B, offset by 300. Thus, medical device 1110 has a medical device proximal end 1112, medical device distal end 1114, and comprises an elongate member 1116 and balloon 1118. In the illustrated embodiment, medical device 1110 comprises a dilator 1200, as described in more detail below.

In the illustrated embodiment, balloon 1118 does not include an adhesive surface (e.g., adhesive surface 821).

In the illustrated embodiment, dilator 1200 is similar to the structural arrangement of elongate member 1116 and balloon 1118, except as detailed below. Reference numbers referring to a structural element or feature of dilator 1200 refer to the same structural element or feature referenced by the same number on elongate member 1116 and balloon 1118, offset by 100. Thus, dilator 1200 comprises a dilator proximal end 1212, dilator distal end 1214, second elongate member 1216 and second balloon 1218.

Second elongate member 1216 comprises an elongate member proximal end 1220, elongate member distal end 1222, and an elongate member body 1224. Elongate member body 1224 defines an inflation port 1226, inflation lumen 1228, first inflation lumen opening 1230, second inflation lumen opening 1232, second device lumen 1234, second device lumen first opening 1236, and a second device lumen second opening 1238.

In the illustrated embodiment, second balloon 1218 is attached to second elongate member 1216 between elongate member proximal end 1220 and elongate member distal end 1222. Second balloon 1218 comprises a second balloon proximal end 1248, second balloon distal end 1250, and a second balloon body 1252. Balloon body 1252 and the portion of the exterior surface of second elongate member 1216 disposed within second balloon 1218 define second balloon chamber 1254 that is adapted to receive a fluid such that second balloon 1218 can be moved between a first, deflated configuration and second, inflated configuration. Second balloon 1218 is attached to second elongate member 1216 such that second inflation lumen opening 1232 is in communication with second balloon chamber 1254. With this structural arrangement, second balloon 1218 is adapted to move between the first, deflated configuration and the second, inflated configuration as fluid is moved into and out of second balloon chamber 1254 via the inflation lumen 1228 and second inflation lumen opening 1232. FIG. 10 illustrates second balloon 1218 in the second, inflated configuration.

Dilator 1200 is disposed through device lumen 1134 such that dilator distal end 1214 is disposed distal to elongate member distal end 1122. In the illustrated embodiment, second elongate member 1216 and balloon 1218 are adapted to be advanced through and withdrawn from device lumen 1134. For example, when second balloon 1218 is in the first, deflated configuration, elongate member 1216 and/or balloon 1218 have an outside diameter that is less than the inside diameter of device lumen 1134. This structural arrangement is considered advantageous at least because it provides a mechanism for pre-dilating a bodily passage with second balloon 1218 and then subsequently dilating the bodily passage with balloon 1118, as described in more detail herein.

While dilator 1200 has been illustrated as including second balloon 1218, a dilator can have any suitable structural arrangement and include any suitable number of balloons. Skilled artisans will be able to select a suitable structural arrangement and number of balloons to include on a dilator according to a particular embodiment based on various considerations, including the treatment intended to be performed.

Figure 11:
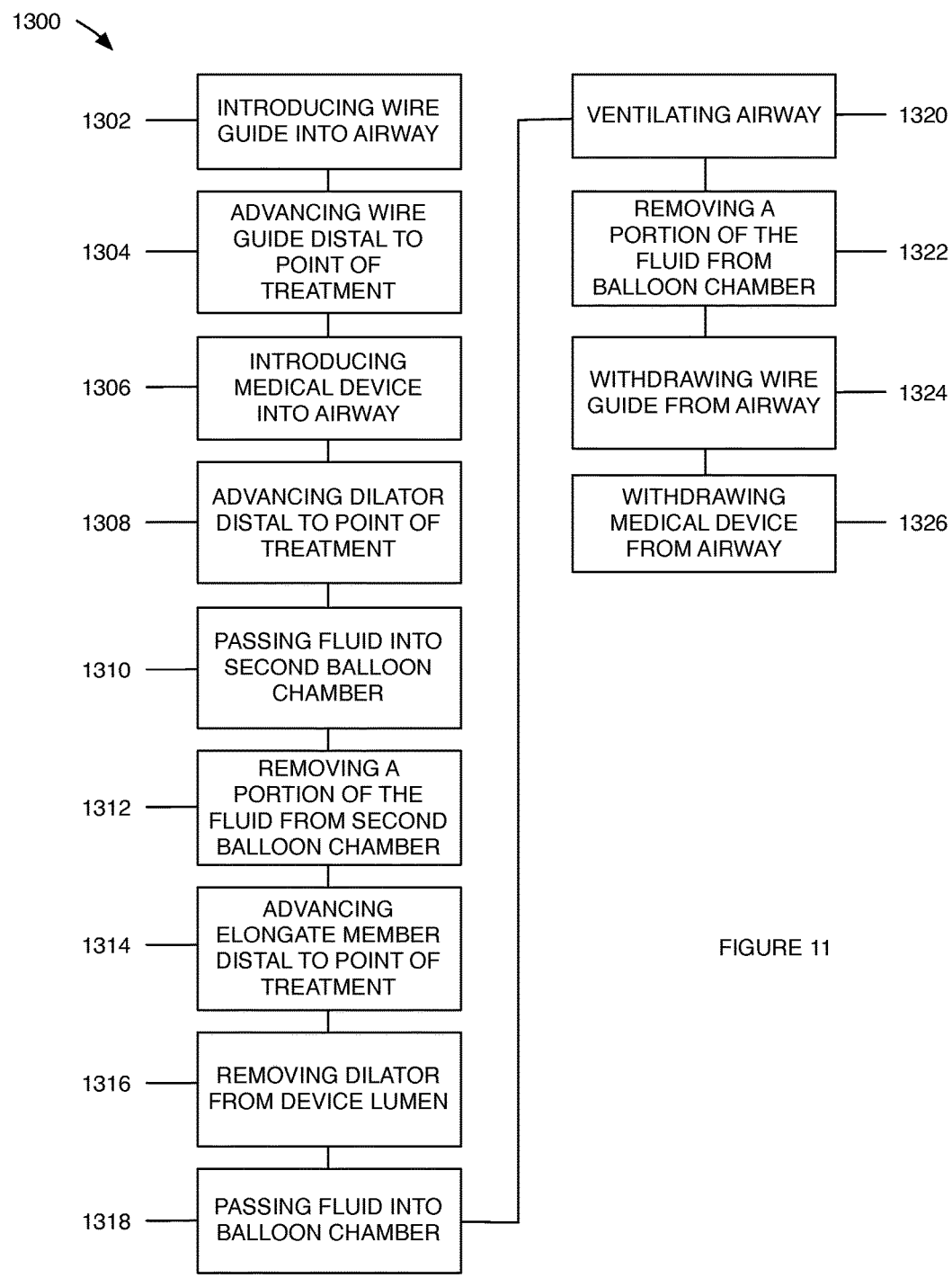
FIG. 11 is a flowchart representation of another exemplary method of providing access to a bodily passage during dilation.

FIG. 11 is a flowchart representation of another exemplary method 1300 of providing access to an airway during dilation.

A step 1302 comprises introducing a wire guide having a wire guide proximal end and a wire guide distal into an airway such that the wire guide distal end is disposed within the airway. Another step 1304 comprises advancing the wire guide distal end distal to, or beyond, a point of treatment within the airway. The point of treatment comprising a stricture within the airway. Another step 1306 comprises introducing a medical device having a medical device proximal end and a medical device distal end over the wire guide and into the airway such that the medical device distal end is disposed within the airway. An exemplary medical device considered suitable to perform one or more steps described in method 1300, or any other method or step described herein, is medical device 1110. The medical device comprises an elongate member, first balloon, and a dilator. The dilator comprises a second elongate member and second balloon. Another step 1308 comprises advancing the medical device distally over the wire guide and into the airway such that the dilator distal end is disposed distal to, or beyond, the point of treatment. Another step 1310 comprises passing fluid into second balloon chamber. Another step 1312 comprises removing a portion of the fluid from second balloon chamber. Another step 1314 advancing the elongate member distally over the wire guide such that elongate member distal end is disposed distal to, or beyond, the point of treatment. Another step 1316 comprises withdrawing the dilator from the device lumen. Another step 1318 comprises passing fluid into the first balloon chamber. Another step 1320 comprises ventilating the airway. Another step 1322 comprises removing a portion of the fluid from the first balloon chamber. Another step 1324 comprises withdrawing the wire guide from the airway. Another step 1326 comprises withdrawing the medical device from the airway.

In the illustrated embodiment, as shown in FIGS. 11A and 11B, the point of treatment is a stricture 722 within an airway 724. While the point of treatment has been illustrated as a stricture within an airway, a point of treatment can comprise any suitable part, or portion, of a bodily passage and/or bodily passage wall, and skilled artisans will be able to select a suitable point of treatment according to a particular embodiment based on various considerations, including the treatment intended to be performed.

Step 1302 is accomplished as described above with respect to step 1002 and step 1304 is accomplished as described above with respect to step 1004. While one or more of the methods described herein have been described as being accomplished using a wire guide, each of the methods, steps, alternative steps, and/or optional steps described herein can omit the inclusion of a wire guide and be accomplished without a wire guide.

Step 1306 can be accomplished by inserting the wire guide proximal end into and through second device lumen and placing a distally directed force on any suitable portion of medical device 1110 (e.g., dilator proximal end).

Step 1308 can be accomplished by placing a distally directed force on any suitable portion of medical device 1110 (e.g., dilator distal end) such that dilator distal end 1214 is advanced distal to, or beyond, stricture 722. This step can be accomplished with the assistance of x-ray, direct visualization of medical device 1110 (e.g., scope), transcutaneously, using an illuminated wire guide, a camera, or any other suitable visualization technique or through tactile feedback provided by the body of the ventilation tube. FIG. 11A illustrates dilator distal end 1214 disposed distal to, or beyond, stricture 722 and each of the first balloon 1118 and second balloon 1218 in the first, deflated configuration.

Step 1310 can be accomplished by passing a fluid through inflation lumen and into second balloon chamber to move second balloon 1218 from its first, deflated configuration toward its second, inflated configuration. For example, a syringe in fluid communication with inflation lumen can be used to introduce the fluid into second balloon chamber. The amount of the exterior surface of second balloon 1218 that contacts the tissue in the passage wall, and the amount of pressure exerted by the exterior surface of second balloon 1218 onto the tissue in the passage wall, will depend on the amount of fluid introduced into second balloon chamber. Phantom lines in FIG. 11A illustrate second balloon 1218 in the second, inflated configuration.

Step 1312 can be accomplished by removing the fluid, or a portion of the fluid, passed into second balloon chamber to move second balloon 1218 toward the first, deflated configuration. For example, a syringe in fluid communication with inflation lumen can be used to provide vacuum pressure to remove the fluid, or a portion of the fluid, from second balloon chamber.

Step 1314 can be accomplished by placing a distally directed force on any suitable portion of elongate member 1116 (e.g., elongate member proximal end) such that elongate member distal end 1122 is advanced distal to, or beyond, stricture 722. This step can be accomplished with the assistance of x-ray, direct visualization of the remaining portion of medical device 1110 (e.g., scope) disposed within the airway, transcutaneously, using an illuminated wire guide, a camera, or any other suitable visualization technique or through tactile feedback provided by the body of the ventilation tube. FIG. 11B illustrates elongate member distal end 1122 disposed distal to, or beyond, stricture 722 and first balloon 1118 in the first, deflated configuration.

Step 1316 can be accomplished by placing a distally directed force on any suitable portion of dilator 1200 such that dilator 1200 is advanced proximally through device lumen and removed from device lumen. Optionally, this step can be completed in combination with step 1324 such that both the dilator and the wire guide are advanced proximally through the device lumen and removed from the device lumen.

Step 1318 can be accomplished by passing a fluid through inflation lumen and into first balloon chamber to move first balloon 1118 from its first, deflated configuration toward its second, inflated configuration. For example, a syringe in fluid communication with inflation lumen can be used to introduce the fluid into first balloon chamber. Phantom lines in FIG. 11B illustrate first balloon 1118 in the second, inflated configuration.

Step 1320 is considered optional and can be accomplished by attaching a ventilation device to the elongate tubular member proximal end and activating the ventilation device (e.g., ventilator) such that fluid (e.g., oxygen) can be provided to the portion of the airway distal to first balloon 1118. This step is considered advantageous at least because it provides a mechanism for ventilating airway 724 while it is being dilated by first balloon 1118. Optionally, step 1320 can be initiated prior to step 1310 (e.g., by attaching ventilation device to proximal end of dilator, as described herein) or 1318 such that ventilation is being completed prior to and/or during step 1310 or step 1318. Optionally, step 1320 can be continued during the completion of step 1310, step 1312, step 1314, step 1316, step 1318, step 1322, and/or step 1326 (e.g., in embodiments in which any wire guide and/or dilator being used have been withdrawn from the medical device). Optionally, step 1320 can be continued during the completion of any other step, such as the optional steps and/or alternative steps described herein. Another optional step comprises stopping the step of ventilating the airway and can be completed at any suitable time (e.g., prior to step 1326).

Step 1322 can be accomplished by removing the fluid, or a portion of the fluid, passed into first balloon chamber to move first balloon 1118 toward the first, deflated configuration. For example, a syringe in fluid communication with inflation lumen can be used to provide vacuum pressure to remove the fluid, or a portion of the fluid, from first balloon chamber.

Step 1324 can be accomplished by placing a proximally directed force on any suitable portion of the wire guide such that the wire guide is withdrawn from the airway. It is considered advantageous to complete this step prior to, concurrent with, or subsequent to, step 1314, step 1318, or step 1320.

Step 1326 can be accomplished by placing a proximally directed force on any suitable portion of the remaining portion of medical device 1110 disposed outside of airway 724 (e.g., elongate member proximal end) such that medical device 1110 is withdrawn from the airway.

While step 1324 and step 1326 have been described as separate steps, step 1324 and step 1326 can be accomplished concurrently with one another.

In the illustrated embodiment, it is considered advantageous to complete method 1300 in the order illustrated and/or described. It is noted, however, that any order is considered suitable, as described herein.

While various steps, alternative steps, and optional steps have been described above with respect to providing access to an airway, these steps, alternative steps, and optional steps can be included in, accomplished concurrently with, and/or accomplished in the alternative to, the methods, steps, alternative steps, and/or optional steps described above and/or below with respect to providing access to an airway.

FIGS. 12, 13, and 14 illustrate an eighth exemplary medical device 1410. Medical device 1410 is similar to medical device 10 illustrated in FIGS. 1 and 2 and described above, except as detailed below. Reference numbers in FIGS. 12, 13, and 14 refer to the same structural element or feature referenced by the same number in FIGS. 1 and 2, offset by 1400. Thus, medical device 1410 has a medical device proximal end 1412 and a medical device distal end 1414. In the illustrated embodiment, medical device 1410 comprises an elongate member 1416, ventilation tube 1460, and a balloon 1470 and is adapted to move between a first, non-expanded configuration and a second, expanded configuration.

In the illustrated embodiment, elongate member 1416 omits the inclusion of an inflation port (e.g., inflation port 26), inflation lumen (e.g., inflation lumen 28), and a balloon (e.g., balloon 18) and the ventilation tube body 1466 defines an inflation port 1471, inflation lumen 1472, first inflation lumen opening 1473, and second inflation lumen opening 1474 and balloon 1470 is disposed on ventilation tube 1460. Inflation port 1471 is disposed on a proximal portion of ventilation tube 1460 and inflation lumen 1472 extends from first inflation lumen opening 1473 defined on inflation port 1471 to second infusion lumen opening 1474 defined between ventilation tube proximal end 1462 and ventilation tube distal end 1464. Inflation port 1471 can optionally include any suitable connector and/or adapter capable of attaching one or more devices to ventilation tube 1460, such as those described herein.

While ventilation tube 1460 has been illustrated and described as having a bifurcated structural configuration defining an inflation port and an inflation lumen, a ventilation tube can have any suitable structural configuration defining any suitable number of ports and/or lumens. Skilled artisans will be able to select a suitable structural configuration and number of ports and/or lumens to include on a ventilation tube according to a particular embodiment based on various considerations, including the desired treatment intended to be performed. For example, alternative to having a bifurcated proximal portion defining an infusion port, as illustrated in FIGS. 12 and 14, a ventilation tube can comprise a straight, or substantially straight, elongate shaft that has a proximal end defining a first inflation lumen opening providing access to an inflation lumen and/or an opening providing access to the ventilation tube lumen. Example number of lumens and/or ports considered suitable to include on a ventilation tube include, but are not limited to, one, at least one, two, a plurality, three, four, five, and any other number considered suitable for a particular application.

In the illustrated embodiment, balloon 1470 is attached to ventilation tube 1460 between ventilation tube proximal end 1462 and ventilation tube distal end 1464 at balloon proximal junction 1475 and balloon distal junction 1476. Balloon 1470 comprises a balloon proximal end 1477, balloon distal end 1478, and balloon body 1479. Balloon body 1479 and the portion of the surface of the ventilation tube 1460 disposed within the balloon 1470 define balloon chamber 1480 that is adapted to receive a fluid such that balloon 1470 can be moved between a first, deflated configuration and second, inflated configuration. Balloon 1470 is attached to ventilation tube 1460 such that second inflation lumen opening 1474 is in communication with balloon chamber 1480. With this structural arrangement, balloon 1470 is adapted to move between the first, deflated configuration and the second, inflated configuration as fluid is moved into and out of balloon chamber 1480 via the inflation lumen 1472 and second inflation lumen opening 1474. FIG. 12 illustrates balloon 1470 in the first, deflated configuration and FIG. 14 illustrates balloon 1470 in the second, inflated configuration.

Balloon 1470 can be formed of any suitable material, and skilled artisans will be able to select a suitable material to form a balloon according to a particular embodiment based on various considerations, including the materials that form a ventilation tube. Example materials considered suitable to form a balloon include, but are not limited to, those described above with respect to balloon 18.

Balloon proximal junction 1475 and balloon distal junction 1476 can comprise any suitable method of attachment between ventilation tube 1460 and balloon 1470, and skilled artisans will be able to select a suitable method of attachment between a balloon and a ventilation tube according to a particular embodiment based on various considerations, including the material(s) that form the elongate member and balloon. Example methods of attachment considered suitable between a ventilation tube and a balloon include, but are not limited to, those described above with respect to the elongate member 12 and balloon 18 of medical device 10.

A user inflates balloon 1470 by introducing a fluid, such as saline, into inflation lumen 1472 until the fluid passes through second inflation lumen opening 1474 and into balloon chamber 1480. The resulting pressure placed on the inner surface of balloon body 1479 by the fluid causes balloon 1470 to inflate and adopt the second, inflated configuration. To move balloon 1470 to the first, deflated configuration, vacuum pressure can be applied to inflation lumen 1472 to remove fluid located within balloon chamber 1480 via second inflation lumen opening 1474, resulting in balloon 1470 collapsing and adopting the first, deflated configuration.

Additional structure can be attached to ventilation tube (e.g., inflation port 1471) to facilitate the inflation and deflation of balloon 1470, as described above. For example, an inflation device, such as a syringe, can be operatively connected, or attached, to ventilation tube 1460 (e.g., to ventilation tube inflation port 1471) and adapted to move balloon 1470 between the first, deflated configuration and second, inflated configuration. Any inflation device capable of facilitating inflation and deflation of a balloon is considered suitable, such as those described herein.

In the illustrated embodiment, ventilation tube 1460 is passed through device lumen 1434 to move elongate member 1416 from the first, non-expanded configuration to the second, expanded configuration. FIG. 12 illustrates ventilation tube distal end 1464 disposed proximal to first portion of elongate member axial length 1440 and elongate member 1416 in the first, non-expanded configuration. Thus, ventilation tube 1460 is partially disposed within device lumen 1434 and balloon 1470 is in the deflated configuration. However, in some embodiments, balloon 1470 could be partially inflated. FIG. 13 illustrates ventilation tube distal end 1464 disposed distal to the proximal end of the first portion of elongate member axial length 1440, proximal to elongate member distal end 1422,' and elongate member 1416 in the second, expanded configuration. However, as described herein, ventilation tube distal end 1464 can be positioned at any suitable location relative to the elongate member distal end 1422 (e.g., at elongate member distal end 1422, proximal to elongate member distal end 1422, distal to elongate member distal end 1422). As ventilation tube 1460 is axially advanced through device lumen 1434, ventilation tube body 1466 contacts elongate member body 1424 and moves elongate member 1416 from the first, non-expanded configuration to the second, expanded configuration. In the illustrated embodiment, the first portion of elongate member axial length 1440 is sized and configured to adapt to the inflated configuration of balloon 1470. This can be accomplished using any suitable structural configuration, such as those described herein with respect to elongate member 12. FIG. 14 illustrates balloon 1470 in the inflated configuration and the first portion of elongate member axial length 1440 adapted to the inflated configuration of the balloon 1470. Thus, when balloon 1470 is in the second, inflated configuration, device lumen 1434 has a fourth inside diameter 1434''' along a portion, or the entirety, of first portion of elongate member axial length 1440 (e.g., along the entire length of balloon 1470, along the working length of the balloon 1470) that is greater than the first inside diameter 1434', the second inside diameter 1434'', and the third inside diameter 1434''' of device lumen 1434.

Any of the herein described medical devices can include a ventilation tube that has a structural arrangement similar to ventilation tube 1460 and skilled artisans will be able to select a suitable medical device to include a ventilation tube, such as ventilation tube 1460, according to a particular embodiment based on various considerations, including the structural arrangement at a point of treatment. Example medical devices considered suitable to include a ventilation tube, such as ventilation tube 1460, include medical device 10, medical device 110, medical device 210, medical device 310, medical device 810, medical device 810', medical device 1110, medical device 1410, medical device 1810, and medical devices that include a ventilation tube such as ventilation tube 60', or ventilation tube 1560. Thus, any of the herein described medical devices can include a ventilation tube that defines a ventilation tube lumen and an inflation lumen and that has a balloon disposed along its length.

Figure 15:
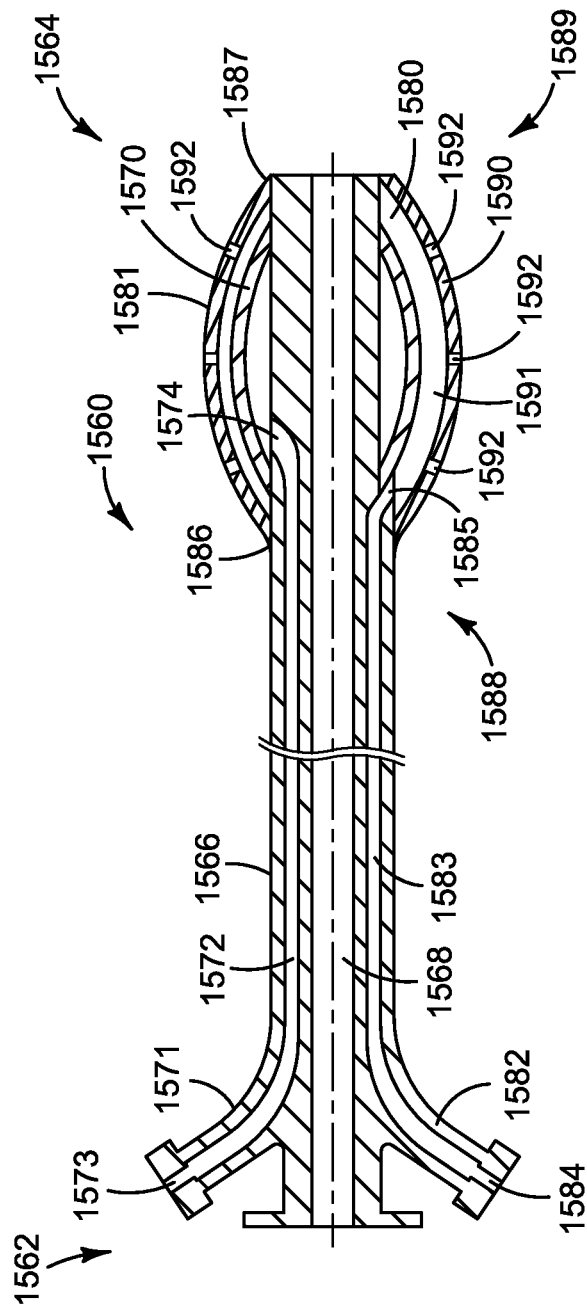
FIG. 15 is a sectional view of another alternative ventilation tube free of a medical device with an associated first balloon and second balloon. Each of the first balloon and second balloon is in a second configuration.

FIG. 15 illustrates an alternative ventilation tube 1560 free of a medical device. Ventilation tube 1560 is similar to ventilation tube 1460 illustrated in FIGS. 12, 13, and 14 and described above, except as detailed below. Reference numbers in FIG. 15 refer to the same structural element or feature referenced by the same number in FIGS. 12, 13, and 14, offset by 100. Thus, ventilation tube 1560 has a ventilation tube proximal end 1562, a ventilation tube distal end 1564, and a ventilation tube body 1566 that defines a ventilation tube lumen 1568. As described herein, the ventilation tube lumen 1568 can have any suitable inside diameter, such as those described above with respect to device lumen 34 and the lumen 68 defined by ventilation tube 60 (e.g., between 3 millimeters and 8 millimeters, between about 3 millimeters and about 8 millimeters).

In the illustrated embodiment, ventilation tube 1560 includes a first balloon 1570 and a second balloon 1581 and ventilation tube body 1566 defines an infusion port 1582, infusion lumen 1583, first infusion lumen opening 1584, and second infusion lumen opening 1585. Infusion lumen 1583 extends from first infusion lumen opening 1584 defined on infusion port 1582 to second infusion lumen opening 1585 defined between ventilation tube proximal end 1562 and ventilation tube distal end 1564.

The first balloon 1570 is disposed within the second balloon 1581 and the second balloon 1581 is attached to ventilation tube 1560 between ventilation tube proximal end 1562 and ventilation tube distal end 1564 at second balloon proximal junction 1586 and second balloon distal junction 1587. Second balloon 1581 comprises a second balloon proximal end 1588, second balloon distal end 1589, and second balloon body 1590. Second balloon body 1590, the portion of the surface of ventilation tube 1560 disposed within second balloon 1590, and the portion of the exterior surface of first balloon 1570 disposed within second balloon 1581 define second balloon chamber 1591 that is adapted to receive a fluid (e.g., medication).

In the illustrated embodiment, second balloon body 1590 defines a plurality of pores 1592. Each pore of the plurality pores 1592 extends through second balloon body 1590 and allows fluid (e.g., medication) to pass through second balloon body 1590 with the application of pressure within the second balloon chamber 1591.

Second balloon 1581 is attached to ventilation tube 1560 such that second infusion lumen opening 1585 is in communication with second balloon chamber 1591. With this structural arrangement, second balloon 1581 is adapted to receive fluid within second balloon chamber 1591 and, with the application of pressure within balloon chamber 1591, pass the fluid through one or more of the plurality of pores 1592. Second balloon 1581 is adapted to move between a first, deflated configuration and second, inflated configuration by way of movement of first balloon 1570 between its first inflated configuration and second deflated configuration. FIG. 15 illustrates second balloon 1581 in the second, inflated configuration. Thus, the user expands second balloon 1581 by inflating the first balloon 1570. To move the second balloon 1581 to the first, deflated configuration, vacuum pressure can be applied to inflation port 1571 to remove fluid within balloon chamber 1580 resulting in first balloon 1570 and second balloon 1581 returning to their respective deflated configurations.

Depending on the size and number of pores 1592 defined by second balloon body 1590, second balloon 1581 can be adapted to move between the first, deflated configuration and second, inflated configuration as a fluid (e.g., medication) is moved into and out of second balloon chamber 1591 via infusion port 1582, infusion lumen 1583, and second infusion lumen opening 1585.

While second balloon body 1590 has been illustrated as defining a plurality of pores 1592, a balloon body can define any suitable number of pores, and skilled artisans will be able to select a suitable number of pores for a balloon body to define according to a particular embodiment based on various considerations, including the treatment desired to be performed. Example number of pores considered suitable to include on a balloon include, but are not limited to, one, at least one, two, a plurality, three, four, five, six, seven, and any other number considered suitable for a particular application.

Second balloon 1581 can be formed of any suitable material, and skilled artisans will be able to select a suitable material to form a balloon according to a particular embodiment based on various considerations, including the materials that form an elongate member. Example materials considered suitable to form a balloon include, but are not limited to, those described above with respect to balloon 18. For example, a first balloon can be formed of a first material and a second balloon can be formed of a second material. The first material and the second material can be the same material or different.

Second balloon proximal junction 1586 and second balloon distal junction 1587 can comprise any suitable method of attachment between ventilation tube 1560 and second balloon 1581, and skilled artisans will be able to select a suitable method of attachment between a balloon and a ventilation tube according to a particular embodiment based on various considerations, including the material(s) that forms the ventilation tube and balloon. Example methods of attachment considered suitable between a ventilation tube and a balloon include, but are not limited to, those described above with respect to elongate member 12 and balloon 18 of medical device 10.

Additional structure can be attached to ventilation tube 1560 (e.g., infusion port 1582) to facilitate infusion of a medication into a bodily passage and/or the wall of a bodily passage, as described herein. For example, an infusion device, such as a syringe, can be operatively connected, or attached, to ventilation tube 1560 (e.g., infusion port 1582) and adapted to introduce medication into second balloon chamber 1591. Any infusion device capable of facilitating introduction of medication into a balloon chamber is considered suitable, and skilled artisans will be able to select a suitable infusion device according to a particular embodiment based on various considerations, including the procedure intended to be performed. Example infusion devices considered suitable include, but are not limited to, manually operated infusion devices, syringes, electromechanical infusion devices, pumps, and any other device considered suitable for a particular application.

While ventilation tube 1560 has been described as including a first balloon 1570 and a second balloon 1581, a ventilation tube can include any suitable number of balloons, and skilled artisans will be able to select a suitable number of balloons to include on a ventilation tube according to a particular embodiment based on various considerations, including the procedure intended to be performed. Example number of balloons considered suitable to include on a ventilation tube include, but are not limited to, one, at least one, two, a plurality, three, and any other number considered suitable for a particular application. For example, a ventilation tube can comprise a single balloon defining one or more pores as described above. When a single balloon is disposed on the distal end of a ventilation tube, the ventilation tube can comprise an infusion port and define an infusion lumen in communication with the single balloon.

In use, ventilation tube 1560 is passed through device lumen 1434 to move elongate member 1416 from the first, non-expanded configuration to the second, expanded configuration. Ventilation tube 1560 can be partially disposed within device lumen 1434, or separate from the elongate member 1412 and inserted into the device lumen 1434, and balloon 1570 can be in the deflated configuration, or a partially inflated configuration. As ventilation tube 1560 is axially advanced through device lumen 1434, ventilation tube body 1566 contacts elongate member body 1424 and moves elongate member 1416 from the first, non-expanded configuration to the second, expanded configuration. The first portion of elongate member axial length 1440 is sized and configured to adapt to the inflated configuration of first balloon 1570 and second balloon 1580. This can be accomplished using any suitable structural configuration, such as those described herein with respect to elongate member 12.

Any of the herein described medical devices can include a ventilation tube that has a structural arrangement similar to ventilation tube 1560 and skilled artisans will be able to select a suitable medical device to include a ventilation tube, such as ventilation tube 1560, according to a particular embodiment based on various considerations, including the structural arrangement at a point of treatment. Example medical devices considered suitable to include a ventilation tube, such as ventilation tube 1560, include medical device 10, medical device 110, medical device 210, medical device 310, medical device 810, medical device 810', medical device 1110, medical device 1410, medical device 1810, and medical devices that include a ventilation tube such as ventilation tube 60', or ventilation tube 1560. Thus, any of the herein described medical devices can include a ventilation tube that defines a ventilation tube lumen, an inflation lumen, and an infusion lumen and that has a first balloon and second balloon disposed along its length.

Figure 16:
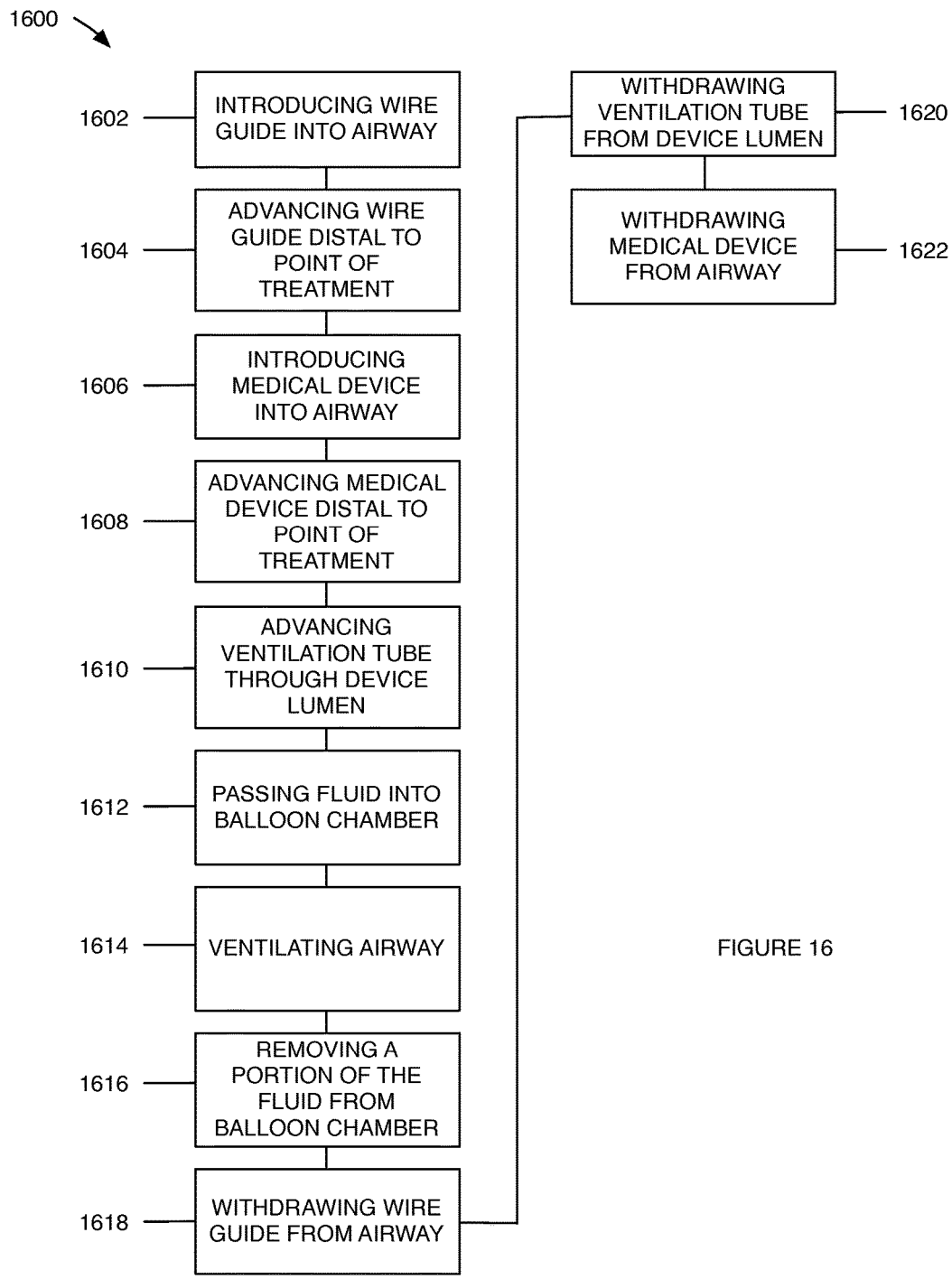
FIG. 16 is a flowchart representation of another exemplary method of providing access to a bodily passage during dilation.

FIG. 16 is a flowchart representation of an exemplary method 1600 of providing access to an airway during dilation.

A step 1602 comprises introducing a wire guide having a wire guide proximal end and a wire guide distal into an airway such that the wire guide distal end is disposed within the airway. Another step 1604 comprises advancing the wire guide distal end distal to, or beyond, a point of treatment within the airway. The point of treatment comprising a stricture within the airway. Another step 1606 comprises advancing a medical device having a medical device proximal end and a medical device distal end over the wire guide and into the airway such that the medical device distal end is disposed within the airway. An exemplary medical device considered suitable to perform one or more steps described in method 1600, or any other method or step described herein, is medical device 1410. Another step 1608 comprises advancing the medical device distally over the wire guide and into the airway such that the medical device distal end is disposed distal to, or beyond, the point of treatment. Another step 1610 comprises advancing a ventilation tube having a ventilation tube proximal end and a ventilation tube distal end over the wire guide and through the device lumen such that the ventilation tube distal end is disposed distal to the elongate member distal end. Exemplary ventilation tubes considered suitable to perform one or more steps described in method 1600, or any other method or step described herein, include ventilation tube 1460 and ventilation tube 1560. Another step 1612 comprises passing fluid into the balloon chamber. Another step 1614 comprises ventilating the airway. Another step 1616 comprises removing a portion, or the entirety, of the fluid from the balloon chamber. Another step 1618 comprises withdrawing the wire guide from the airway. Another step 1620 comprises withdrawing the ventilation tube from the device lumen. Another step 1622 comprises withdrawing the medical device from the airway.

Step 1602 is accomplished as described above with respect to step 702. Step 1604 is accomplished as described above with respect to step 704. While one or more of the methods described herein have been described as being accomplished using a wire guide, each of the methods, steps, alternative steps, and/or optional steps described herein can omit the inclusion of a wire guide and be accomplished without a wire guide.

Step 1606 can be accomplished by inserting the wire guide proximal end into and through the device lumen and ventilation tube lumen of medical device 1410 and placing a distally directed force on any suitable portion of the medical device 1410. In embodiments that include a dilator, such as dilator 1870, this step can be accomplished by inserting the wire guide proximal end into and through the device lumen and dilator lumen and placing a distally directed force on any suitable portion of the medical device.

While medical device 1410 has been illustrated and described as accomplishing one or more steps within method 1600, one or more of the steps within method 1600, or any other method and/or step described herein, can be accomplished using any suitable medical device having any suitable structural arrangement, and skilled artisans will be able to select a suitable medical device to complete a step and/or method according to particular embodiment based on various considerations, including the treatment intended to be performed. Example medical devices considered suitable include, but are not limited to, medical device 10, medical device 110, medical device 210, medical device 310, medical device 810, medical device 810', medical device 1110, medical device 1410, medical device 1810, medical devices that include a ventilation tube such as ventilation tube 60', or ventilation tube 1560, and any other medical device considered suitable for a particular application.

While the point of treatment has been described as a stricture within an airway, a point of treatment can comprise any suitable part, or portion, of a bodily passage and/or bodily passage wall, and skilled artisans will be able to select a suitable point of treatment to treat according to a method or step described herein based on various considerations, including the treatment intended to be performed.

Step 1608 is accomplished as described above with respect to step 708.

Step 1610 can be accomplished by placing a distally directed force on any suitable portion of ventilation tube 1460 such that ventilation tube distal end 1464 is advanced distal to, or beyond the stricture or elongate member distal end 1422. This step can be accomplished with the assistance of x-ray, direct visualization of the cannula (e.g., scope), transcutaneously, using an illuminated wire guide, a camera, or any other suitable visualization technique or through tactile feedback provided by the body of the ventilation tube. Alternatively, the distal end of a ventilation tube can be positioned proximal to the distal end of the elongate member, as illustrated in FIG. 13. Optionally, in embodiments that include a dilator, such as dilator 1870, this step can also include advancing the dilator through the ventilation tube lumen and can be accomplished by placing a distally directed force on any suitable portion of ventilation tube and/or dilator such that ventilation tube distal end and/or dilator distal end is advanced distal to, or beyond stricture or elongate member distal end.

Step 1612 can be accomplished by passing a fluid through inflation lumen and into balloon chamber to move balloon 1470 from its first, deflated configuration toward its second, inflated configuration. For example, a syringe in fluid communication with the inflation lumen can be used to introduce the fluid into balloon chamber. The amount of the exterior surface of balloon 1470 that contacts the inner surface of the elongate member (e.g., first portion of elongate member axial length 1440), and the amount of pressure exerted by the exterior surface of balloon 1470 onto the inner surface of the elongate member, will depend on the amount of fluid introduced into balloon chamber. In addition, the amount of the exterior surface of the elongate member 1412 that contacts the tissue in the passage wall, and the amount of pressure exerted by the exterior surface of the elongate member onto the tissue in the passage wall, will depend on the amount of fluid introduced into balloon chamber. FIG. 14 illustrates the balloon 1470 in the second, inflated configuration and contacting the interior surface of the elongate member 1412.

An optional step comprises continuing the step of passing a fluid through inflation lumen and into balloon chamber until a desired balloon diameter has been achieved.

Example fluids considered suitable to pass through an inflation lumen and into a balloon chamber include, but are not limited to, saline, water contrast, a mixture of one or more of saline, water, and/or contrast, and any other fluid considered suitable for a particular application.

Step 1614 can be accomplished by attaching a ventilation device to the ventilation tube (e.g., ventilation tube proximal end 1462) and activating a ventilation device (e.g., ventilator) such that fluid (e.g., oxygen) can be provided to the portion of the airway distal to balloon 1470. Optionally, this step can be omitted from method 1600. This step provides a mechanism for ventilating the airway while it is being dilated by balloon 1470. While step 1610, step 1612, and step 1614 have been described as being accomplished in a particular order, any suitable order can be used. For example, step 1610, step 1612, and step 1614 can be accomplished concurrently, step 1610 can be accomplished then step 1614 can be accomplished then step 1612 can be accomplished, or step 1612 can be accomplished then step 1610 can be accomplished then step 1614 can be accomplished. Optionally, step 1614 can be accomplished prior to step 1612 and/or during step 1612 such that ventilation is being completed prior to and/or during the balloon moving from the first, deflated configuration to the second, inflated configuration. In embodiments that include a dilator, such as dilator 1870, another optional step that can be completed prior to step 1612 and/or 1614 includes withdrawing the dilator from the ventilation tube. This optional step can be accomplished by applying a proximally directed force on any suitable portion of the dilator until it has been removed from the device lumen. Optionally, step 1618 can be completed prior to step 1612 and/or in combination with the optional step of withdrawing the dilator from the ventilation tube. Optionally, step 1614 can be continued during the completion of step 1612, step 1616, step 1620, and/or 1622 (e.g., in embodiments in which any wire guide and/or dilator being used have been withdrawn from the medical device). Optionally, step 1614 can be continued during the completion of any other step, such as the optional steps and/or alternative steps described herein. Another optional step comprises stopping the step of ventilating the airway and can be completed at any suitable time (e.g., prior to step 1620, prior to step 1622).

Step 1616 is accomplished by removing the fluid, or a portion of the fluid, passed into balloon chamber to move the balloon toward the first, deflated configuration. For example, a syringe in fluid communication with inflation lumen can be used to provide vacuum pressure to remove the fluid, or a portion of the fluid, from balloon chamber. The amount of fluid removed from balloon chamber can vary depending on the procedure. For example alternative to removing a portion of the fluid, all of the fluid, or substantially all of the fluid, can be removed from balloon chamber.

Step 1618 can be accomplished by placing a proximally directed force on any suitable portion of the wire guide such that the wire guide is withdrawn from the airway. It is considered advantageous to complete this step prior to attaching a ventilation device to ventilation tube 1460 (e.g., prior to step 1614). Alternatively, the step of withdrawing the wire guide from the airway can comprise withdrawing the wire guide from the ventilation tube lumen. Optionally, the step of withdrawing the wire guide from the airway or ventilation tube lumen can be completed prior to the step 1612 of passing a fluid into the balloon chamber.

Step 1620 can be accomplished by placing a proximally directed force on any suitable portion of the ventilation tube such that the ventilation tube is withdrawn from the airway.

Step 1622 can be accomplished by placing a proximally directed force on any suitable portion of the medical device 1410 such that the medical device 1410 is withdrawn from the airway.

While step 1618, step 1620, and 1622 have been described as separate steps, step 1618, step 1620, and step 1622 can be accomplished concurrently with one another.

While method 1600 has been illustrated and described as being accomplished using a wire guide, any of the steps, optional steps, and/or alternative steps described herein can be accomplished without a wire guide.

In the illustrated embodiment, it is considered advantageous to complete method 1600 in the order illustrated and/or described. It is noted, however, that any order is considered suitable, as described herein.

While ventilation tube 1460 has been described as being advanced through device lumen, any suitable medical device can be passed through device lumen, and skilled artisans will be able to select a suitable medical device according to a particular embodiment based on various considerations, including the treatment intended to be performed. Example devices considered suitable to pass through a device lumen include, but are not limited to, elongate members, ventilation tubes (e.g., ventilation tube 60, ventilation tube 60', ventilation tube 1460, ventilation tube 1560), suction catheters, balloon catheters, irrigation catheters, a camera and/or light source disposed on an elongate member, and any other device considered suitable for a particular application.

While various steps, alternative steps, and optional steps have been described above with respect to providing access to an airway, these steps, alternative steps, and optional steps can be included in, accomplished concurrently with, and/or accomplished in the alternative to, the methods, steps, alternative steps, and/or optional steps described above and/or below with respect to providing access to an airway.

Figure 17:
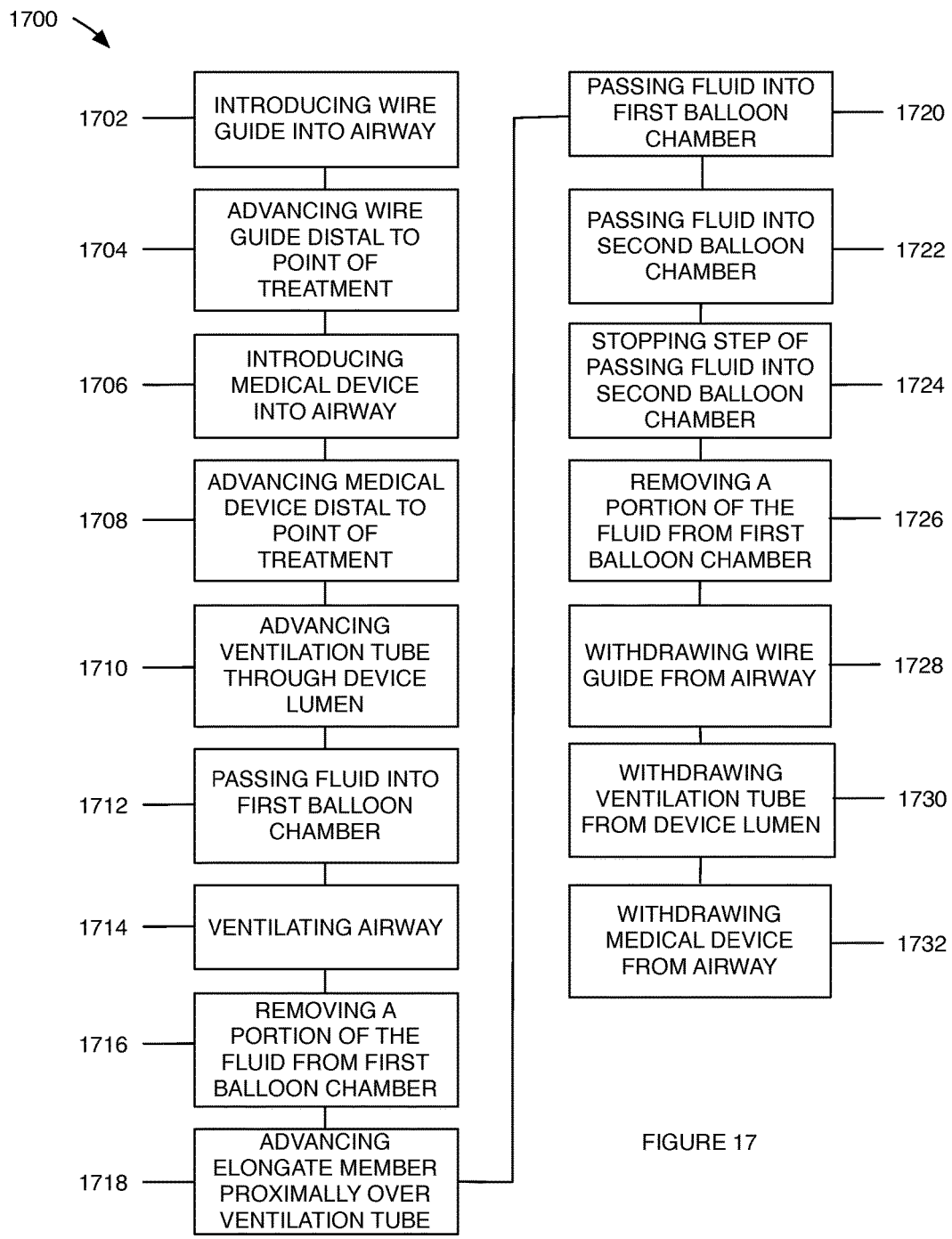
FIG. 17 is a flowchart representation of another exemplary method of providing access to a bodily passage during dilation.

FIG. 17 is a flowchart representation of an exemplary method 1700 of providing access to an airway during dilation.

A step 1702 comprises introducing a wire guide having a wire guide proximal end and a wire guide distal into an airway such that the wire guide distal end is disposed within the airway. Another step 1704 comprises advancing the wire guide distal end distal to, or beyond, a point of treatment within the airway. The point of treatment comprising a stricture within the airway. Another step 1706 comprises advancing a medical device having a medical device proximal end and a medical device distal end over the wire guide and into the airway such that the medical device distal end is disposed within the airway. An exemplary medical device considered suitable to perform one or more steps described in method 1700, or any other method or step described herein, is medical device 1410 that includes ventilation tube 1560. Ventilation tube 1560 has a first balloon and a second balloon. Another step 1708 comprises advancing the medical device distally over the wire guide and into the airway such that the medical device distal end is disposed distal to, or beyond, the point of treatment. Another step 1710 comprises advancing a ventilation tube having a ventilation tube proximal end and a ventilation tube distal end over the wire guide and through the device lumen such that the ventilation tube distal end is disposed distal to the elongate member distal end. Another step 1712 comprises passing fluid into the first balloon chamber. Another step 1714 comprises ventilating the airway. Another step 1716 comprises removing a portion, or the entirety, of the fluid from the first balloon chamber. Another step 1718 comprises advancing the elongate member proximally over the ventilation tube and out of the airway. Another step 1720 comprises passing fluid into the first balloon chamber. Another step 1722 comprises passing a fluid into the second balloon chamber until the fluid is expelled from one or more of the pores defined by second balloon wall. Another step 1724 comprises stopping the step of passing fluid into the second balloon chamber. Another step 1726 comprises removing a portion, or the entirety, of the fluid from the first balloon chamber. Another step 1728 comprises withdrawing the wire guide from the airway. Another step 1730 comprises withdrawing the ventilation tube from the device lumen. Another step 1732 comprises withdrawing the medical device from the airway.

Step 1702 is accomplished as described above with respect to step 702. Step 1704 is accomplished as described above with respect to step 704. While one or more of the methods described herein have been described as being accomplished using a wire guide, each of the methods, steps, alternative steps, and/or optional steps described herein can omit the inclusion of a wire guide and be accomplished without a wire guide.

Step 1706 can be accomplished by inserting the wire guide proximal end into and through the device lumen and ventilation tube lumen 1568 of medical device 1410 and placing a distally directed force on any suitable portion of the medical device 1410. In embodiments that include a dilator, such as dilator 1870, this step can be accomplished by inserting the wire guide proximal end into and through the device lumen and dilator lumen and placing a distally directed force on any suitable portion of the medical device.

While medical device 1410 and ventilation tube 1560 have been described as accomplishing one or more steps within method 1700, one or more of the steps within method 1700, or any other method and/or step described herein, can be accomplished using any suitable medical device having any suitable structural arrangement, and skilled artisans will be able to select a suitable medical device to complete a step and/or method according to particular embodiment based on various considerations, including the treatment intended to be performed. Example medical devices considered suitable include, but are not limited to, medical device 10, medical device 110, medical device 210, medical device 310, medical device 810, medical device 810', medical device 1110, medical device 1410, medical device 1810, medical devices that include a ventilation tube such as ventilation tube 60', or ventilation tube 1560, and any other medical device considered suitable for a particular application.

While the point of treatment has been described as a stricture within an airway in the methods described herein, a point of treatment can comprise any suitable part, or portion, of a bodily passage and/or bodily passage wall, and skilled artisans will be able to select a suitable point of treatment to treat according to a method or step described herein based on various considerations, including the treatment intended to be performed. Therefore, alternative to a wire guide and medical device being introduced into an airway, a wire guide and/or medical device can be advanced into a bodily passage.

Step 1708 is accomplished as described above with respect to step 708.

Step 1710 can be accomplished by placing a distally directed force on any suitable portion of ventilation tube 1560 such that ventilation tube distal end 1564 is advanced distal to, or beyond the stricture or elongate member distal end 1422. This step can be accomplished with the assistance of x-ray, direct visualization of the cannula (e.g., scope), transcutaneously, using an illuminated wire guide, a camera, or any other suitable visualization technique or through tactile feedback provided by the body of the ventilation tube. Optionally, in embodiments that include a dilator, such as dilator 1870, this step can also include advancing the dilator through the ventilation tube lumen and can be accomplished by placing a distally directed force on any suitable portion of ventilation tube and/or dilator such that ventilation tube distal end and/or dilator distal end is advanced distal to, or beyond stricture or elongate member distal end.

Step 1712 can be accomplished by passing a fluid through inflation lumen and into the first balloon chamber to move first balloon 1570 from its first, deflated configuration toward its second, inflated configuration. For example, a syringe in fluid communication with the inflation lumen can be used to introduce the fluid into balloon chamber. The amount of the exterior surface of second balloon 1581 that contacts the inner surface of the elongate member (e.g., first portion of elongate member axial length 1440), and the amount of pressure exerted by the exterior surface of second balloon 1581 onto the inner surface of the elongate member, will depend on the amount of fluid introduced into the first balloon chamber 1580. In addition, the amount of the exterior surface of the elongate member 1412 that contacts the tissue in the passage wall, and the amount of pressure exerted by the exterior surface of the elongate member onto the tissue in the passage wall, will depend on the amount of fluid introduced into balloon chamber.

An optional step comprises continuing the step of passing a fluid through inflation lumen and into balloon chamber until a desired balloon diameter has been achieved. Another optional step comprises stopping the step of passing a fluid through the inflation lumen and into the first balloon chamber.

Example fluids considered suitable to pass through an inflation lumen and into a balloon chamber include, but are not limited to, saline, water contrast, a mixture of one or more of saline, water, and/or contrast, and any other fluid considered suitable for a particular application.

Step 1714 can be accomplished by attaching a ventilation device to the ventilation tube 1560 (e.g., ventilation tube proximal end 1562) and activating the ventilation device (e.g., ventilator) such that fluid (e.g., oxygen) is provided to the portion of the airway distal to first balloon 1570 and second balloon 1581. This step provides a mechanism for ventilating the airway while it is being dilated by first balloon 1570 and second balloon 1581. While step 1710, step 1712, and step 1714 have been described as being accomplished in a particular order, any suitable order can be used. For example, step 1710, step 1712, and step 1714 can be accomplished concurrently, step 1710 can be accomplished then step 1714 can be accomplished then step 1712 can be accomplished, or step 1712 can be accomplished then step 1710 can be accomplished then step 1714 can be accomplished. Optionally, step 1714 can be accomplished prior to step 1712 and/or during step 1712 such that ventilation is being completed prior and/or during the balloon moving from the first, deflated configuration to the second, inflated configuration. In embodiments that include a dilator, such as dilator 1870, another optional step that can be completed prior to step 1712 and/or 1714 includes withdrawing the dilator from the ventilation tube. This optional step can be accomplished by applying a proximally directed force on any suitable portion of the dilator until it has been removed from the device lumen. Optionally, step 1728 can be completed prior to step 1712 and/or in combination with the optional step of withdrawing the dilator from the ventilation tube. Optionally, step 1714 can be continued during the completion of step 1712, step 1716, step 1718, step 1720, step 1722, step 1724, step 1726, step 1730, and/or step 1732 (e.g., in embodiments in which any wire guide and/or dilator being used have been withdrawn from the medical device). Optionally, step 1714 can be continued during the completion of any other step, such as the optional steps and/or alternative steps described herein. Another optional step comprises stopping the step of ventilating the airway and can be completed at any suitable time (e.g., prior to step 1730, prior to step 1732).

Step 1716 is accomplished as described above with respect to step 1616.

Step 1718 can be accomplished by placing a proximally directed force on the elongate member 1412 such that it is advanced proximally over the ventilation tube 1560 and out of the airway. The proximally directed force can be applied until the elongate member 1412 is fully withdrawn from the airway, partially withdrawn from the airway, or such that the distal end of the elongate member 1412 is disposed proximal to the point of treatment (e.g., stricture), the first balloon 1570, and/or second balloon 1581 of the ventilation tube 1560. An optional step comprises stopping the step of advancing the elongate member proximally over the ventilation tube and out of the airway, which can be accomplished by terminating the application of a proximally directed force on the elongate member. This optional step can be completed, for example, once the elongate member has been completely removed from the airway, when the elongate member has been completely removed from being disposed over the ventilation tube or second balloon 1581, or when the elongate member has been completely withdrawn from over the wire guide.

Step 1720 can be accomplished by passing a fluid, such as those described herein, through inflation lumen and into balloon chamber to move first balloon 1570 from its first, deflated configuration toward its second, inflated configuration. For example, a syringe in fluid communication with the inflation lumen can be used to introduce the fluid into first balloon chamber. The amount of the exterior surface of second balloon 1581 that contacts the tissue in the passage wall, and the amount of pressure exerted by the exterior surface of second balloon 1581 onto the tissue in the passage wall, will depend on the amount of fluid introduced into first balloon chamber 1580. An optional step comprises continuing the step of passing a fluid through inflation lumen and into balloon chamber until a desired balloon diameter has been achieved.

An optional step that can be completed prior to any step described herein regarding passing a fluid through an infusion lumen comprises confirming that one or more of the pores are aligned, or positioned adjacent, a point of treatment (e.g., stricture). This can be accomplished using any suitable visualization technique, such as those described herein (e.g., by visualizing one or more markers disposed adjacent one or more pores define by the body of a balloon).

Step 1722 can be accomplished by passing a fluid (e.g., medication), such as those described herein, through infusion lumen 1583 and into the second balloon chamber 1591 such that the fluid can be expelled from one or more of the plurality of pores 1592. Optionally, any step described herein regarding passing fluid through an infusion lumen can also comprise passing fluid through an infusion lumen such that the fluid is infused into and/or coats the tissue that is contacting, or adjacent, the exterior surface of the balloon. For example, a syringe in fluid communication with the infusion lumen 1583 can be used to introduce the fluid into the second balloon chamber 1591. The amount of fluid passed through each pore of the plurality of pores 1592, and the amount of pressure exerted by the exterior surface of second balloon 1581 onto the tissue in the passage wall, will depend on the amount of fluid introduced into the first balloon chamber 1580 and the second balloon chamber 1591.

Step 1724 can be accomplished by terminating the passing of the fluid through the infusion lumen 1583 and into the second balloon chamber 1591. When a syringe is being used to pass fluid into the infusion lumen, this step can be accomplished by removing the pressure from the plunger of the syringe.

Step 1726 is accomplished as described above with respect to step 1616.

Step 1728 is accomplished as described above with respect to 1618.

Step 1730 is accomplished as described above with respect to 1620.

Step 1732 is accomplished as described above with respect to 1622.

While step 1728, step 1730, and 1732 have been described as separate steps, step 1728, step 1730, and step 1732 can be accomplished concurrently with one another.

Optionally, step 1716, step 1718, step 1720, step 1722, step 1724, step 1726, step 1728, step 1730, and/or step 1732 can be accomplished in combination with step 1714 such that ventilation occurs during the completion of one or more of these steps. Alternatively, step 1716, step 1718, step 1720, step 1722, step 1724, step 1726, step 1728, step 1730, and/or step 1732 can be accomplished after step 1714 has been completed.

While method 1700 has been illustrated and described as being accomplished using a wire guide, any of the steps, optional steps, and/or alternative steps described herein can be accomplished without a wire guide.

In the illustrated embodiment, it is considered advantageous to complete method 1700 in the order illustrated and/or described. It is noted, however, that any order is considered suitable, as described herein.

While ventilation tube 1560 has been described as being advanced through device lumen, any suitable medical device can be passed through device lumen, and skilled artisans will be able to select a suitable medical device according to a particular embodiment based on various considerations, including the treatment intended to be performed. Example devices considered suitable to pass through a device lumen include, but are not limited to, elongate members, ventilation tubes, such as those described herein, suction catheters, balloon catheters, irrigation catheters, dilators, such as those described herein, a camera and/or light source disposed on an elongate member, and any other device considered suitable for a particular application.

While various steps, alternative steps, and optional steps have been described above with respect to providing access to an airway, these steps, alternative steps, and optional steps can be included in, accomplished concurrently with, and/or accomplished in the alternative to, the methods, steps, alternative steps, and/or optional steps described above and/or below with respect to providing access to an airway.

Figure 18:
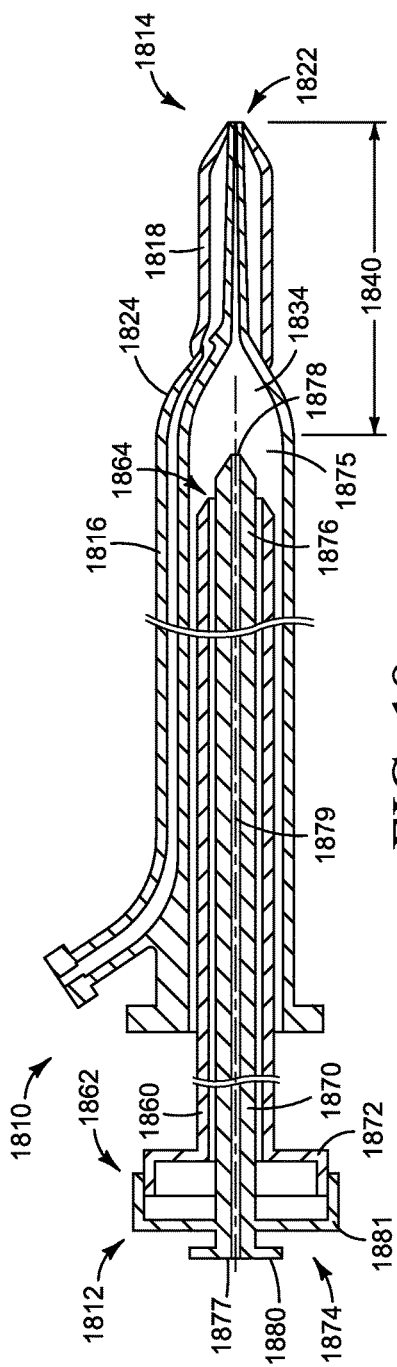
FIG. 18 is a sectional view of a ninth exemplary medical device is a first, non-expanded configuration with an associated balloon in a first, deflated configuration.
Figure 19:
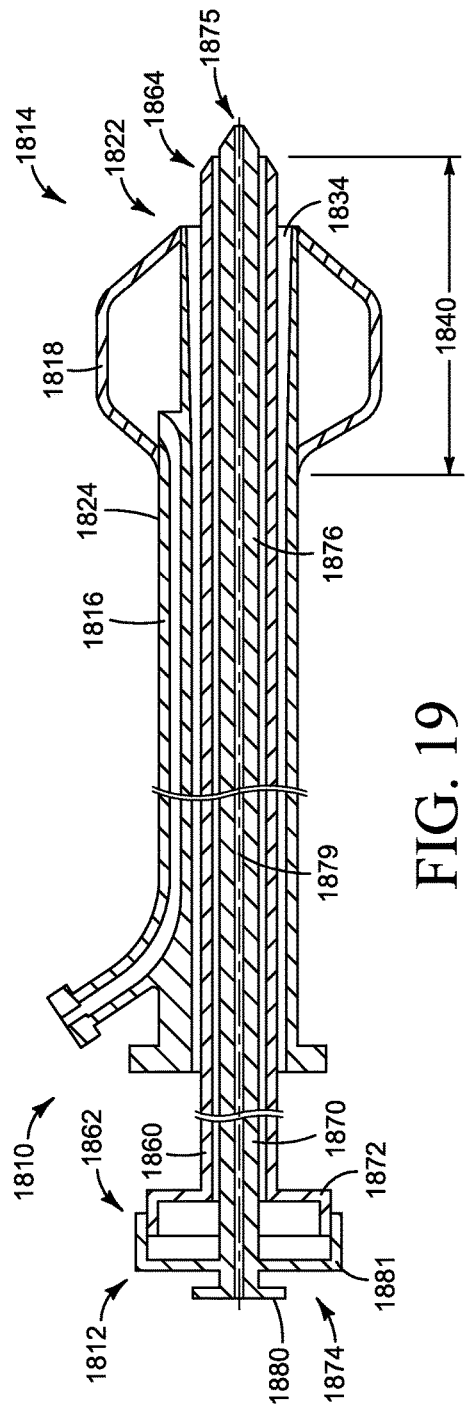
FIG. 19 is a sectional view of the medical device illustrated in FIG. 18 in a second, expanded configuration with the associated balloon in a second, inflated configuration.

FIGS. 18 and 19 illustrate a ninth exemplary medical device 1810. Medical device 1810 is similar to medical device 10 illustrated in FIGS. 1 and 2 and described above, except as detailed below. Reference numbers in FIGS. 18 and 19 refer to the same structural element or feature referenced by the same number in FIGS. 1 and 2, offset by 1800. Thus, medical device 1810 has a medical device proximal end 1812 and a medical device distal end 1814. In the illustrated embodiment, medical device 1810 comprises an elongate member 1816, a balloon 1818, a ventilation tube 1860, and a dilator 1870. Medical device 1810 is adapted to move between a first, non-expanded configuration and a second, expanded configuration.

In the illustrated embodiment, the ventilation tube proximal end 1862 defines a connector 1872 that is adapted to be releasably attached to a dilator, such as dilator 1870, and/or a ventilation device. In addition, the ventilation tube distal end 1864 is tapered. Connector 1872 can comprise any suitable connector, such as those described herein. For example, connector 1872 can comprise a conical connector (e.g., cone, socket), such as those described in document BS (British Standards) EN ISO 5356-1:2004, that is adapted to be attached to a ventilation device, or a component in communication with a ventilation device (e.g., tubular member).

In the illustrated embodiment, dilator 1870 comprises a proximal end 1874, a tapered distal end 1875, and a body 1876 that defines a first opening 1877, a second opening 1878, a dilator lumen 1879, a proximal fitting 1880, and a ventilation tube fitting 1881. The dilator 1870 is adapted to be releasably attached to the ventilation tube 1860. In the embodiment illustrated, the dilator has a length that is greater than the length of the ventilation tube 1860. The dilator lumen 1879 extends from the first opening 1877 to the second opening 1878 and is sized and configured to receive a wire guide, such as those described herein. Alternatively, a dilator lumen 1879 can be omitted from a dilator. Proximal fitting 1880 is disposed on the proximal end 1874 of the dilator 1870 and can include any suitable connector, such as those described herein. Optionally, a proximal fitting, such as proximal fitting 1880, can be omitted from a dilator. Ventilation tube fitting 1881 is sized and configured to be received by the connector 1872 of the ventilation tube 1860 and can comprise any suitable structure, such as that illustrated, capable of providing releasable attachment between a dilator and a ventilation tube. Optionally, the ventilation tube fitting 1881 can be omitted from a dilator such that the dilator is free of the ventilation tube.

In the embodiment illustrated, the angle of the taper defined on ventilation tube distal end 1864 is equal to the angle of the tapered distal end 1875 of the dilator 1870 relative to the lengthwise axis of the elongate member 1812. Alternatively, the angle of the taper defined on ventilation tube distal end can be greater than, less than, or substantially equal to, the angle of the tapered distal end of the dilator relative to the lengthwise axis of the elongate member. Any of the ventilation tubes (e.g., ventilation tube 60, ventilation tube 160, ventilation tube 260, ventilation tube 390, ventilation tube 1460, ventilation tube 1560) described herein can include the structure illustrated and described as being included on ventilation tube 1860.

Dilator 1870 can be formed of any suitable material, and skilled artisans will be able to select a suitable material for a dilator according to a particular embodiment based on various considerations, including the desired flexibility of the dilator. Example materials considered suitable to form a dilator include, but are not limited to, biocompatible materials, materials that can be made biocompatible, metals such as stainless steel, titanium, nickel-titanium alloys (e.g., Nitinol), polymers, Pebax (Pebax is a registered trademark of Ato Chimie Corporation of Allee des Vosges, Courbevoie, France), nylon, polyethylene, polyurethane, polytetrafluoroethylene (PTFE), ePTFE, silicone, coiled materials, braided materials, and any other material considered suitable for a particular application. Optionally, the tapered distal end 1875 can be formed of a material that is more flexible than the material that forms the remaining length of the dilator 1870. For example, a first portion of the dilator 1870 that extends from the proximal end toward the distal end can be formed of a first material (e.g., metal, rigid plastic) and the tapered distal end 1875 can be formed of a second material (e.g., polymer, atraumatic material). The second material can be the same as, or different from, the first material and is more flexible than the first material.

FIG. 18 illustrates ventilation tube distal end 1864 and dilator distal end 1875 disposed proximal to the first portion of elongate member axial length 1840 and elongate member 1816 in the first, non-expanded configuration. Thus, ventilation tube 1860 and dilator 1870 are partially disposed within device lumen 1834. FIG. 19 illustrates ventilation tube distal end 1864 and dilator distal end 1875 disposed distal to elongate member distal end 1822 and elongate member 1816 in the second, expanded configuration. As ventilation tube 1860 and dilator 1870 are axially advanced through device lumen 1834, ventilation tube body 1866 and dilator body 1876 contacts elongate member body 1824 and moves elongate member 1816 from the first, non-expanded configuration to the second, expanded configuration. In the illustrated embodiment, as ventilation tube 1860 and dilator 1870 are axially advanced through device lumen 1834, ventilation tube body 1866 and dilator 1870 contacts the first portion of elongate member axial length 1840 and moves elongate member 1816 from the first, non-expanded configuration to the second, expanded configuration. It is considered advantageous for ventilation tube 1860 and dilator 1870 to have an axial length that is greater than the axial length of elongate member 1816 at least because when the ventilation tube proximal end 1862 contacts the elongate member proximal end 1820 the ventilation tube distal end 1864 and dilator distal end 1875 are each disposed distal to elongate member distal end 1822 or disposed distal to the balloon distal end 1850. While FIG. 19 illustrates the ventilation tube distal end 1864 and dilator distal end 1875 disposed distal to the elongate member distal end 1822, a ventilation tube and dilator can be advanced any suitable distance through a device lumen. For example, ventilation tube and/or dilator can be advanced such that the ventilation tube distal end and/or dilator distal end is disposed distal to, proximal to, adjacent, or coaxial with the elongate member distal end.

While balloon 1818 has been illustrated as disposed on elongate member 1812, elongate member 1812 can optionally omit the inclusion of an attached balloon 1818, an inflation port 1826, and an inflation lumen 1830. Connector 1872 and/or dilator 1870 can be used in combination with any of the medical devices, ventilation tubes, and/or dilators described herein to provide a mechanism for attaching a ventilation tube to another device and/or advancing the ventilation tube through a lumen, such as device lumen 1834, to advance an elongate member from its first, non-expanded configuration to its second, expanded configuration. Example medical devices considered suitable to include a connector, such as connector 1872, and/or dilator, such as dilator 1870, include any of the medical device described herein, such as medical device 10, medical device 110, medical device 210, medical device 310, medical device 810, medical device 810', medical device 1110, medical device 1410, medical devices that include a ventilation tube such as ventilation tube 60', or ventilation tube 1560, and any other medical device considered suitable for a particular application.

While ventilation tube 1860 has been illustrated as having a particular structural configuration, a ventilation tube, such as ventilation tube 1860, can have any suitable structural configuration and include any of the features, elements, and/or components described herein as being included on a ventilation tube and/or dilator. Skilled artisans will be able to select a suitable feature, element, and/or component to include on a ventilation tube according to a particular embodiment based on various considerations. For example, a ventilation tube, such as ventilation tube 1860, can include structure such as that described with respect to ventilation tube 1460. In this embodiment, the ventilation tube, such as ventilation tube 1860, can include an inflation port (e.g., inflation port 1471), inflation lumen (e.g., inflation lumen 1472), and a balloon (e.g., balloon 1470). Alternatively, a ventilation tube, such as ventilation tube 1860, can include structure such as that described with respect to ventilation tube 1560. In this embodiment, the ventilation tube, such as ventilation tube 1860, can include an inflation port (e.g., inflation port 1571), inflation lumen (e.g., inflation lumen 1572), a first balloon (e.g., first balloon 1570), an infusion port (e.g., infusion port 1582), an infusion lumen (e.g., infusion lumen 1583), and a second balloon (e.g., second balloon 1580).

Figure 20:
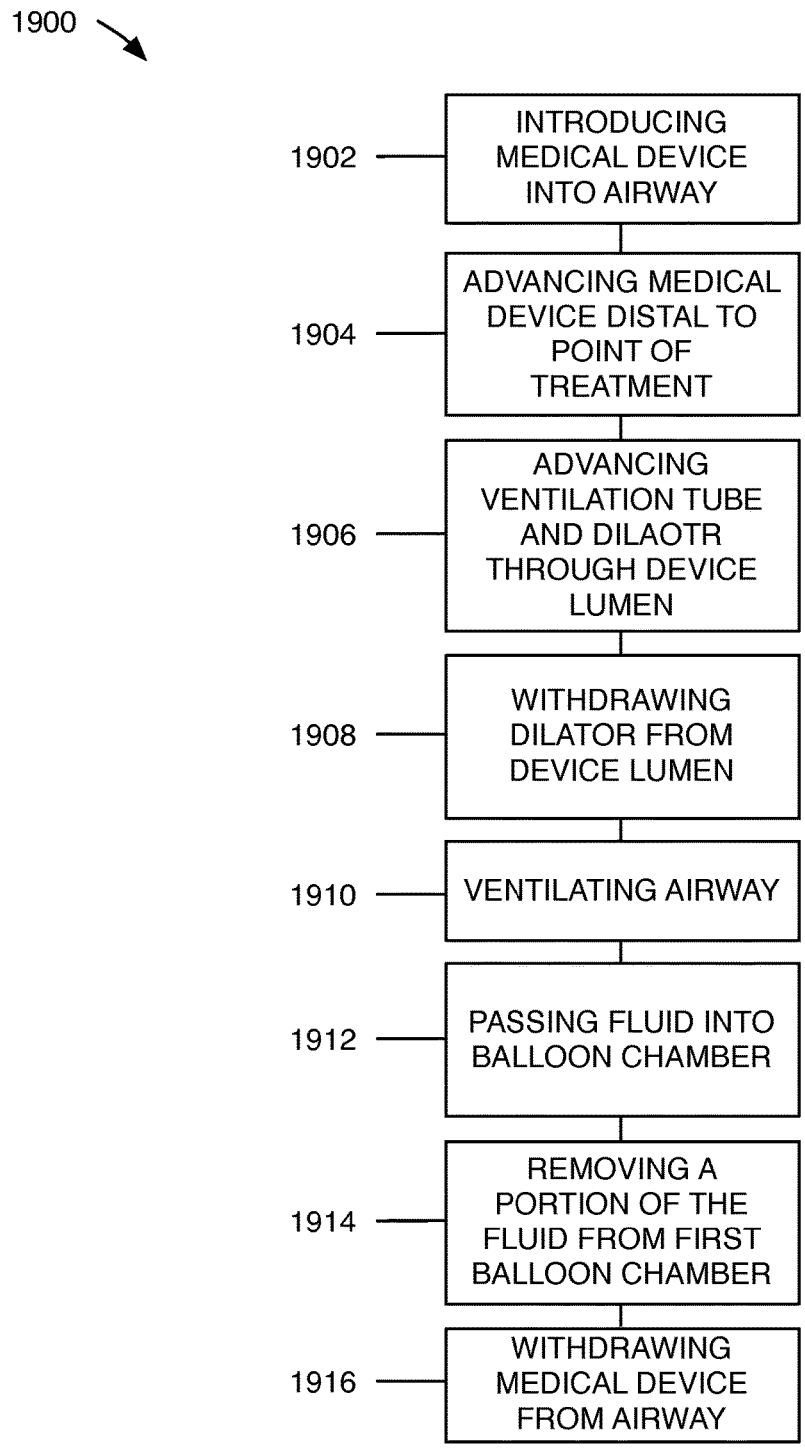
FIG. 20 is a flowchart representation of another exemplary method of providing access to a bodily passage during dilation.

FIG. 20 is a flowchart representation of an exemplary method 1900 of providing access to an airway during dilation.

A step 1902 comprises advancing a medical device having a medical device proximal end and a medical device distal end into the airway such that the medical device distal end is disposed within the airway. An exemplary medical device considered suitable to perform one or more steps described in method 1900, or any other method or step described herein, is medical device 1810 that includes a ventilation tube 1860 and a dilator 1870. Another step 1904 comprises advancing the medical device distally into the airway such that the medical device distal end is disposed distal to, or beyond, the point of treatment. The point of treatment comprising a stricture within the airway. Another step 1906 comprises advancing the ventilation tube and the dilator through the device lumen such that the ventilation tube distal end and the dilator distal end are disposed distal to the elongate member distal end. Another step 1908 comprises withdrawing the dilator from the device lumen. Another step 1910 comprises ventilating the airway. Another step 1912 comprises passing fluid into the balloon chamber. Another step 1914 comprises removing a portion, or the entirety, of the fluid from the balloon chamber. Another step 1916 comprises withdrawing the medical device from the airway.

While method 1900 has been illustrated and described as being accomplished without the use of a wire guide, method 1900 can optionally be completed using a wire guide and can include one or more of the steps relating to use of a wire guide, such as those described herein.

Step 1902 can be accomplished by placing a distally directed force on any suitable portion of the medical device 1810. While medical device 1810, ventilation tube 1860, and dilator 1870 have been described as accomplishing one or more steps within method 1900, one or more of the steps within method 1900, or any other method and/or step described herein, can be accomplished using any suitable medical device having any suitable structural arrangement, and skilled artisans will be able to select a suitable medical device to complete a step and/or method according to particular embodiment based on various considerations, including the treatment intended to be performed. Example medical devices considered suitable include, but are not limited to, medical device 10, medical device 110, medical device 210, medical device 310, medical device 810, medical device 810', medical device 1110, medical device 1410, medical devices that include a ventilation tube such as ventilation tube 60', or ventilation tube 1560, and any other medical device considered suitable for a particular application. In embodiments that include a wire guide, this step can be accomplished by advancing the proximal end of the wire guide through the lumen defined by the dilator and by placing a distally directed force on any suitable portion of the medical device 1810.

While the point of treatment has been described as a stricture within an airway in the methods described herein, a point of treatment can comprise any suitable part, or portion, of a bodily passage and/or bodily passage wall, and skilled artisans will be able to select a suitable point of treatment to treat according to a method or step described herein based on various considerations, including the treatment intended to be performed. Therefore, alternative to a medical device being introduced into an airway, a medical device can be advanced into a bodily passage.

Step 1904 is accomplished as described above with respect to step 708.

Step 1906 can be accomplished by placing a distally directed force on any suitable portion of ventilation tube 1860 and/or dilator 1870 such that the ventilation tube distal end 1864 and/or dilator distal end 1875 is advanced distal to, or beyond the stricture or elongate member distal end 1822. This step can be accomplished with the assistance of x-ray, direct visualization of the cannula (e.g., scope), transcutaneously, using an illuminated wire guide, a camera, or any other suitable visualization technique or through tactile feedback provided by the body of the ventilation tube and/or dilator. Optionally, step 1906 can be completed in two separate steps. A first step comprises advancing the dilator through the device lumen such that the dilator distal end is disposed proximal to, distal to, or adjacent the elongate member distal end. A second step comprises advancing the ventilation tube through the device lumen such that the ventilation tube distal end is disposed proximal to, distal to, or adjacent the elongate member distal end or the dilator distal end.

Step 1908 can be accomplished by placing a proximally directed force on any suitable portion of the dilator such that the dilator is withdrawn from the elongate member and the airway and the dilator distal end is disposed proximal to the elongate member proximal end and the ventilation tube distal end.

Step 1910 can be accomplished by attaching a ventilation device to the ventilation tube 1860 (e.g., connector 1872) and activating the ventilation device (e.g., ventilator) such that fluid (e.g., oxygen) is provided to the portion of the airway distal to the elongate member proximal end. This step provides a mechanism for ventilating the airway while it is being dilated. Optionally, step 1910 can be continued during the completion of step 1912, step 1914, and/or step 1916 (e.g., in embodiments in which any wire guide and/or dilator being used have been withdrawn from the medical device). Optionally, step 1910 can be continued during the completion of any other step, such as the optional steps and/or alternative steps described herein. Another optional step comprises stopping the step of ventilating the airway and can be completed at any suitable time (e.g., prior to step 1916).

Step 1912 can be accomplished by passing a fluid through inflation lumen and into the balloon chamber to move the balloon 1860 from its first, deflated configuration toward its second, inflated configuration. For example, a syringe in fluid communication with the inflation lumen can be used to introduce the fluid into balloon chamber. The amount of the exterior surface of the balloon 1860 that contacts the tissue in the passage wall, and the amount of pressure exerted by the exterior surface of the elongate member onto the tissue in the passage wall, will depend on the amount of fluid introduced into balloon chamber. An optional step comprises continuing the step of passing a fluid through inflation lumen and into balloon chamber until a desired balloon diameter has been achieved. Another optional step comprises stopping the step of passing a fluid through the inflation lumen and into the first balloon chamber. Example fluids considered suitable to pass through an inflation lumen and into a balloon chamber include, but are not limited to, saline, water contrast, a mixture of one or more of saline, water, and/or contrast, and any other fluid considered suitable for a particular application.

Step 1914 is accomplished as described above with respect to step 1616.

Step 1916 can be accomplished by placing a proximally directed force on any suitable portion of the medical device 1810 such that the medical device 1810 (e.g., elongate member and ventilation tube) is withdrawn from the airway.

In the illustrated embodiment, it is considered advantageous to complete method 1900 in the order illustrated and/or described. It is noted, however, that any order is considered suitable, as described herein.

While ventilation tube 1860 and dilator 1870 have been described as being advanced through device lumen, any suitable medical device can be passed through device lumen, and skilled artisans will be able to select a suitable medical device according to a particular embodiment based on various considerations, including the treatment intended to be performed. Example devices considered suitable to pass through a device lumen include, but are not limited to, elongate members, ventilation tubes, such as those described herein, suction catheters, balloon catheters, irrigation catheters, dilators, such as those described herein, a camera and/or light source disposed on an elongate member, and any other device considered suitable for a particular application.

While various steps, alternative steps, and optional steps have been described above with respect to providing access to an airway, these steps, alternative steps, and optional steps can be included in, accomplished concurrently with, and/or accomplished in the alternative to, the methods, steps, alternative steps, and/or optional steps described above with respect to providing access to an airway.

The foregoing detailed description provides exemplary embodiments of the invention and includes the best mode for practicing the invention. The description and illustration of embodiments is intended only to provide examples of the invention, and not to limit the scope of the invention, or its protection, in any manner.

What is claimed is:

1. A medical device comprising:
   an elongate member having an elongate member proximal end, an elongate member distal end having a distal terminal end, an elongate member axial length extending from the elongate member proximal end to the distal terminal end, a device lumen extending through the elongate member, an inflation lumen, and an elongate member body having a first wall thickness and a second wall thickness, a first portion of the elongate member axial length extending from the distal terminal end toward the elongate member proximal end and a second portion of the elongate member axial length extending from the elongate member proximal end to the first portion of the elongate member axial length, the first wall thickness disposed on the first portion of the elongate member axial length and the second wall thickness disposed on the second portion of the elongate member axial length, the first wall thickness being less than the second wall thickness, the first portion of the elongate member axial length adapted to move between a first, non-expanded configuration and a second, expanded configuration, the distal terminal end having a first outside diameter when in the first, non-expanded configuration and a second outside diameter when in the second, expanded configuration, the second outside diameter being greater than the first outside diameter; and
   a balloon disposed on at least a portion of the first portion of the elongate member axial length, the balloon having a balloon chamber in communication with the inflation lumen and adapted to move between a first, deflated configuration and a second, inflated configuration as fluid moves into and out of the balloon chamber.

2. The medical device of claim 1, wherein the balloon is disposed entirely on the first portion of the elongate member axial length.

3. The medical device of claim 1, wherein the first portion of the elongate member axial length is formed of a first material;
   wherein the second portion of the elongate member axial length is formed of a second material; and
   wherein the first material is different from the second material.

4. The medical device of claim 1, wherein the balloon has a balloon wall that defines a plurality of pores, each pore of the plurality of pores extending through the balloon wall and providing access to the balloon chamber.

5. The medical device of claim 1, further comprising a ventilation tube partially disposed within the device lumen, the ventilation tube comprising a ventilation tube proximal end, a ventilation tube distal end, and a ventilation tube body that defines a ventilation tube lumen; and
   wherein the ventilation tube distal end is disposed proximal to the first portion of the elongate member axial length.

6. The medical device of claim 5, wherein the ventilation tube is adapted to pass through the device lumen; and
   wherein advancement of the ventilation tube distally through the device lumen moves the elongate member from the first, non-expanded configuration to the second, expanded configuration.

7. The medical device of claim 5, wherein the ventilation tube has a first outside diameter and a second outside diameter disposed distal to the first outside diameter, the first outside diameter being greater than the second outside diameter.

8. The medical device of claim 1, wherein in the first, non-expanded configuration the first portion of the elongate member axial length and the portion of the balloon disposed on the first portion of the elongate member axial length are folded.

9. The medical device of claim 1, further comprising a dilator comprising a dilator shaft and a dilator tip, the dilator shaft partially disposed within the device lumen and a portion of the dilator tip disposed distal to the elongate member distal end.

10. The medical device of claim 1, wherein the elongate member has an interior surface that defines the device lumen and an exterior surface; and
    wherein the first wall thickness extends from the interior surface to a portion of the exterior surface of the elongate member disposed within the balloon.

11. The medical device of claim 10, wherein the second wall thickness extends from the interior surface to the exterior surface of the elongate member.

12. A medical device comprising:
an elongate member having an elongate member proximal end, an elongate member distal end having a distal terminal end, an elongate member axial length extending from the elongate member proximal end to the distal terminal end, a device lumen extending through the elongate member, an inflation lumen, and an elongate member body having a first wall thickness and a second wall thickness, a first portion of the elongate member axial length extending from the distal terminal end toward the elongate member proximal end and a second portion of the elongate member axial length extending from the elongate member proximal end to the first portion of the elongate member axial length, the first wall thickness disposed on the first portion of the elongate member axial length and the second wall thickness disposed on the second portion of the elongate member axial length, the first wall thickness being less than the second wall thickness, the first portion of the elongate member axial length adapted to move between a first, non-expanded configuration and a second, expanded configuration, the distal terminal end having a first outside diameter when in the first, non-expanded configuration and a second outside diameter when in the second, expanded configuration, the second outside diameter being greater than the first outside diameter;
a balloon disposed entirely on the first portion of the elongate member axial length, the balloon having a balloon chamber in communication with the inflation lumen and adapted to move between a first, deflated configuration and a second, inflated configuration as fluid moves into and out of the balloon chamber; and
a ventilation tube partially disposed within the device lumen, the ventilation tube comprising a ventilation tube proximal end, a ventilation tube distal end, and a ventilation tube body that defines a ventilation tube lumen.

13. The medical device of claim 12, wherein the first portion of the elongate member axial length is formed of a first material;
wherein the second portion of the elongate member axial length is formed of a second material; and
wherein the first material is different from the second material.

14. The medical device of claim 12, wherein the ventilation tube distal end is disposed proximal to the first portion of the elongate member axial length.

15. The medical device of claim 12, wherein the ventilation tube is adapted to pass through the device lumen; and
wherein advancement of the ventilation tube distally through the device lumen moves the elongate member from the first, non-expanded configuration to the second, expanded configuration.

16. The medical device of claim 12, wherein in the first, non-expanded configuration the first portion of the elongate member axial length and the balloon are folded.

17. A method of providing access to a bodily passage during dilation of a point of treatment within said bodily passage, the method comprising the steps of:
introducing a wire guide having a wire guide proximal end and a wire guide distal into said bodily passage such that the wire guide distal end is disposed within said bodily passage;
advancing the wire guide distal end distal to said point of treatment;
introducing a medical device having a medical device proximal end and a medical device distal end over the wire guide and into said bodily passage such that the medical device distal end is disposed within said bodily passage, the medical device comprising:
an elongate member having an elongate member proximal end, an elongate member distal end, an elongate member axial length extending from the elongate member proximal end to the elongate member distal end, a device lumen extending through the elongate member, an inflation lumen, and an elongate member body having a first wall thickness and a second wall thickness, a first portion of the elongate member axial length extending from the elongate member distal end toward the elongate member proximal end and a second portion of the elongate member axial length extending from the elongate member proximal end to the first portion of the elongate member axial length, the first wall thickness disposed on the first portion of the elongate member axial length and the second wall thickness disposed on the second portion of the elongate member axial length, the first wall thickness being less than the second wall thickness, the first portion of the elongate member axial length adapted to move between a first, non-expanded configuration and a second, expanded configuration, the elongate member distal end having a first outside diameter when in the first, non-expanded configuration and a second outside diameter when in the second, expanded configuration, the second outside diameter being greater than the first outside diameter;
a balloon disposed on at least a portion of the first portion of the elongate member axial length, the balloon having a balloon chamber in communication with the inflation lumen and adapted to move between a first, deflated configuration and a second, inflated configuration as fluid moves into and out of the balloon chamber; and
a ventilation tube partially disposed within the device lumen, the ventilation tube comprising a ventilation tube proximal end, a ventilation tube distal end, and a ventilation tube body that defines a ventilation tube lumen;
advancing the medical device distally over the wire guide and into said bodily passage such that the medical device distal end is disposed distal to said point of treatment;
advancing the ventilation tube over the wire guide and through the device lumen such that the ventilation tube distal end is disposed distal to the elongate member distal end;
passing fluid into the balloon chamber;
removing a portion of the fluid from the balloon chamber;
withdrawing the wire guide from said bodily passage; and
withdrawing the medical device from said bodily passage;
wherein advancement of the ventilation tube distally through the device lumen moves the elongate member from the first, non-expanded configuration to the second, expanded configuration.

18. The method of claim 17, wherein the balloon is disposed entirely on the first portion of the elongate member axial length.

19. The method of claim 17, further comprising the step of providing ventilation to said bodily passage.

20. The method of claim 17, further comprising the step of confirming placement of the balloon prior to completing the step of passing fluid into the balloon chamber.

* * * * *